United States Patent
Spodak et al.

(10) Patent No.: US 9,734,345 B2
(45) Date of Patent: *Aug. 15, 2017

(54) PORTABLE E-WALLET AND UNIVERSAL CARD

(71) Applicant: GoNow Technologies, LLC, Paoli, PA (US)

(72) Inventors: Douglas A. Spodak, Bala Cynwyd, PA (US); Ron Fridman, Paoli, PA (US)

(73) Assignee: GoNow Technologies, LLC, Paoli, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/843,865

(22) Filed: Sep. 2, 2015

(65) Prior Publication Data

US 2015/0379283 A1 Dec. 31, 2015

Related U.S. Application Data

(63) Continuation of application No. 13/836,864, filed on Mar. 15, 2013, now Pat. No. 9,317,018, which is a
(Continued)

(51) Int. Cl.
*G06Q 40/00* (2012.01)
*G06F 21/60* (2013.01)
(Continued)

(52) U.S. Cl.
CPC .............. *G06F 21/606* (2013.01); *G05B 1/01* (2013.01); *G06F 19/323* (2013.01); *G06F 21/6245* (2013.01); *G06K 7/01* (2013.01); *G06K 19/06187* (2013.01); *G06K 19/072* (2013.01); *G06K 19/0718* (2013.01); *G06K 19/0723* (2013.01); *G06K 19/07707* (2013.01);
(Continued)

(58) Field of Classification Search
USPC ....................................................... 705/44, 41
See application file for complete search history.

(56) References Cited

U.S. PATENT DOCUMENTS 4,491,725 A    1/1985 Pritchard
4,689,478 A    8/1987 Hale et al.
(Continued)

FOREIGN PATENT DOCUMENTS

WO    WO 2005/086102    9/2005
WO    WO 2007/028634    3/2007

OTHER PUBLICATIONS

European Patent Application No. 13740930.6; Supplemental Search Report; dated Nov. 9, 2015; 3 pages.
(Continued)

*Primary Examiner* — Hani M Kazimi
*Assistant Examiner* — Hatem M Ali
(74) *Attorney, Agent, or Firm* — Baker & Hostetler LLP

(57) ABSTRACT

Universal cards are used in place of all the other traditional cards which a person may want to carry. The universal card can include a short range communications transceiver to communicate with a mobile device. The mobile device can include a user interface and an e-wallet application so that the user can interface with the e-wallet application for programming the universal card via the short range communication link. Once programmed, the universal card emulates a function of a traditional card.

13 Claims, 36 Drawing Sheets

Related U.S. Application Data continuation-in-part of application No. 13/717,363, filed on Dec. 17, 2012, now Pat. No. 9,177,241, which is a continuation-in-part of application No. 13/630,248, filed on Sep. 28, 2012, now Pat. No. 9,218,557, which is a continuation-in-part of application No. 13/438,131, filed on Apr. 3, 2012, now Pat. No. 8,671,055, which is a continuation-in-part of application No. 13/359,352, filed on Jan. 26, 2012, now Pat. No. 9,195,926, which is a continuation-in-part of application No. 13/310,491, filed on Dec. 2, 2011, now Pat. No. 8,788,418, which is a continuation-in-part of application No. 12/715,977, filed on Mar. 2, 2010, now Pat. No. 9,129,270.

(51) Int. Cl.
| | |
|---|---|
| *G05B 1/01* | (2006.01) |
| *G06K 7/01* | (2006.01) |
| *G06K 19/06* | (2006.01) |
| *G06K 19/07* | (2006.01) |
| *G06K 19/077* | (2006.01) |
| *G06Q 20/36* | (2012.01) |
| *G06Q 20/32* | (2012.01) |
| *G06Q 20/34* | (2012.01) |
| *G06Q 20/38* | (2012.01) |
| *G06Q 20/40* | (2012.01) |
| *G07F 7/08* | (2006.01) |
| *G07F 7/10* | (2006.01) |
| *G06F 19/00* | (2011.01) |
| *G06F 21/62* | (2013.01) |
| *H04L 29/06* | (2006.01) |
| *H04W 12/06* | (2009.01) |
| *H04W 76/02* | (2009.01) |

(52) U.S. Cl.
CPC ....... *G06Q 20/325* (2013.01); *G06Q 20/3278* (2013.01); *G06Q 20/341* (2013.01); *G06Q 20/347* (2013.01); *G06Q 20/352* (2013.01); *G06Q 20/354* (2013.01); *G06Q 20/3552* (2013.01); *G06Q 20/3572* (2013.01); *G06Q 20/363* (2013.01); *G06Q 20/367* (2013.01); *G06Q 20/385* (2013.01); *G06Q 20/4012* (2013.01); *G07F 7/086* (2013.01); *G07F 7/0846* (2013.01); *G07F 7/1008* (2013.01); *H04L 63/0853* (2013.01); *H04W 12/06* (2013.01); *H04W 76/023* (2013.01)

(56) References Cited

U.S. PATENT DOCUMENTS

| | | | |
|---|---|---|---|
| 5,276,311 A | 1/1994 | Hennige | |
| 5,590,038 A | 12/1996 | Pitroda | |
| 5,594,493 A | 1/1997 | Nemirofsky | |
| 5,748,737 A | 5/1998 | Daggar | |
| 5,884,271 A | 3/1999 | Pitroda | |
| 5,939,699 A | 8/1999 | Perttunen et al. | |
| 6,131,811 A | 10/2000 | Gangi | |
| 6,161,005 A | 12/2000 | Pinzon | |
| 6,336,098 B1 | 1/2002 | Fortenberry et al. | |
| 6,607,136 B1 | 8/2003 | Atsmon et al. | |
| 6,617,975 B1 | 9/2003 | Burgess | |
| 6,641,050 B2 | 11/2003 | Kelley et al. | |
| 6,715,679 B1 | 4/2004 | Infosino | |
| 6,718,240 B1 | 4/2004 | Suda et al. | |
| 6,736,322 B2 | 5/2004 | Gobburu et al. | |
| 6,769,607 B1 | 8/2004 | Pitroda et al. | |
| 6,785,595 B2 | 8/2004 | Kominami et al. | |
| 6,925,439 B1 | 8/2005 | Pitroda | |
| 6,967,562 B2 | 11/2005 | Menard et al. | |
| 7,003,495 B1 | 2/2006 | Burger et al. | |
| 7,097,108 B2 | 8/2006 | Zellner et al. | |
| 7,128,274 B2 | 10/2006 | Kelley et al. | |
| 7,152,783 B2 | 12/2006 | Charrin | |
| 7,213,742 B1 | 5/2007 | Birch et al. | |
| 7,343,317 B2 | 3/2008 | Jokinen et al. | |
| 7,499,889 B2 | 3/2009 | Golan et al. | |
| 7,591,416 B2 | 9/2009 | Blossom | |
| 7,681,232 B2 | 3/2010 | Nordentoft et al. | |
| 7,708,199 B2 | 5/2010 | Gatto | |
| 7,907,896 B2 | 3/2011 | Chitti | |
| 8,082,575 B2 | 12/2011 | Doughty et al. | |
| 8,200,582 B1 | 6/2012 | Zhu | |
| 8,326,758 B2 | 12/2012 | Bennett | |
| 2002/0004746 A1 | 1/2002 | Ferber et al. | |
| 2002/0198777 A1 | 12/2002 | Yuasa | |
| 2003/0055785 A1 | 3/2003 | Lahiri | |
| 2003/0132298 A1 | 7/2003 | Swartz et al. | |
| 2003/0166400 A1 | 9/2003 | Lucas | |
| 2004/0019564 A1 | 1/2004 | Goldthwaite et al. | |
| 2004/0159700 A1 | 8/2004 | Khan et al. | |
| 2005/0021400 A1 | 1/2005 | Postrel | |
| 2005/0101314 A1 | 5/2005 | Levi | |
| 2005/0116026 A1 | 6/2005 | Burger et al. | |
| 2005/0187882 A1 | 8/2005 | Sovio et al. | |
| 2005/0194452 A1 | 9/2005 | Nordentoft et al. | |
| 2006/0081702 A1 | 4/2006 | Nandakumar | |
| 2006/0190412 A1 | 8/2006 | Ostroff | |
| 2007/0028118 A1* | 2/2007 | Brown | G06Q 20/341 |
| | | | 713/185 |
| 2007/0045401 A1 | 3/2007 | Sturm | |
| 2007/0189581 A1 | 8/2007 | Nordentoft et al. | |
| 2007/0252010 A1 | 11/2007 | Gonzalez et al. | |
| 2007/0254712 A1 | 11/2007 | Chitti | |
| 2007/0278291 A1 | 12/2007 | Rans et al. | |
| 2007/0288313 A1 | 12/2007 | Brodson et al. | |
| 2008/0059379 A1 | 3/2008 | Ramaci et al. | |
| 2008/0099566 A1 | 5/2008 | Maus | |
| 2008/0120186 A1 | 5/2008 | Jokinen et al. | |
| 2008/0147546 A1 | 6/2008 | Weichselbaumer et al. | |
| 2008/0201212 A1* | 8/2008 | Hammad | G06Q 20/045 |
| | | | 705/13 |
| 2009/0103732 A1 | 4/2009 | Benteo et al. | |
| 2009/0199206 A1 | 8/2009 | Finkenzeller et al. | |
| 2009/0261166 A1 | 10/2009 | Lawson et al. | |
| 2010/0057580 A1 | 3/2010 | Raghunathan | |
| 2010/0280948 A1 | 11/2010 | Cohen | |
| 2011/0062242 A1 | 3/2011 | Cowcher | |
| 2011/0140841 A1 | 6/2011 | Bona et al. | |
| 2011/0218911 A1 | 9/2011 | Spodak | |
| 2011/0219026 A1 | 9/2011 | Schonemann | |
| 2012/0072350 A1* | 3/2012 | Goldthwaite | G06K 7/0004 |
| | | | 705/44 |
| 2012/0074232 A1 | 3/2012 | Spodak | |
| 2012/0123937 A1 | 5/2012 | Spodak | |
| 2012/0191612 A1 | 7/2012 | Spodak et al. | |

OTHER PUBLICATIONS

European Patent Application No. 13740930.6; European Search Opinion; dated Jan. 19, 2016; 4 pages.
International Patent Application No. PCT/US2011/63319: International Search Report and Written Opinion dated Apr. 25, 2012, 15 pages.
International Patent Application No. PCT/US2013/023149: International Search Report and Written Opinion dated Jun. 5, 2013, 40 pages.
Smart cards: Anonymus; Retail Delivery strategies 9 (1998):5-27.
Smart cards Do not have all the answers: Motoco Rich and Gerge Graham Financial Times. Fianancial Post [Toronto,ont] Aug. 27, 1996:53.
AT & T joins banks in Mondex line-up: Anonymus. Financial Technology International Bulletin 13.12 (Aug. 1996): 1.

(56) References Cited

OTHER PUBLICATIONS

European Patent Application No. 11876646.8; Extended Search Report; dated Sep. 24, 2015; 5 pages.

* cited by examiner

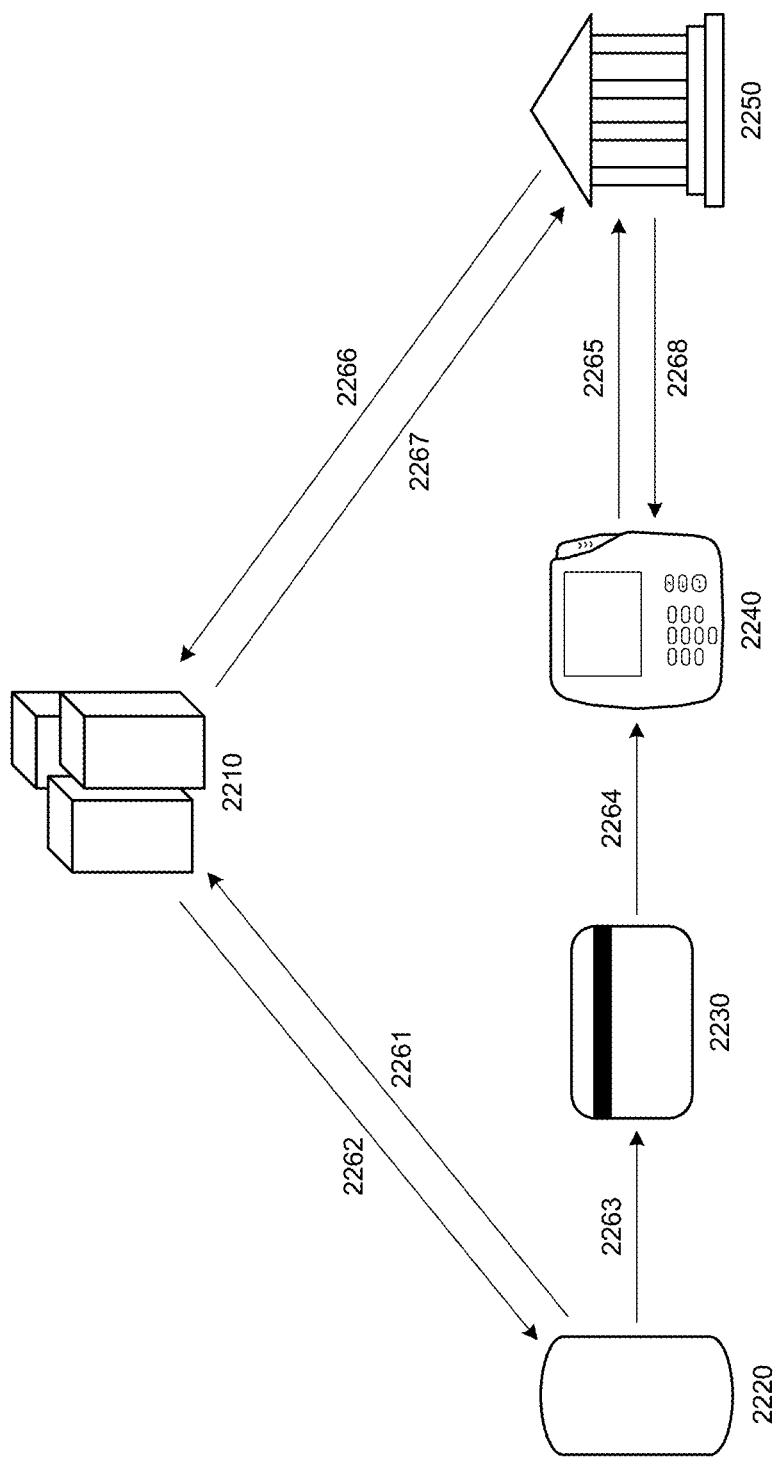

PORTABLE E-WALLET AND UNIVERSAL CARD

CROSS REFERENCE TO RELATED APPLICATION

This application is a continuation of U.S. patent application Ser. No. 13/836,864, which is a continuation-in-part of U.S. patent application Ser. No. 13/717,363 filed Dec. 17, 2012, which is a continuation-in-part of U.S. patent application Ser. No. 13/630,248 filed Sep. 28, 2012, which is a continuation-in-part of U.S. patent application Ser. No. 13/438,131 filed Apr. 3, 2012, which is a continuation-in-part of U.S. patent application Ser. No. 13/359,352 filed Jan. 26, 2012, which is a continuation-in-part of U.S. patent application Ser. No. 13/310,491 filed Dec. 2, 2011 and a continuation-in-part of U.S. patent application Ser. No. 12/715,977 filed Mar. 2, 2010. This application is also related to U.S. patent application Ser. No. 13/644,714 filed Oct. 4, 2012. The contents of all of which, with the exception of U.S. patent application Ser. No. 13/836,864, are herein incorporated by reference in their entirety.

TECHNICAL FIELD

The presently disclosed subject matters relates to universal cards, mobile applications, and mobile devices such as mobile phones, Personal Digital Assistants (PDAs), iPods, tablet computers, laptop computers, and similar mobile devices. More particularly, the subject matter relates to a universal card which can be used at any type of terminal equipped with a magnetic stripe reader or a short range wireless communication capability.

BACKGROUND

People carry many types of cards with them every day. The cards include credit cards, debit cards, drivers' licenses, transportation passes, building access cards, and many other types of cards. These cards are typically carried in a wallet or purse. A person may need to use any number of cards during the course of a day. Since people do not know which of the cards will be needed on any given day, most people carry all the cards that they may need with them every day. With the proliferation of card-capable terminals, people can end up carrying an inordinate amount of cards with them every day.

Many people also carry mobile devices with them, such as cell phones, PDAs, tablet computers, laptop computers, and many other types of mobile devices. Mobile devices increasingly have short range communication capabilities, such as near field communication (NFC) capabilities or Bluetooth capabilities.

A person that carries a wallet or purse also has to secure the contents of the wallet or purse at all times to protect against theft and fraud. If a card is lost or stolen, it can be used in unauthorized ways, leading to identification theft, fraud, or financial loss. In addition, as many transactions are increasingly performed without the need for physically possessing the card (e.g., online purchases), the mere exposure of the information found on a card to an unauthorized person is a risk to the card holder.

There is a need to reduce the number of cards carried by a person, and an opportunity to address that need using the short range communication capabilities of a mobile device which that person carries. In addition, there is a need to secure cards and card information so that cards and card information is not exposed to unauthorized people.

SUMMARY

To reduce the number of cards carried by a person, a universal card and short range communication enabled mobile device can be used in place of all the other cards which the person may want to carry. The universal card can include a short range communications transceiver to communicate with a mobile device. The mobile device can include a user interface and an e-wallet application so that the user can interface with the e-wallet application for programming the universal card via the short range communication link. Once programmed, the universal card emulates a function of a traditional card, such as emulating the magnetic stripe of the traditional card, the NFC communication of the traditional card, the radio transmission of the traditional card, or any other function.

BRIEF DESCRIPTION OF THE DRAWINGS

The foregoing Summary, as well as the following Detailed Description, is better understood when read in conjunction with the appended drawings. In order to illustrate the present disclosure, various aspects of the disclosure are shown. However, the disclosure is not limited to the specific aspects shown. The following figures are included:

FIG. 22 depicts an embodiment of a system and method of using a universal card as a proxy card.

DETAILED DESCRIPTION OF ILLUSTRATIVE EMBODIMENTS

Figure 1:
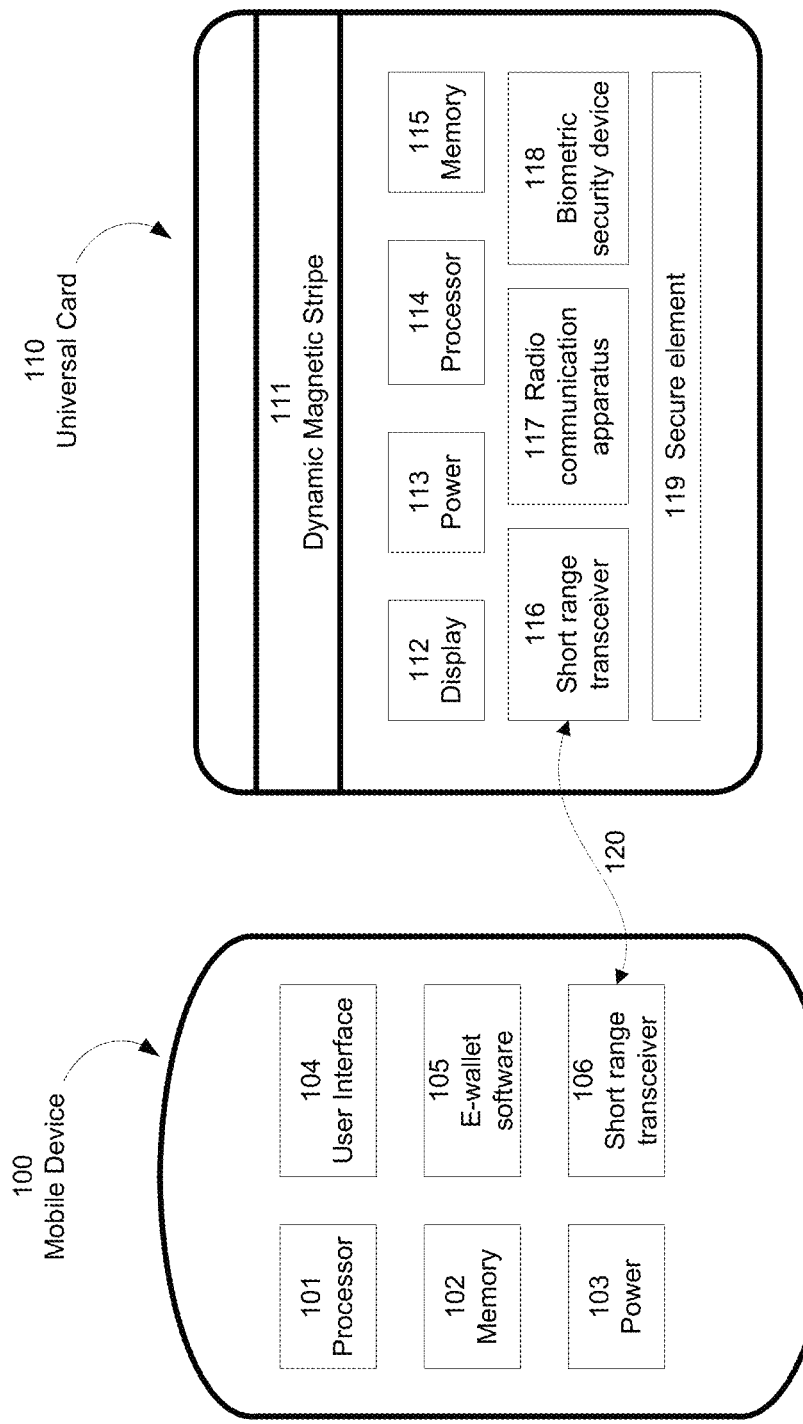
FIG. 1 depicts an exemplary system including a mobile device and a universal card.

Referring to FIG. 1, an exemplary system is depicted with a mobile device 100 and a universal card 110. The mobile device 100 can be any number of devices, including a cell phone, a PDA, an iPod, a tablet computer, an NFC-specialized device, or any other type of mobile device. An NFC-specialized device is a device that provides for the user to be able to communicate with NFC terminals, such as making a contactless payment, and would also provide a user with a user interface for interacting with an NFC-enabled universal card. The mobile device 100 may include any number of components, such as a processor 101, memory 102, a power source 103, a user interface 104, and a short range transceiver 106. Memory 102 can be any type of computer storage media in the form of volatile and/or nonvolatile memory such as read only memory (ROM) and random access memory (RAM). Processor 101 can operate on data and/or software applications available in the memory 102. The user interface 104 can include any components for user input, such as a keyboard, a mouse, a trackball, a touch screen display, or any similar component. The user interface 104 can also include security features on the mobile device, such as a PIN/password login, a fingerprint scanner, other biometric readers, or similar security features.

The mobile device 100 also includes an e-wallet application 105 which is executable by the processor 101. The e-wallet application 105 can be pre-installed on the mobile device 100 by the manufacturer of the mobile device 100. The e-wallet application 105 can also be installed by the user either by downloading it directly to the mobile device 100, by downloading the e-wallet application 105 over-the-air via a wireless data connection, or by inserting a memory card containing the e-wallet application 105.

The e-wallet application 105 allows the user to input information about traditional cards for storage in the memory 102. Information about traditional cards can include an account name, an account number, an expiration date, a card verification value 2 (CVV2), the image of the traditional card, the information which would be stored on the magnetic stripe of the traditional card, and any other information necessary to emulate the card. The information about traditional cards can also be stored in a remote location, such as a trusted service manager (not shown), which stores the information and provides the information to the mobile device 100 on demand via wireless data communication. In this case, the e-wallet application 105 would interface with the remote location to request and receive the information.

The e-wallet application 105 can also be used to program the universal card 110 by allowing the user to select a traditional card for the universal card to emulate. The universal card 110 can be configured to emulate any number of traditional cards, including credit cards, debit cards, drivers' licenses, transportation passes, building access cards, and any other types of cards. Once the user selects a card for emulation, the e-wallet application 105 causes the mobile device to communicate with the universal card and to transmit the information necessary for the universal card to emulate the selected traditional card.

In another universal card embodiment, the information about the traditional card could be stored in the memory 115 of the universal card 110. In this embodiment, if the universal card 110 has a user interface with sufficient capabilities, the user may be able to program the card by using the user interface on the universal card 110.

The short range transceiver 106 can be configured to communicate via any type of short range communication link, such as an NFC communication link or a Bluetooth communication link. The mobile device 100 may be manufactured with the short range transceiver 106. However, not all mobile devices are initially manufactured with short range transceivers. The short range transceiver 106 may be located on a memory card compatible with a memory slot of the mobile device 100. In this situation, the memory card with the short range transceiver 106 is inserted into the memory slot (not shown) of the mobile device 100 such that the mobile device can transmit and receive information using a short range communication link corresponding to the short range transceiver 106.

Another issue with the short range transceiver 106 may arise if the short range transceiver 106 of the mobile device and the short range transceiver 116 of the universal card 110 are not configured for the same type of short range communication. For example, mobile device 100 may have a Bluetooth transceiver, and the universal card 110 may have an NFC transceiver. In such a situation, the short range transceiver 106 would be a two-type transceiver, capable of communicating via both types of short range communication. In the example above, the short range transceiver 106 would be capable of receiving information via the Bluetooth link from the mobile device 100, and also capable of sending that information via the NFC link to the universal card 110. The short range transceiver 106 would also be capable of communicating in the opposite direction, receiving information via the NFC link from the universal card 110 and sending that information via the Bluetooth link to the mobile device 100. One example of a two-type transceiver is a MyMax sticker produced and sold by TwinLinx of France. The MyMax sticker can be attached to the housing of a Bluetooth-enabled device, can communicate with the device via a Bluetooth connection, and can communicate via an NFC connection with an NFC-enable device.

Also depicted in FIG. 1 is a universal card 110. The universal card 110 may include components such as a display 112, a power source 113, a processor 114, and memory 115. Each of those components are similar in function to the corresponding components of the mobile device 100, except that the component of the universal card 110 may be physically configured differently so as to fit in the shape of the universal card 110. For example, the display 112 of the universal card 110 may be integrated into universal card 110 via hot lamination processes and standard inlay constructs so that the universal card 110 will be the approximate shape and size of a traditional credit card and generally compliant with ISO 7810 standards.

The universal card 110 may also include a dynamic magnetic stripe 111 which can be configured to emulate the magnetic stripe of any traditional card. The standard magnetic stripe format is defined by ISO/IEC 7810:2003, and its extensions, including ISO/IEC 7811-1:2002 through ISO/IEC 7811-9:2008, and ISO/IEC 7813:2006, each of which are hereby incorporated by reference. Traditional magnetic stripes include a series of tiny bar magnets which can be magnetized in either a north- or south-pole direction. When the polarity of the bars aligns in the same direction, the card is blank. To write data to the card, the polarity of a bar is reversed so that the north pole is facing the north pole of the adjacent bar (N-N) or the south pole is facing the south pole (S-S). This causes a change in the magnetic field that can be detected by a card reader. The two possible flux reversals, N-N or S-S, can represent two different information states, which corresponds nicely to the binary system (ones and zeros) used by computers.

Figure 2:
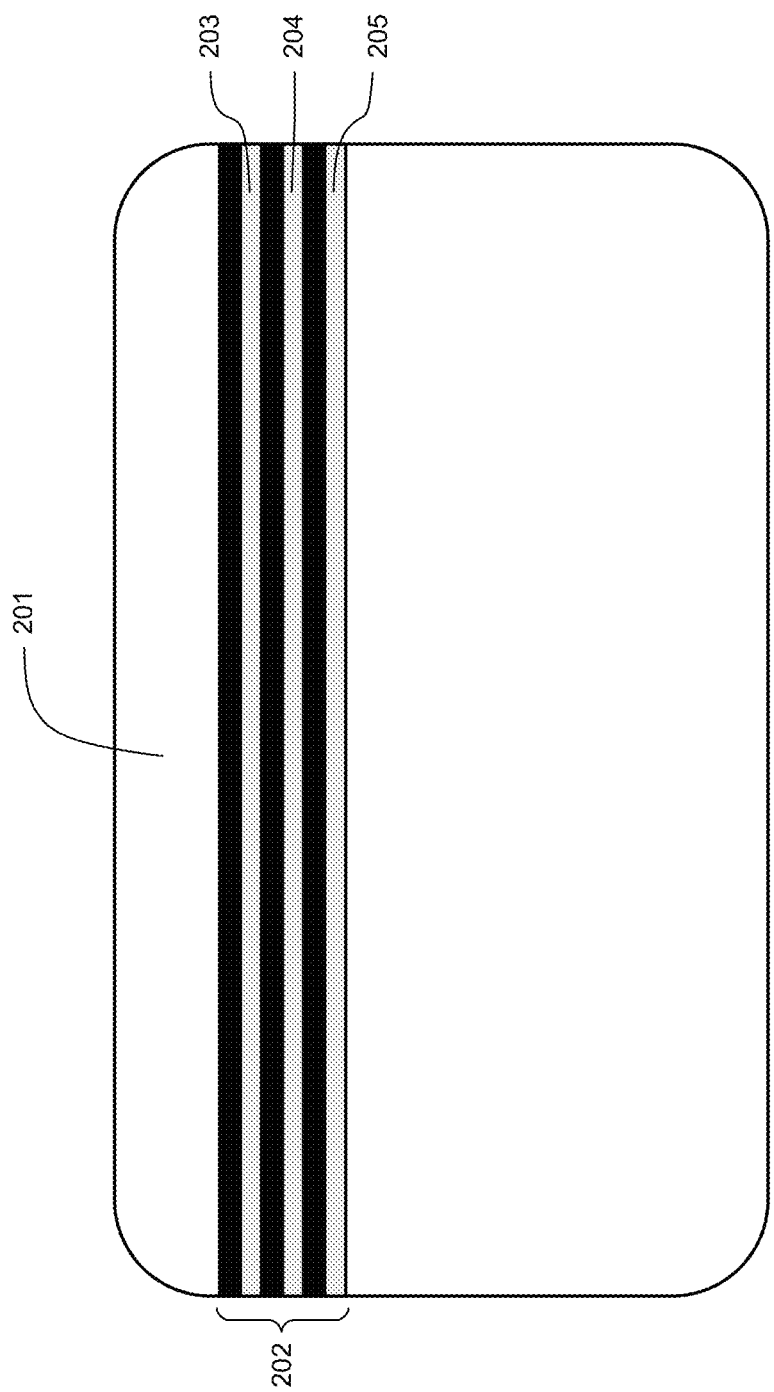
FIG. 2 depicts a traditional card with a static magnetic stripe.

Magnetic stripes have three standard track layouts: Track 1, Track 2, and Track 3. Referring to FIG. 2, depicted is a traditional card 201 with a static magnetic stripe 202. The static magnetic stripe includes each of Tracks 1, 2, and 3, shown as 203, 204, and 205, respectively. Each of the track layouts are 0.110 inches high. Track 1 has 210 bits per inch (bpi) with room for 79 characters of 7 bits each (6 data bits, plus 1 parity bit). Track 2 has 75 bpi with room for 40 characters of 5 bits each (4 data bits, plus 1 parity bit). Track 3 has 210 bpi with room for 107 numeric digits. Tracks 1 and 2 have a standard for the data content contained in each track. Those standards are shown in Tables 1 and 2 below. In contrast, Track 3 does not have a standard for the data content in the track, and can be used for proprietary data formats.

TABLE 1

Standard Track 1 Data Content in Magnetic Stripe of Financial Cards

| Data Field | Content of Data Field |
| --- | --- |
| Start sentinel | 1 byte (the % character) |
| Format code | 1 byte alpha ("A" is reserved for proprietary use of the card issuer; "B" is a standard for financial institutions; "C"-"M" are reserved for use by ANSI; and "N"-"Z" are available for use by individual card issuers) |
| Primary Account number | Up to 19 characters |
| Separator | 1 byte (the ^ character) |
| Country code | 3 bytes (optional) |
| Surname | Variable number of bytes |
| Surname separator | 1 byte (the / character) |
| First name or initial | Variable number of bytes |
| Space | 1 byte (used only when more data follows the first name or initial) |
| Middle name or initial | Variable number of bytes |
| Period | 1 byte (the . character; used only when followed by a title) |
| Title | Variable number of bytes (optional) |
| Separator | 1 byte (the ^ character) |
| Expiration date or separator | 4 bytes (YYMM format), or a 1-byte separator if non-expiring card |
| Discretionary data | Variable number of bytes (optional; can be used by the card issuer) |
| End sentinel | 1 byte (the ? character) |
| Longitudinal redundancy check | 1 byte |

TABLE 2

Standard Track 2 Data Content in Magnetic Stripe of Financial Cards

| Data Field | Content of Data Field |
| --- | --- |
| Start sentinel | 1 byte (the ; character) |
| Primary account number | Up to 19 bytes |
| Separator | 1 byte (the = character) |
| Country code | 3 bytes (optional) |
| Expiration date or separator | 4 bytes (YYMM format), or a 1-byte separator if non-expiring card |
| Discretionary data | Variable number of bytes (optional; can be used by the card issuer) |

TABLE 2-continued

Standard Track 2 Data Content in Magnetic Stripe of Financial Cards

| Data Field | Content of Data Field |
|---|---|
| End sentinel | 1 byte (the ? character) |
| Longitudinal redundancy check | 1 byte |

Traditional financial cards from the banking industry, such as credit cards and debit cards, typically use both Tracks 1 and 2, with Track 2 using format code "A" or "B". Some traditional credit and debit cards do not have Track 3 physically present on the cards as its data is not necessary for the cards' use. Eliminating Track 3 can reduce the physical size of the magnetic stripe. Traditional financial cards usually include all of the data listed in Tables 1 and 2.

Traditional gift cards typically use Track 2 with format code "B". Those cards usually have a unique account number, but usually do not contain the name of the user in the track. Some traditional gift cards can include the amount available at the time of the original purchase in the magnetic track, and some will store the current balance on the card so that the card can be used at any terminal. However, most traditional gift cards do not have any value data stored on the card; the card merely stores the unique account number, and each terminal at the store is connected to a database, where the value of the card is associated with the unique account number.

Traditional loyalty cards typically use Track 2 with format code "B". Like traditional gift cards, traditional loyalty cards typically include only a unique account number without storing any data about the user or any monetary value associated with the card. Most terminals which accept loyalty cards are connected to a central database which associates data about the user with the unique account number. Some traditional loyalty cards also include a barcode printed on the face of the card so that the card can be read by a barcode scanner. The barcode is representative of the unique account number of the user, and typically has no other data encoded in the barcode itself Many driver's licenses issued in the United States have a magnetic stripe on them. Driver's licenses typically include Tracks 1, 2, and 3. The data content of Tracks 1 and 2 are shown in Table 3. The data content of Track 3 is not entirely standardized, but Track 3 typically includes at least some of the following data categories: template number, security number, postal code, class, restrictions, endorsements, sex, height, weight, hair color, eye color, ID number, error correction, and security field.

TABLE 3

Standard Track 1 and Track 2 Data Content of US Driver's Licenses

| | Content of Data Field |
|---|---|
| Track 1 Data Fields | |
| Start sentinel | 1 character (usually the % character) |
| State or province | 2 characters |
| City | Up to 13 characters (variable length) |
| Field separator | 1 character (usually the ^ character), unless the City field is maxed out |
| Last name | Variable length |
| Field separator | 1 character (usually the $ character) |
| First name | Variable length |
| Field separator | 1 character (usually the $ character) |
| First name | Variable length |
| Field separator | 1 character (usually the ^ character) |

TABLE 3-continued

Standard Track 1 and Track 2 Data Content of US Driver's Licenses

| | Content of Data Field |
|---|---|
| Home address | Variable length (usually house number and street) |
| Field separator | 1 character (usually the ^ character) |
| Discretionary data | Variable length |
| Start sentinel | 1 character (usually the ^ character) |
| Track 2 Data Fields | |
| ISO issuer ID number | 6 character |
| License/ID number | 8 character |
| Field separator | 1 character (usually the = character) |
| Expiration date | 4 characters (usually YYMM format) |
| Birth date | 8 characters (usually YYYYMMDD format) |
| License/ID number overflow | Variable length |

Traditional access cards are used to provide access to the card holder to a building or other secure area. Traditional access cards typically use either a magnetic stripe or a radio transmitter to convey information to a terminal. When using a magnetic stripe, the data encoded on the magnetic stripe typically includes the user's name, an ID number associated with the user, and an access level relating to where and when the user is allowed access. When using a radio transmitter, the access card typically only includes an ID number associated with the user, and the access terminal is connected to a database which contains information about the user and the access level based on the ID number. Radio transmitters in access cards can either be "active" radio transmitters (powered by a power source on the card), or "passive" radio transmitters (powered by the radio receiver in the terminal when the card is brought into close proximity with the terminal).

Referring back to FIG. 1, universal card 110 can also include a radio communications apparatus 117 to emulate an access card which uses a radio communications apparatus. Radio communications apparatus 117 can either be a passive radio transmitter, or an active radio transmitter powered by power source 113. The ID number transmitted by the radio communications apparatus 117 can be programmed so that the universal card can programmed to emulate different traditional access cards. When programming the universal card 110 to emulate an access card, it may be desirable to verify the identity of the user prior to programming the universal card 110. Examples of user verification are discussed below.

Other types of traditional cards exist and can be emulated by universal card 110. Examples of dynamic magnetic stripes are shown in US Patent Application Publication 2005/0194452, applied for by Nordentoft et al, and 2007/0189581, applied for by Nordentoft et al. In these examples, individually inducible transducer coils are positioned within a universal card and are configurable to emulate the static magnets in a traditional magnetic stripe. The dynamic magnetic stripe 111 of the universal card can be configured to emulate any traditional static magnetic stripe, including any data or data format used by a static magnetic stripe. Thus, even if a data content format is not discussed here, dynamic magnetic stripe 111 would be capable of emulating the data content format not discussed here.

Universal card 110 may include a biometric security device 118, such as a fingerprint reader, a microphone for voice identification, or other device for input during biometric identification. The use of such biometric identification for security is discussed below.

Figure 3:
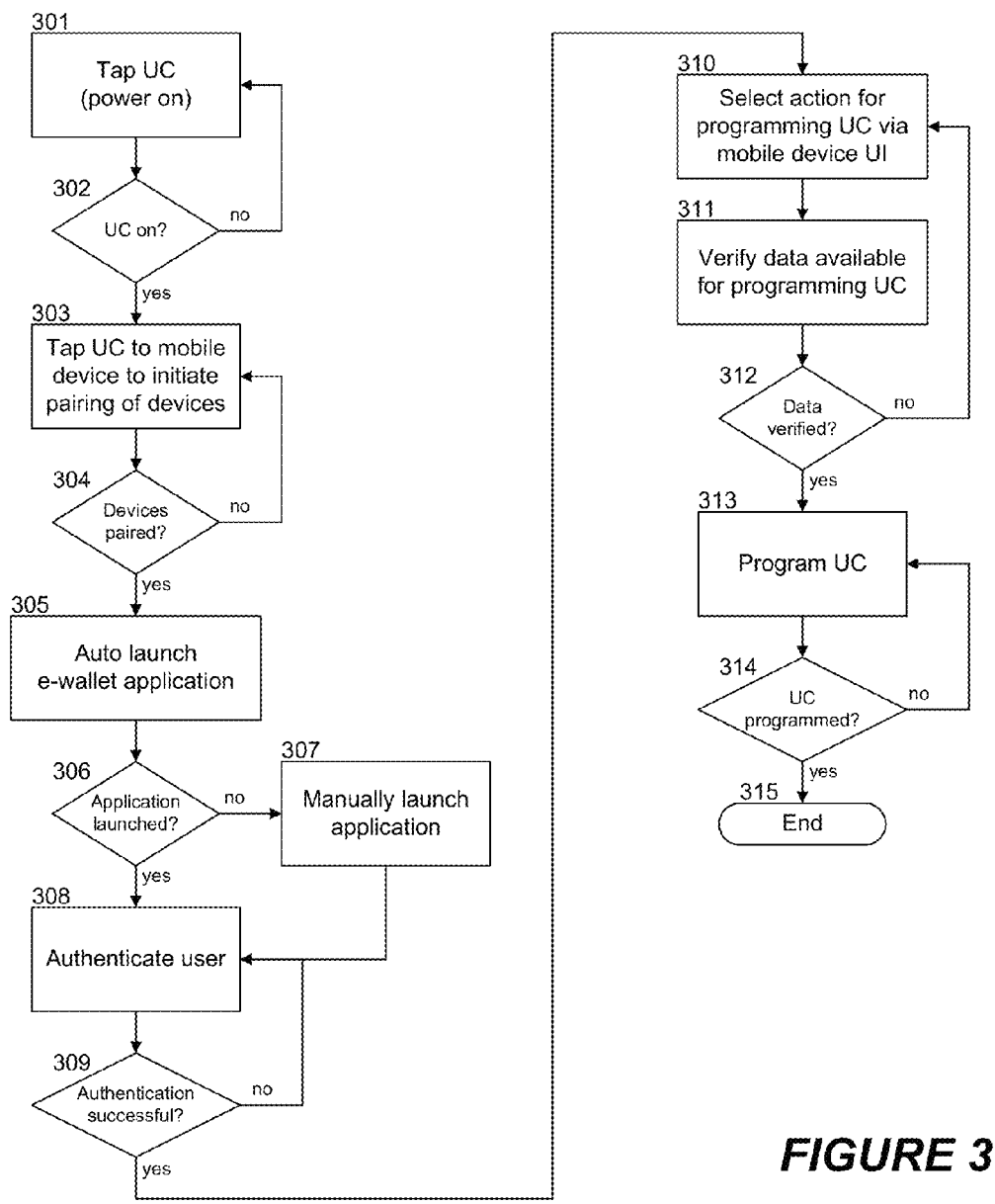
FIG. 3 depicts a flowchart process for programming a universal card.

Referring now to FIG. 3, depicted is a flowchart process for programming a universal card. To initiate power on the universal card (UC) the user may be required to take an action that may include pushing a button on card to turn it "on", is tapped 301, or any other similar technique. The universal card's power is verified 302. If the power is not on, the user will repeat the action to initiate power 301 on the universal card again. If the power is on, the universal card and the mobile device are paired 303, establishing the short range communication link 120 (as shown in FIG. 1). The pairing is verified 304, with the pairing 303 attempted again if the pairing is not successful. Once paired, an e-wallet application on the mobile device is automatically launched 305. If the e-wallet application is not automatically launched 306, it can be manually launched 307 on the mobile device.

Before allowing access to view, change or modify the financial data associated with the e-wallet program 105 on the mobile device 100 or on the universal card 110, the user must first be authenticated 308. Authentication can take a number of forms. One form of authentication can be verification of something that the user has in their possession. In this context, one security feature could be that the mobile device 100 can only be paired with one universal card 110, and the universal card 110 will only pair to one mobile device 100. For example, if a user's mobile device 100 is lost or stolen, the universal card 110 will not pair with any other mobile device. Thus, any personal card information stored on the universal card 110 will not be accessible by another mobile device.

Another form of user authentication can be verification of something that the user knows. This can be a personal identification number (PIN), a unique identification of the user (such as a social security number), a fact about the user (such as the maiden name of the user's mother), a password, or anything else that the user can input. Yet another form of user authentication is something about the user. This can include a fingerprint, a voice identification, or other verifiable biometric.

While each of these forms of authentication can alone authenticate the user, it may be desirable to require at least two forms of authentication to ensure increased security. For example, the mobile device 100 and the universal card 110 may authenticate each other as being paired; however, this fact alone does not ensure that the person operating the devices is the authentic user. In this case, it may be advantageous to require the user to enter a password to verify that the user is authentic. In some instances, the issuer of the card may impose additional requirement depending on the circumstances that the card is being used. For example, if the card is being used to make a payment over a certain value, if the card is being used in a foreign country, or if the card issuer has reason to suspect that the use of the card is unauthorized, the issuer may require another level of authentication. In this case, if the initial authentication included pairing authentication and a user password, the issuer may require an additional biometric authentication.

Any user input required for authentication can be entered into either the universal card 110 or the mobile device 100. The universal card 110 may have a user interface (not shown), an optional biometric security device 118, or other input mechanism which allows the user to input the required value. Similarly the mobile device 100 may have a user interface 104, an optional biometric security device (not shown), or other input mechanism.

Once the user authentication 308 occurs (e.g., a password is entered), the authentication is verified 309 (the entered password is verified). If the authentication was not successful, user authentication 308 can be attempted again. If the authentication is successful, the user is prompted to select 310 an action for programming the universal card.

Notwithstanding the foregoing, it should be clear to a person skilled in the art that radio interfaces 120, 410, 430, 450, 510, and 520 may be subject to eavesdropping or other intrusive information breaches can be protected by data encryption technologies public key, private key and other known and standard methods of radio protection.

The universal card can be programmed in many ways, including three distinct modes. First, the universal card can be programmed in a "dummy card" mode, where the universal card does not itself store any of the information required for emulation of a traditional card. In this case, the user must use the mobile device to program the universal card for each use of the card. Once the universal card is used once as programmed, it would not retain that programmed setting, and it would require re-programming if it were to be used again. Second, the universal card can be programmed in a "temporary card" mode, where the universal card stores only one set of information required for emulation. The user utilizes the mobile device to program the card to emulate a specific card either for a set amount of time or number of transactions. Once programmed in this mode, the universal card would remain programmed to emulate that one card for the set time or the number of transactions. If the user wanted to change the universal card to emulate a different card, the user would need to reconnect the mobile device to reprogram the card. Third, the universal card can be programmed in a "default card" mode, where the universal card always emulates a specific card, unless programmed otherwise. In this mode, the information of the default card is saved in the universal card and the universal card is always configured to emulate the default card, unless the user re-programs the universal card to temporarily act as another card or to change to a new default card.

It may also be possible to program the universal card in different modes for the various ways in which the universal card can be used. For example, a universal card which has both a dynamic magnetic stripe and an NFC transceiver can be used to interface with both magnetic stripe readers and NFC-equipped terminals. The user may use the universal card as a public transportation pass which makes fare payments to an NFC-equipped terminal, and as a credit card with a magnetic stripe reader. In such a case the user may program the NFC transceiver to operate in a "default card" mode, always capable of emulating the public transportation pass, but program the dynamic magnetic stripe in a "dummy card" mode where the user must program the universal card with a specific credit card to emulate before each transaction.

Once the user selects 310 an action for programming, the data required for the programming action is determined 311. In order for the universal card to be programmed to emulate a magnetic stripe of a payment card, the universal card would need all the data required to be in the dynamic required stripe. The data could include all the information needed to fill Track 1 and Track 2, as discussed above and shown in Tables 1 and 2. The required data may be stored on the mobile device, the universal card, or a remote location such as a trusted service manager. If it is determined 312 that the required data is not available, the user is prompted to select 310 another action for programming If the required data is available, the universal card is programmed 314 to emulate the selected card with the required data. If the required data is stored only on the mobile device, the programming 314 will include transmitting the required data to the universal card via the short range communication link. If the required data is stored on the universal card, the programming 314 need only include configuring the appropriate device (e.g., dynamic magnetic stripe, short range transceiver, radio transmitter, etc) properly for emulation.

Figure 4:
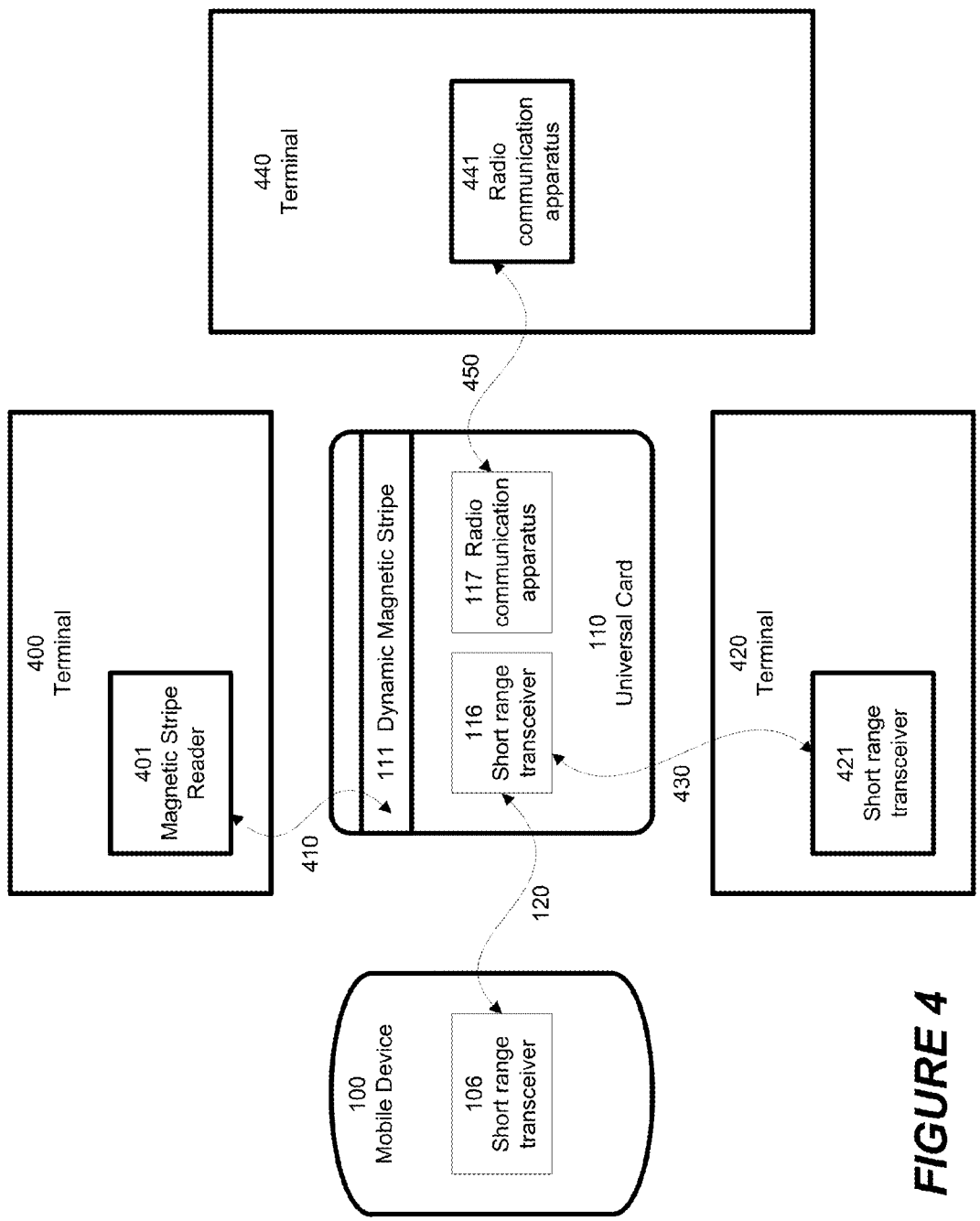
FIG. 4 depicts interactions between a mobile device and a universal card, and between a universal card and three different types of terminals.

Referring to FIG. 4, depicted are interactions between the mobile device 100 and the universal card 110, and between the universal card 110 and three different types of terminals 400, 420, and 440. As discussed above, the mobile device 100 communicates with the universal card 110 via a short range communications link 120 to program the universal card 110 for emulation of traditional cards. The universal card 110, in turn, can communicate with terminals 400, 420, and 440 in a number of ways. It is important to note that, once universal card 110 is programmed, the short range communications link 120 between the mobile device 100 and the universal card 110 need not be established for the universal card 110 to interact with the terminals 400, 420, and 440.

Terminal 400 is equipped with a magnetic stripe reader 401 which can read the dynamic magnetic stripe 111 of the universal card 110 when it is swiped 410 through the magnetic stripe reader 401. The magnetic stripe reader 401 can read any of the data written to the dynamic magnetic stripe 111. Terminal 420 is equipped with a short range transceiver 421 which can establish a short range communication link 430 between the universal card 110 and the terminal 420. Any required data can be transmitted from the universal card 110 to the terminal 420 via the short range communication link 430. Terminal 440 is equipped with a radio receiver 241 which can receive data sent from the radio transmitter 117 of the universal card 110. Any required data can be transmitted from the universal card 110 to the terminal 440 via the radio link 450.

One potential problem with the e-wallet software 105 on the mobile device 100 is that large amounts of information may need to be inputted into the e-wallet software 105. The user interface 104 may not be convenient for entry of the large amounts of information. Also, management of the information in the e-wallet software 105 may also not be convenient via the user interface 104. To address this issue, a personal computer 500 can be used.

Figure 5:
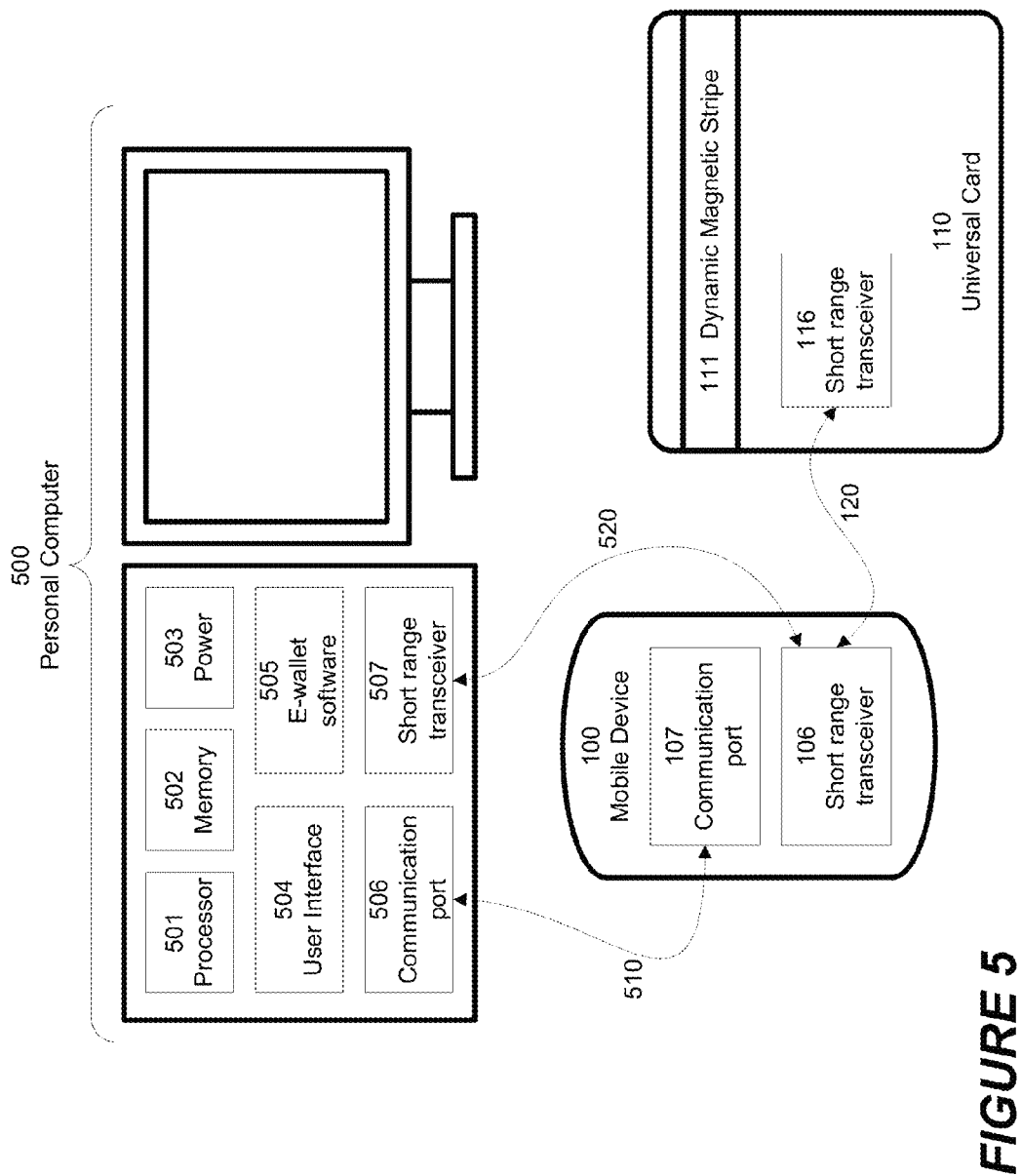
FIG. 5 depicts an exemplary system including a personal computer, a mobile device, and a universal card.

Referring to FIG. 5, depicted is an exemplary system including the personal computer 500, the mobile device 100, and the universal card 110. The personal computer can include a processor 501, memory 502, a power source 503, a user interface 504, the e-wallet software 505, and a communications port 506. The processor 501, memory 502, power source 503, and user interface 504 are all similar in function to the corresponding components of the mobile device 100, as discussed above. The e-wallet software 505 can be the same or similar to e-wallet software 105 of the mobile device 110. The user may enter data and manage the card data in e-wallet software 505 in the same way the user would use e-wallet software 105.

When the user enters data or makes changes in the management of e-wallet software 505, the e-wallet software 105 on the mobile device 100 must be updated to reflect the new and/or changed data. In order to make these updates, a communication link 510 can be established between the communication port 506 of the personal computer 500 and the communication port 107 of the mobile device 100. The communication link 510 can be any type of wired or wireless link, including a serial cable, a wired or wireless local area network (LAN), a wired or wireless wide area network (WAN), a short range communication link, a radio link, or any similar connection. Alternatively, a communication link 520 can be established between a short range transceiver 507 of the personal computer 500 and the short range transceiver 106 of the mobile device 100.

Once a communication link is established between the personal computer 500 and the mobile device 100, the data in e-wallet software 505 and the e-wallet software 105 can be synchronized. It is important to note that the short range communication link 120 between the universal card 110 and the mobile device 100 need not be active for the link 510 or the link 520 to be established between the personal computer 500 and the mobile device 100.

Figure 6:
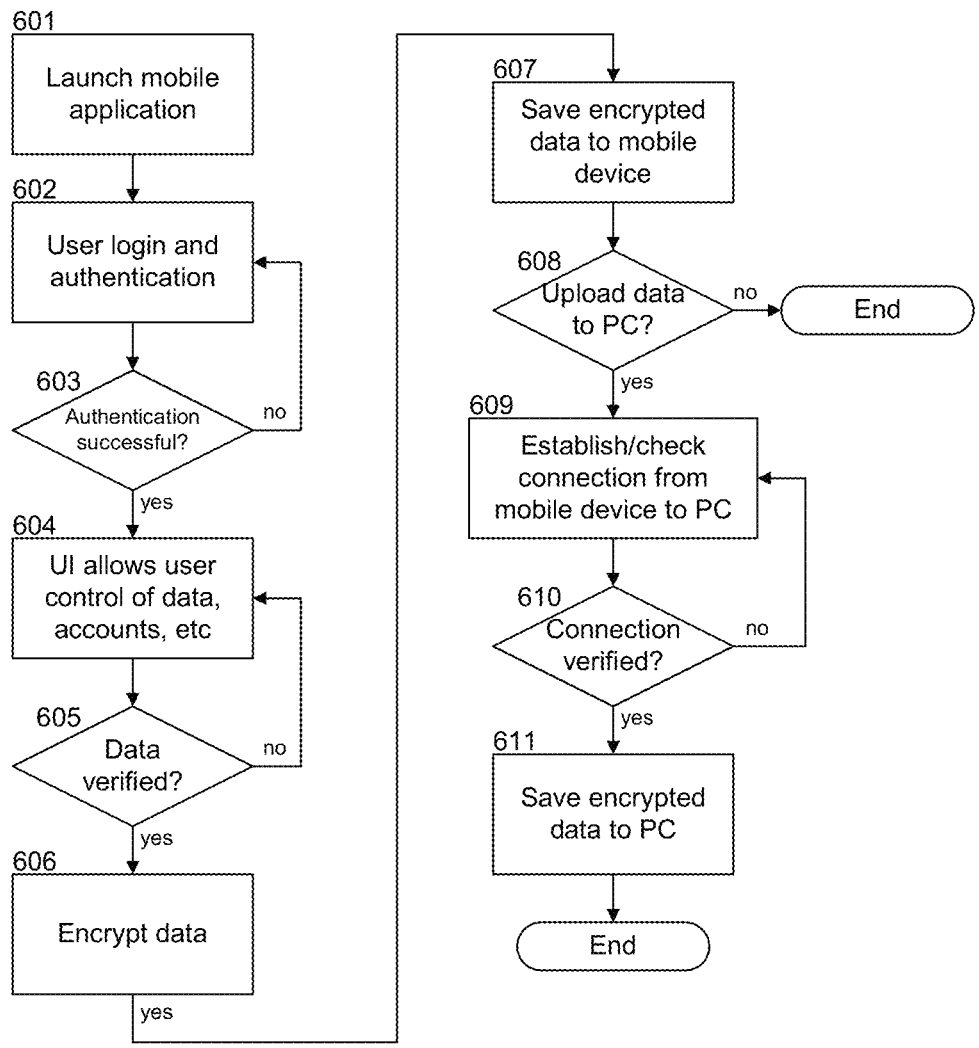
FIG. 6 depicts a flowchart process for managing universal card data using a mobile device.

Referring to FIG. 6, depicted is a flowchart process for managing universal card data using mobile device 100. The e-wallet software is launched 601 on the mobile device. Before the user is given access to the e-wallet software, the user must first login and be authenticated 602. Authentication here can be the same or similar to the forms of authentication discussed above. A determination is made whether the authentication is successful 603. If not successful, the user is prompted to login and authenticate 602 again. If the authentication is successful, the user is allowed to control 604 the e-wallet software a user interface of the mobile device.

The control 604 of the e-wallet software includes anything that the user may need to do to prepare for programming the universal card or to program the universal card. The user can enter data associated with a traditional card or with a financial account. The user can manage the entered data such as by naming a particular account or traditional card, setting a default card, or any other management action needed.

After the user enters data, the data is verified 605. The verification can include determining whether sufficient data has been entered for emulation of a traditional card, or whether the data entered matches the data of the card issuer. If the data is not verified, the user is allowed to reenter data 604. If the data is verified, the data is encrypted 606 for storage. Encrypting the data for storage is another form of security, as someone that gains access to the encrypted data cannot recover the entered data without knowing how to decrypt the encrypted data. After the data is encrypted, the encrypted data can be stored 607 to the mobile device.

A determination 608 is made as to whether the encrypted data should be uploaded to the personal computer. If the encrypted data will not be uploaded, no further action is required. If the encrypted data will be uploaded to the personal computer, the communication connection between the mobile device and the personal computer is either established or checked 609. If the connection to the computer is not verified 610, another attempt to establish 609 the connection can be attempted. Once the connection to the computer is verified 610, the encrypted data can be uploaded and saved 611 to the personal computer.

Figure 7:
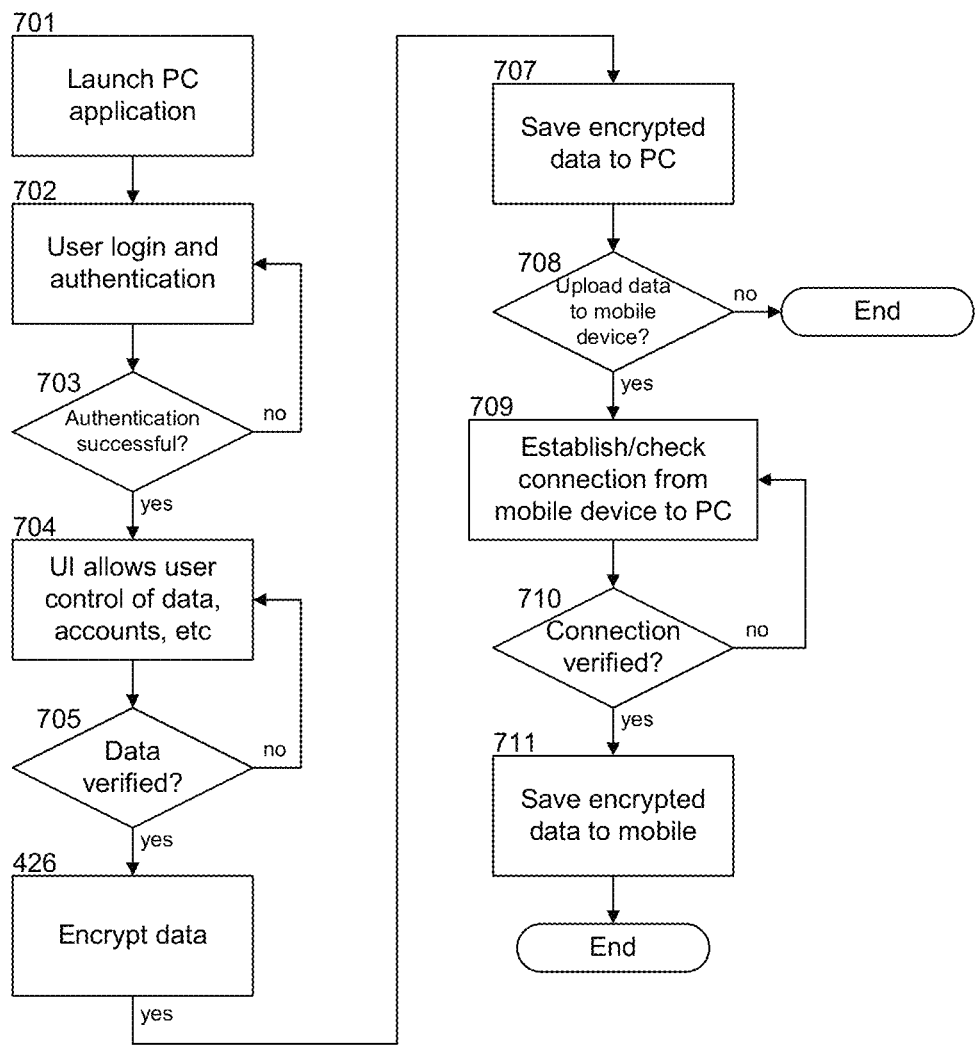
FIG. 7 depicts a flowchart process for managing universal card data using a personal computer.

Referring to FIG. 7, depicted is a flowchart process for managing universal card data using personal computer 500. Many of the steps are similar to those depicted in FIG. 6. The PC version of the e-wallet software is launched 701. The user goes through login and authentication 702 which is verified 703. Once the user authentication is verified, the user can control 704 the e-wallet software via a user interface of the personal computer. The control on the personal computer is the same as the control on the mobile device, except that the user may prefer to use the user interface of the personal computer to the user interface of the mobile device.

Data entered on the personal computer can be verified 705. Once verified, the data is encrypted 706 for storage. The encrypted data is stored 707 on the personal computer. A determination 708 is made as to whether the encrypted data should be uploaded to the mobile. If the encrypted data will not be uploaded to the mobile device, the no further action is required. If the encrypted data will be uploaded, the communication connection between the mobile device and the personal computer is either established or checked 709. If the connection to the computer is not verified 710, another attempt to establish 709 the connection can be attempted. Once the connection to the computer is verified 710, the encrypted data can be uploaded and saved 711 to the mobile device.

Figure 8A:
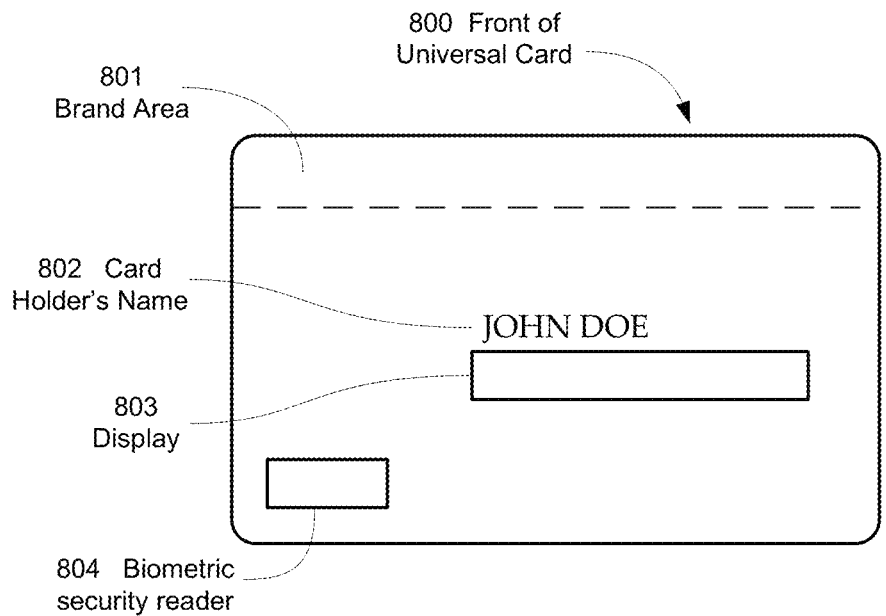
FIGS. 8A, 8B, 8C, and 8D depict possible designs for the front of a universal card.

The visible sides of a universal card may be designed in a number of ways to provide a user with access to information or components of the universal card. FIG. 8A depicts one design of the front of a universal card 800. The front of the universal card 800 can have a brand area 801 which can be used to identify the brand of the universal card issuer, the brand of a wireless carrier, the brand of a sponsor, any other brand, or any combination of those brands. The front of the universal card 800 can have the name of the card holder 802 on the face of the card to identify the user. The front of the universal card 800 can also have a display 803 which could be used at various times to display an account number, an expiration date, a card issuer logo, any other information, or any combination of these types of information. The front of the universal card 800 could also include a biometric security reader 804, such as a fingerprint reader, which is used to authenticate the user.

Figure 8B:
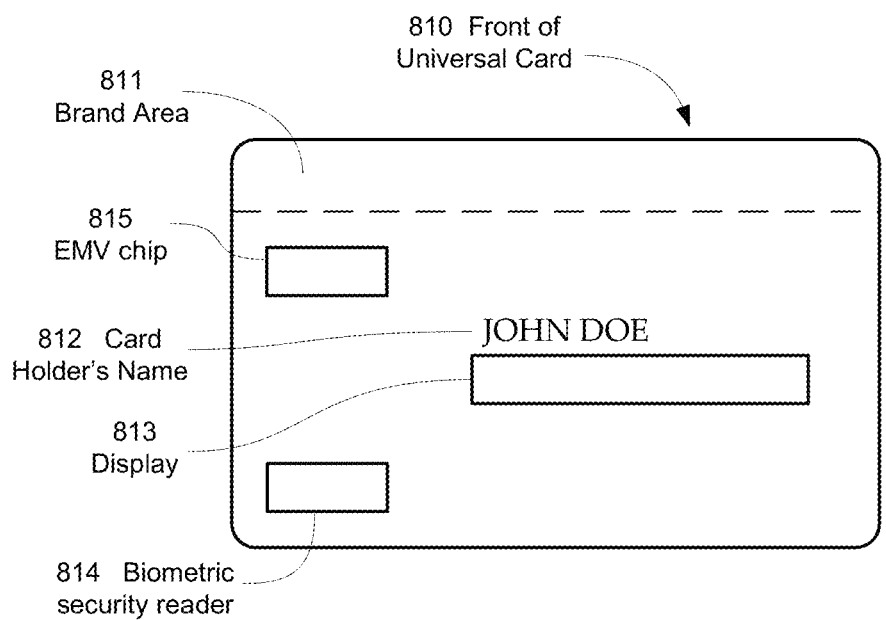
Figure 8C:
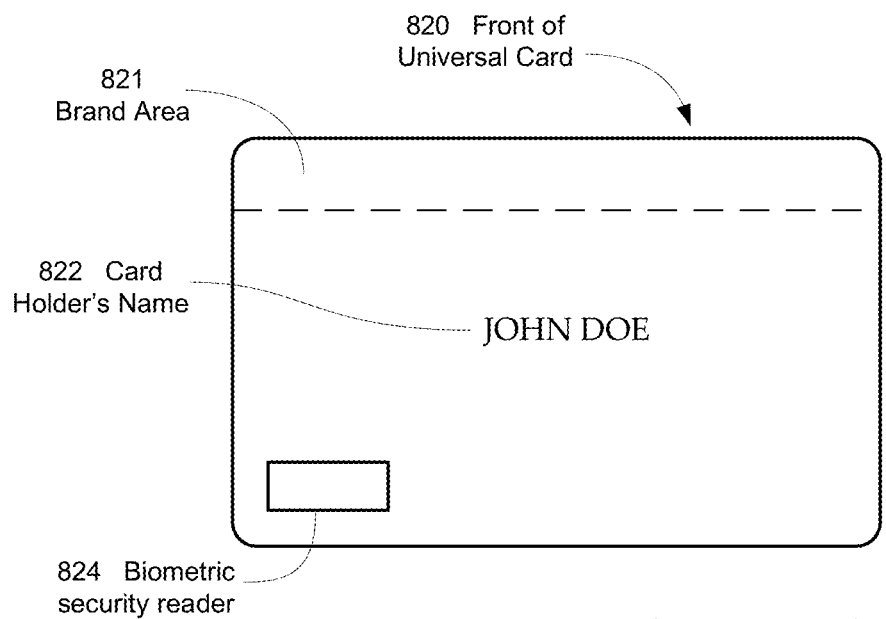
Figure 8D:
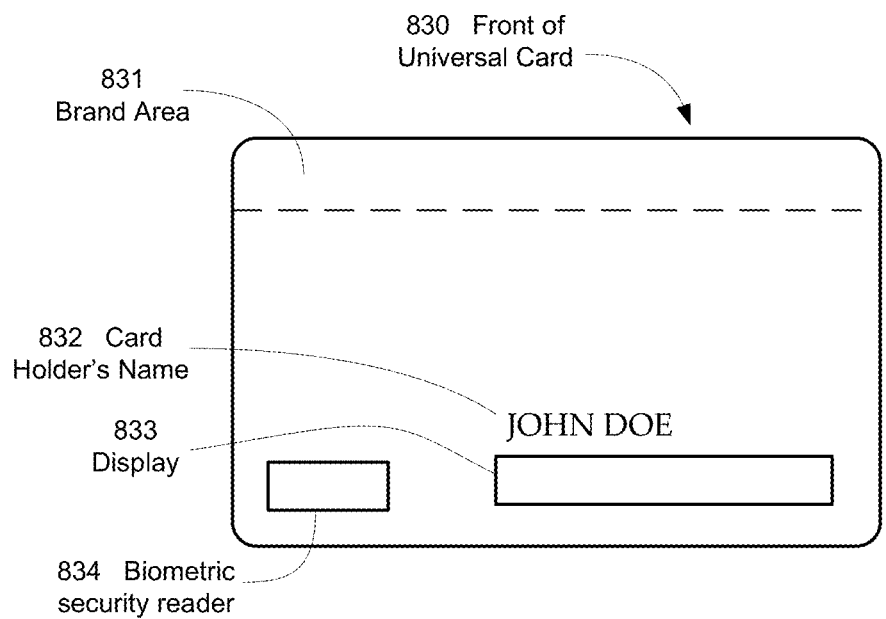

FIGS. 8B, 8C, and 8D depict other possible designs for the front of a universal card. FIG. 8B depicts the front of a universal card 810 which is similar to the front of universal card 800, including a brand area 811, the name of the card holder 812, a display 813, and a biometric security reader 814. The front of the front of the universal card 810 can also have an EMV chip 815 which is a required component of cards in some markets including some European markets. FIG. 8C depicts the front of a universal card 820 which is similar to the front of universal card 800, including a brand area 821, the name of the card holder 822, and a biometric security reader 824; however, the front of universal card 820 does not include a display. FIG. 8B depicts the front of a universal card 830 which similar to the front of universal card 800, including a brand area 831, the name of the card holder 832, a display 833, and a biometric security reader 834. The front of universal card 830 also shows that the name of the card holder 832 and the display 833 can be located in various locations on the front of a universal card.

Figure 9:
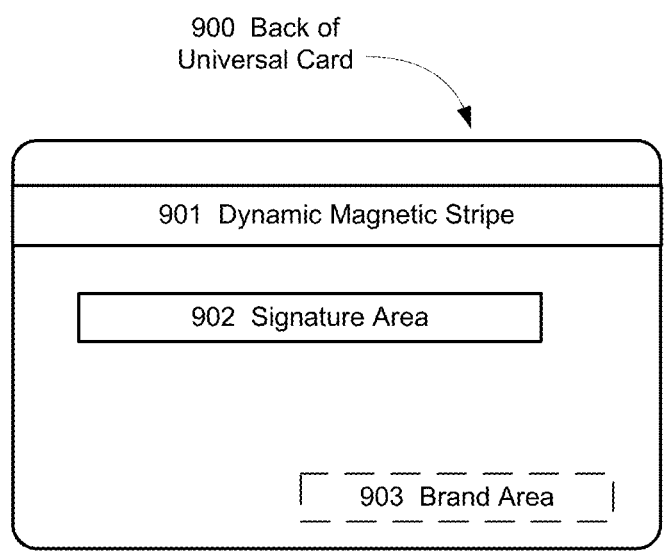
FIG. 9 depicts a possible design for the back of a universal card.

FIG. 9 depicts one design of the back of a universal card 900. The back of universal card 900 can include a dynamic magnetic stripe 901 for interacting with a terminal, a signature area 902 which displays the signature of the card holder, and a brand area 903. Similar to the brand area 801 described above, brand area 903 can be used to identify the brand of the universal card issuer, the brand of a wireless carrier, the brand of a sponsor, any other brand, or any combination of those brands.

Figure 10A:
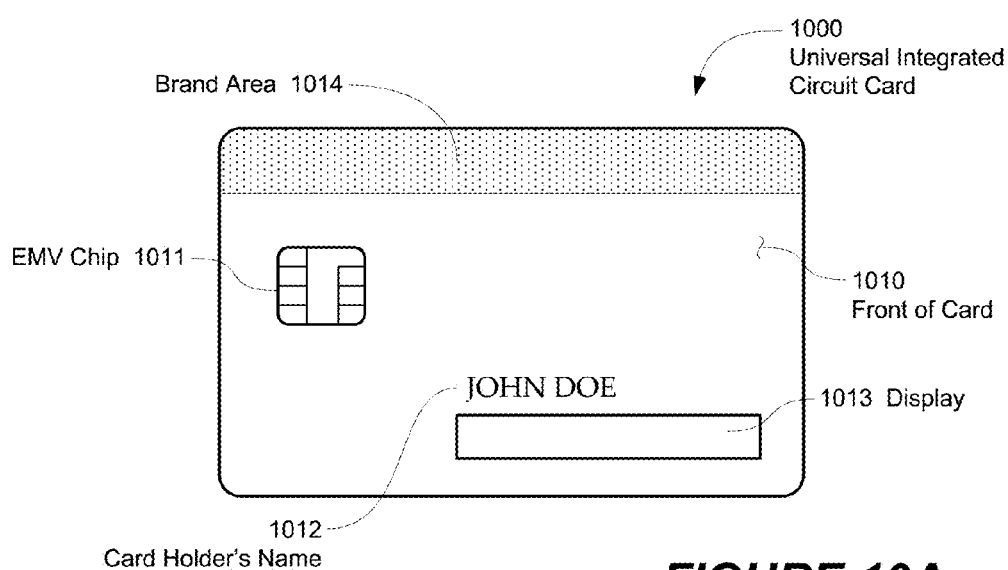
FIGS. 10A and 10B depict an embodiment of a universal card with an integrated circuit.
Figure 10B:
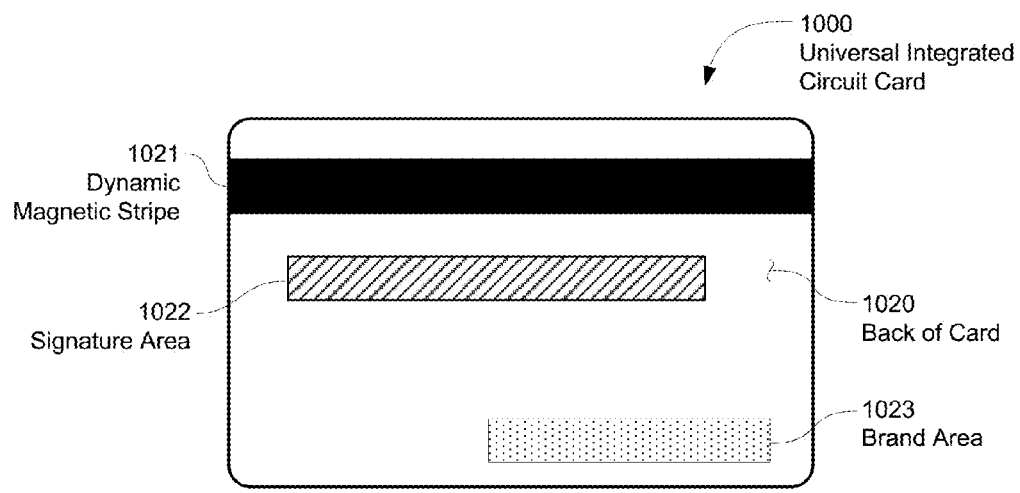

FIGS. 10A and 10B depict an embodiment of a universal integrated circuit card. In general, an integrated circuit card (also sometimes referred to as a "contact card," an "IC card," a "chip and PIN card," an "EMV card," and so forth) is a card that has an embedded integrated circuit and can be authenticated automatically using a PIN. To reduce fraud, banks and retailers are replacing traditional magnetic stripe equipment with integrated circuit cards. When a customer wishes to pay for goods using this system, the card is placed into a "PIN pad" terminal or a modified swipe-card reader, which accesses the chip on the card. Once the card has been verified as authentic, the customer enters a PIN, which is submitted to the chip on the integrated circuit cards. The chip verifies whether the PIN is correct and replies accordingly to the terminal Integrated circuit cards have been effective to significantly cut card-present (face-to-face) fraud.

The EMV standard is one standard that has been developed for integrated circuit cards; the EMV standard defines the physical, electrical, data, and application interactions between an integrated circuit card and the terminal. As mentioned above, an EMV chip is a required component of cards in some markets including some European markets. Other forms of integrated circuit cards, such as the Chip and PIN system, are used in other markets.

Increasingly it is becoming important for US citizens to have a card with both a magnetic stripe and an integrated circuit, so that when a person is traveling internationally it is easier for them to pay with a US credit card. In many countries, merchants reject credit cards with only a magnetic stripe. Thus, in order for a universal card to be usable world-wide, it must also include an integrated circuit. One difficulty with including an embedded integrated circuit with a universal card is that the integrated circuit can be associated only with a single credit or debit card.

Referring back to FIGS. 10A and 10B depict an embodiment of a universal integrated circuit card 1000. The universal integrated circuit card 1000 has a front 1010 that can include an EMV chip 1011. The front of the card 1010 can also include features such as the card holder's name 1012, a display 1013, and a brand area 1014. The universal integrated circuit card 1000 also has a back 1020 that can include a dynamic magnetic stripe 1021. The back of the card 1020 can also include features such as a signature area 1022 and a brand area 1023. The universal integrated circuit card 1000 can include any or all of the features described above with respect to universal card 110. Thus, the universal integrated circuit card 1000 can communicate with a mobile device be programmed to emulate traditional magnetic stripe cards using the dynamic magnetic stripe 1021, and the universal integrated circuit card 1000 can interact with point-of-sale terminals that include magnetic stripe readers, short range transceivers, radio communication apparatuses, and the like. In addition, the EMV chip 1011 of universal integrated circuit card 1000 can be associated with a default credit or debit card. In this configuration, the universal integrated circuit card 1000 can be used with the default credit or debit card associated with the EMV chip 1011 at any terminal that requires an EMV chip and the universal integrated circuit card 1000 can be used to emulate any other card using the dynamic magnetic stripe 1021, a short range transceiver (not shown), a radio communication apparatus (not shown), or similar communication mechanism.

When a user orders or otherwise obtains a universal card 1000, the user can select or order a universal card 1000 that has an EMV chip 1011 associated with a particular default credit or debit card. The default credit or debit card associated with the EMV chip 1011 can be the same or different from a default card associated with the dynamic magnetic stripe 1021. For example, the user may have a VISA credit card that is the default card for the dynamic magnetic stripe 1021 and the same VISA credit card may be the default card associated with the EMV chip 1011. In this example, the user is accessing the same VISA credit card whether the transaction uses the EMV chip 1011 or whether the transaction uses the default card associated with the dynamic magnetic stripe 1021. In another example, the user may have a DISCOVER credit card that is the default card for the dynamic magnetic stripe 1021 and the user may have a MASTERCARD credit card that may be the default card associated with the EMV chip 1011. This example may be ideal for a user who lives in the United States and frequently wants to use the DISCOVER credit card for purchases at magnetic swipe terminals in the United States, but also frequently travels to Europe and wants to use the MASTERCARD credit card for purchases at EMV terminals in Europe. In either example, while the EMV chip may not be dynamically programmable, the universal integrated circuit card 1000 would still be programmable to emulate other cards, such as an AMERICAN EXPRESS credit card, using the dynamic magnetic stripe 1021, a short range transceiver, or a radio communication apparatus.

Figure 11A:
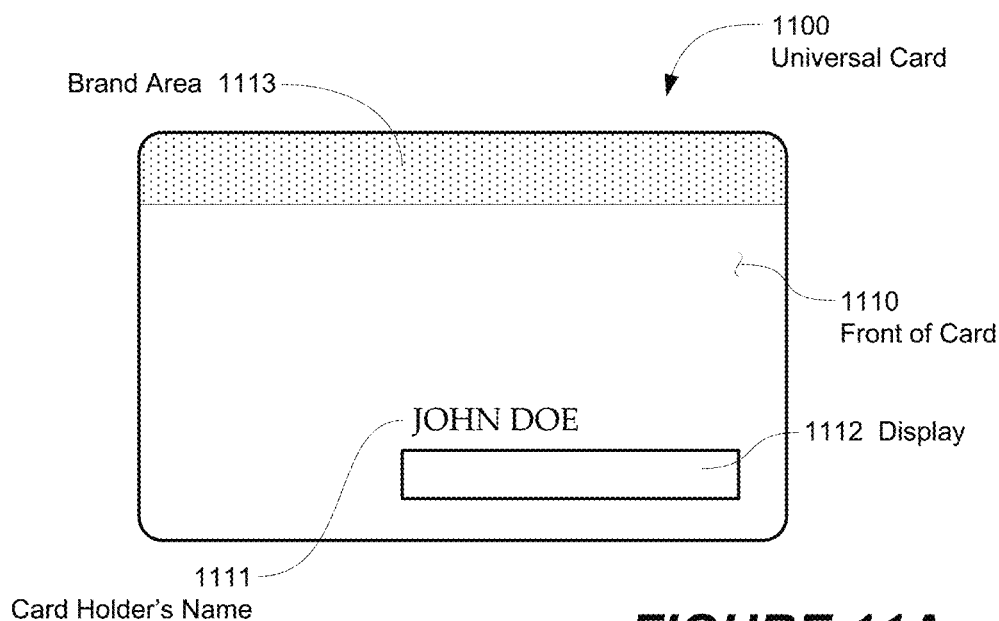
FIGS. 11A and 11B depict an embodiment of a universal card with a secure element.
Figure 11B:
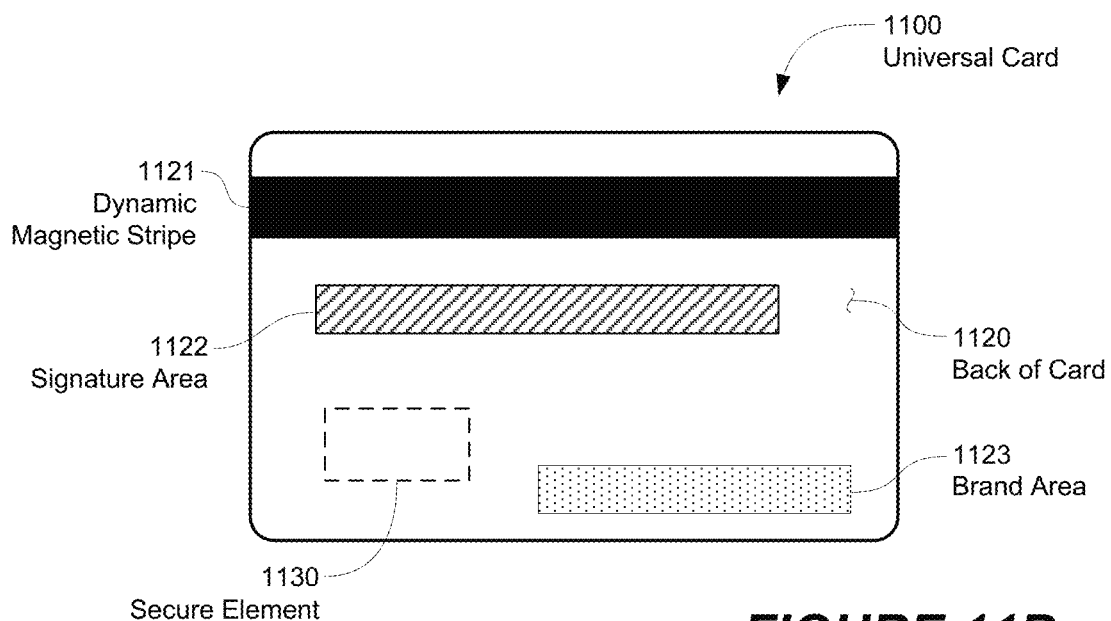

Referring now to FIGS. 11A and 11B, depicted is another embodiment of a universal card 1100. The universal card 1100 has a front 1110 that can optionally include a card holder's name 1111, a display 1112, and a brand area 1113. The universal card 1100 also has a back 1120 that can include a dynamic magnetic stripe 1121. The back of the card 1120 can also include features such as a signature area 1122 and a brand area 1123. The universal integrated circuit card 1100 can also include a secure element 1130, which can be located on the front, the back, or in the interior of universal integrated circuit card 1100.

A secure element 1130 is a tamper-proof smart card chip capable of embedding smart card grade applications, such as bank cards, credit cards, transportation cards, and the like, with the level of security required by financial institutions. Secure elements have been included in some computing devices, such as smart phones, as an independent part of the computing system which stores data associated with traditional cards and runs any software applications that use the traditional card data. Card issuers typically require this independent secure element to be in the computing device to ensure the security of the traditional card data and to protect against fraud. This requirement puts a limitation on developers and distributors of software application that use traditional card data because the ability to use such software applications is limited to computing devices which have secure elements. For example, a software developer may create a software application that runs in a cell phone operating system, such as the ANDROID operating system. The ANDROID operating system is available for use on a wide variety of cell phone models, only a few of which have secure element hardware. Thus, the software application will be limited to use on only those cell phone models that have a secure element and cannot be used on ANDROID cell phones that do not have a secure element.

In the embodiment depicted in FIGS. 11A and 11B, the universal card 1100 includes a secure element 1130 in the card. The universal card 1100 can communicate with any computing device, regardless of whether the computing device has a secure element. In the case where the universal card is in communication with a cell phone that does not have a secure element, the universal card 1100 can make secure element 1130 available for use by the cell phone. Thus, a user will be able to use software applications on the cell phone that require a secure element by utilizing the secure element 1130 of the universal card 1100 while the cell phone is in communication with the universal card 1100. Furthermore, the user can enter traditional card information into the cell phone while the cell phone is in communication with the universal card 1100, the traditional card data can be communicated to the secure element 1130 of the universal card 1100 for storage, and the cell phone can later access the traditional card data in the secure element 1130 of the universal card 1100 in the same or a later communication session. Including a secure element 1130 in universal card 1100 solves the issues associated with computing devices that do not have a secure element. In addition, including a secure element 1130 in universal card 1100 allows banks and card issuers to have greater control of the use of secure elements. Currently, when mobile device manufacturers include secure elements in mobile devices, banks and card issuers must negotiate with the manufacturers to be able to have access to and use of the secure element. However, moving the secure element to a universal card 1100 which is under control of the bank or card issuer eliminates the need for the bank to negotiate with the manufacturer of a mobile device to have access to a secure element regardless of whether the mobile device also has a secure element.

Figure 12A:
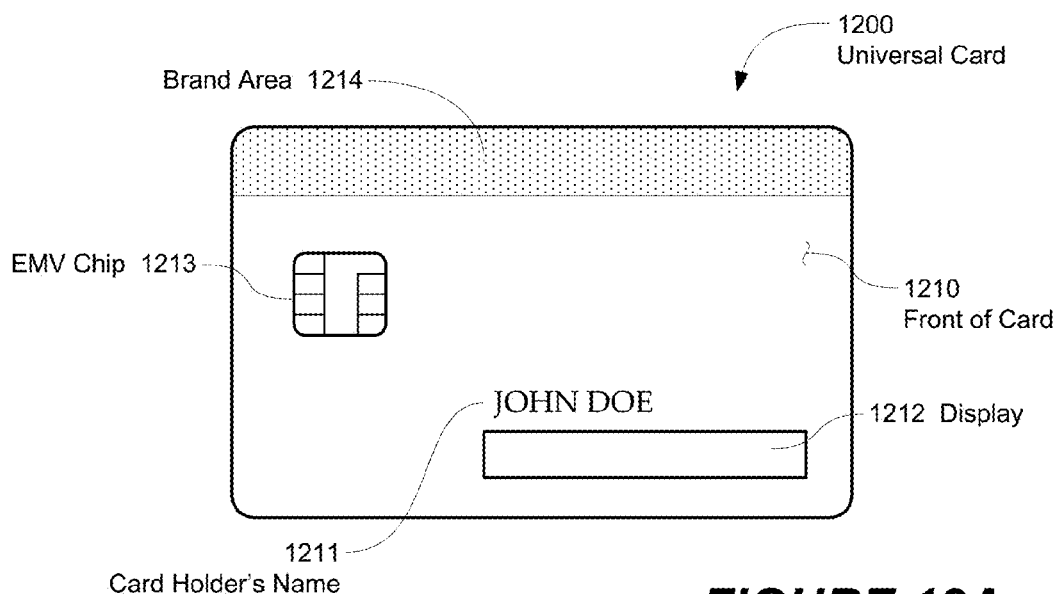
FIGS. 12A and 12B depict an embodiment of a universal card with an integrated circuit and a secure element.
Figure 12B:
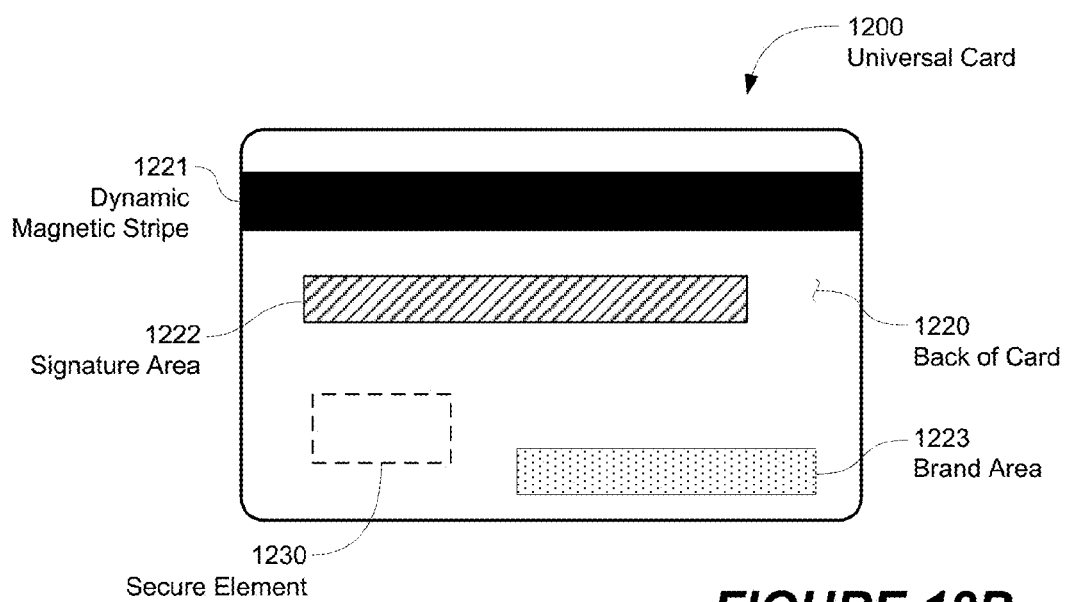

Referring now to FIGS. 12A and 12B, depicted is another embodiment of a universal card 1200 having a secure element and an EMV chip. The universal card 1200 has a front 1210 that can optionally include a card holder's name 1211, a display 1212, and EMV chip 1213, and a brand area 1214. The universal card 1200 also has a back 1220 that can include a dynamic magnetic stripe 1221. The back of the card 1220 can also include features such as a signature area 1222 and a brand area 1223. The universal integrated circuit card 1200 can also include a secure element 1230.

Figure 13:
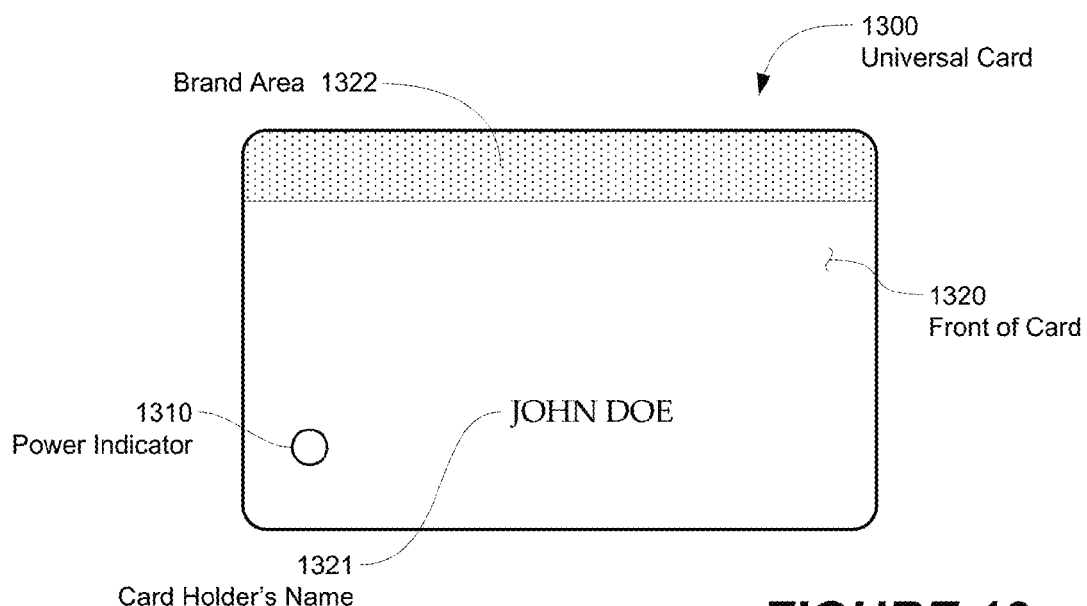
FIG. 13 depicts an embodiment of a universal card with a power indicator.

Referring now to FIG. 13, depicted is an embodiment of a universal card 1300 with a power indicator 1310. The power indicator 1310 indicates to the user that the universal card 1300 is ready to be used in a transaction. The power indicator 1310 can indicate that the universal card 1300 can be used with either or both of a magnetic stripe reader and a contactless payment terminal. The power indicator 1310 can be any visual indicator, such as an LED light, a color indicator, and the like. In the embodiment of an LED light, the LED light can be illuminated when the card is active (i.e., ready to emulate a traditional card as either or both of a magnetic swipe card or a contactless payment card) and the LED light can be off when the card is inactive. A power indicator 1310 on universal card 1300 can replace the need for the universal card 1310 to have a display, thereby reducing the overall cost to make and sell the universal card 1310. As depicted in FIG. 13, the power indicator 1310 can be located on a front 1320 of universal card 1300. Optionally, the front 1320 of universal card 1300 can also include the card holder's name 1321 and a brand area 1322. In another embodiment not depicted in FIG. 13, a power indicator can be located on a back of universal card 1300.

One benefit associated with the use of a power indicator 1310 is that a card holder will know that the card is active when attempting to use the card. As discussed above, a universal card can be programmed to emulate a default card unless programmed otherwise by the card holder. In this situation, the card holder may assume that the universal card can be used at any moment as the default card. However, the universal card may be programmed to be inactive when not in use in order to conserve battery power. If the universal card is inactive and there is no power indicator, the card holder may assume that an inactive card is always active and attempt to use the inactive universal card as the default card. Having a power indicator 1310 on the universal card 1300 allows the user to easily determine whether the universal card 1300 is active and ready for use.

Figure 14:
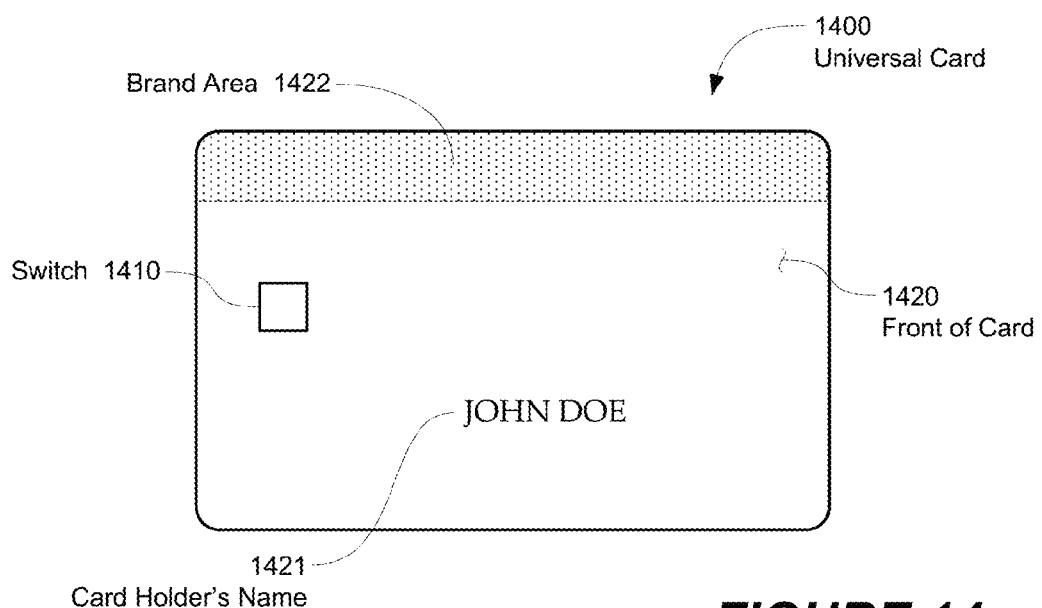
FIG. 14 depicts an embodiment of a universal card with an activation switch.

Referring now to FIG. 14, depicted is an embodiment of a universal card 1400 with a switch 1410. The switch 1410 enables the user to activate or deactivate the universal card 1400. Having a switch 1410 on the universal card 1400 eliminates the need for the user to interact with a mobile device in communication with the universal card 1400 to activate the universal card 1400. For example, the universal card 1400 may be programmed to emulate a default card unless programmed otherwise by the card holder. If the card holder simply wants to use the universal card 1400 to emulate the default card, the card holder can activate the universal card 1400 using the switch 1410 and not have to use a mobile device in communication with the universal card 1400 to activate the universal card 1400. The switch can be especially useful if the user's mobile device is out of battery power or otherwise malfunctioning. When the universal card 1400 is activated using the switch 1410, the universal card 1400 can retrieve the information for the default card from a secure element in universal card 1400. Thus, no exchange of information between a mobile device and universal card 1400 is necessary to activate universal card 1400 to be the default card using the switch 1410.

A bank or card issuer of a universal card may take advantage of the default card feature of the universal card. The bank or card issuer may require the consumer to download and use its e-wallet software application to interface with the universal card. That e-wallet software may require that the default card of the universal card is a default card which is issued by the bank or card issuer. For example, if a bank issues the universal card and requires the consumer to download the bank's e-wallet software, the bank's e-wallet software may allow the consumer to select only one of the bank's cards, such as a debit card associated with the bank or a credit card associated with the bank, as the default card. In this scenario, each of the default cards associated with the universal card, including a default card for an EMV chip, a default card for a dynamic magnetic stripe, and a default card for contactless payment, may be a card associated with the bank. Arranging for all of the default cards to be associated with the bank is a valuable position for the bank because the easiest way for the consumer to use the universal card is by using the universal card as one of the default cards without using a mobile device to change the universal card to a non-default card.

The switch 1410 can take any number of forms. As depicted in FIG. 14, the switch 1410 could be a button on the exterior of universal card 1400, such as on a front 1420 of universal card 1400. Optionally, the front 1420 of universal card 1400 can also include the card holder's name 1421 and a brand area 1422. In another embodiment not depicted in FIG. 14, a switch can be located on a back of universal card 1400. In addition, the universal card 1400 could include both a switch 1410 and a power indicator (not shown in FIG. 14). This combination would allow the card holder to activate the universal card 1400 using the switch 1410 and visually see that the universal card 1400 has been activated. In another form of the switch not depicted in FIG. 14, the switch 1410 could be snap switch on the interior of the card. A snap switch can detect bending and/or tapping of the universal card 1400. Using a snap switch, in order for the card holder to activate the card, the card holder would slightly bend and/or tap the card until the universal card is active. In the embodiment of a snap switch, a power indicator on the card may be particularly helpful so that the card hold knows when the card has been sufficiently bent and/or tapped to trigger the snap switch.

Figure 15A:
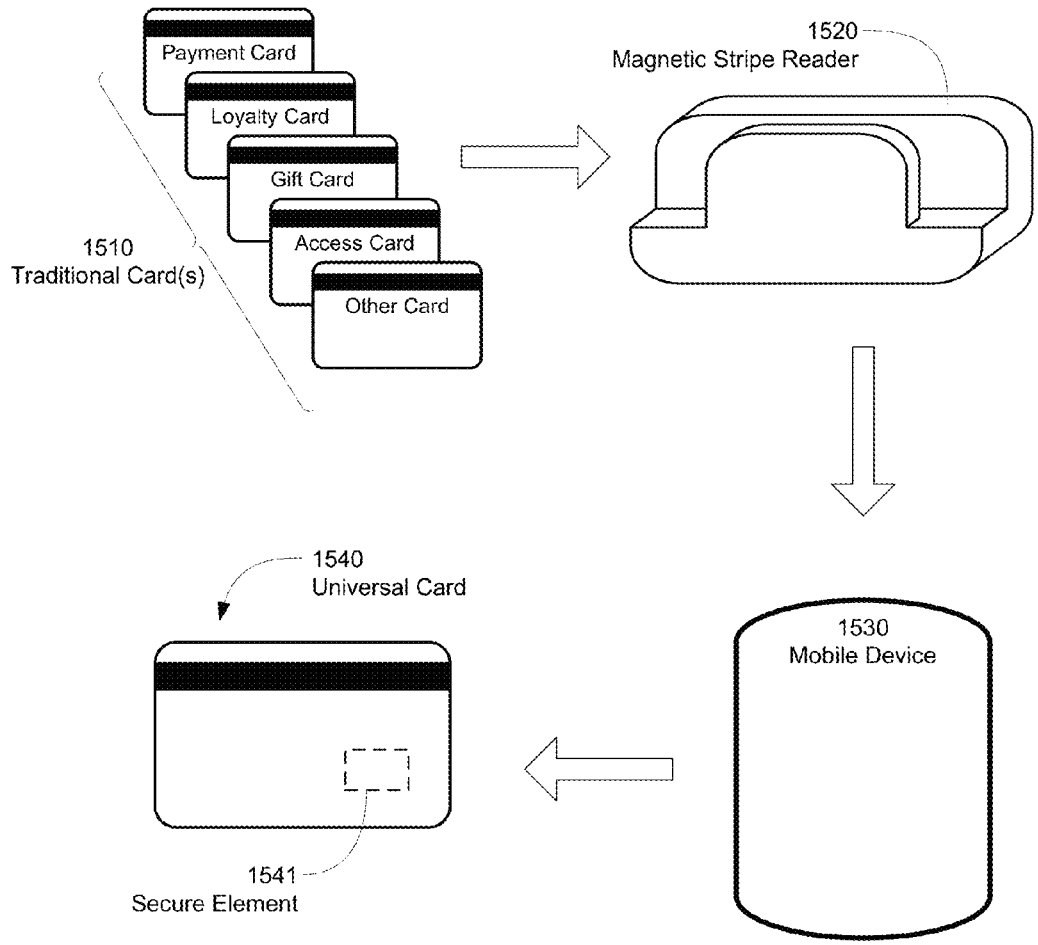
FIGS. 15A and 15B depict ways to add traditional card data to a secure element of a universal card.
Figure 15B:
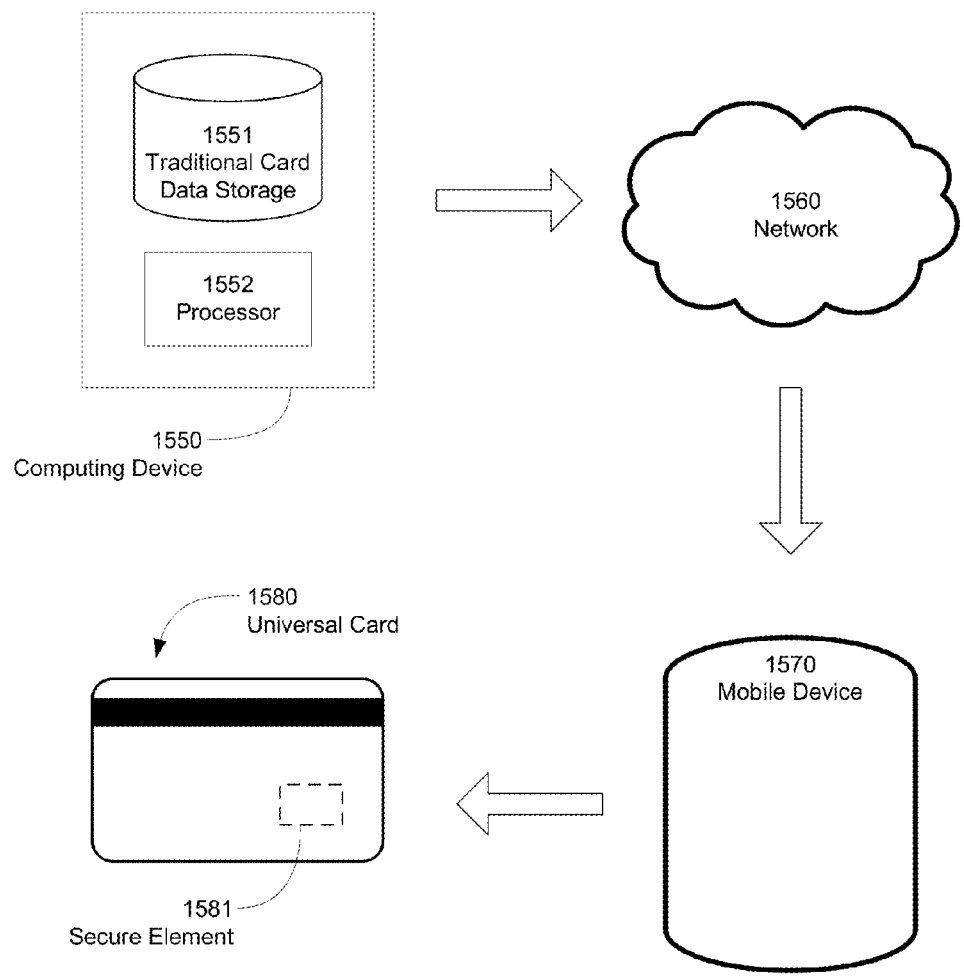

Referring now to FIGS. 15A and 15B, depicted are ways to add traditional card data to a secure element of a universal card. As shown in FIG. 15A, a card holder can have one or more traditional cards 1510. The user can swipe the one or more traditional cards 1510 through a magnetic stripe reader 1520 which reads the traditional card data from the swiped magnetic stripe. The magnetic stripe reader 1520 is connected to a mobile device 1530 which is configured to receive the traditional card data from the magnetic stripe reader 1520. The connection between the magnetic stripe reader 1520 and the mobile device 1530 may be a wired connection or wireless connection. The mobile device 1530 can be connected to a universal card 1540 which has a secure element 1541 via a short range communication link. The mobile device 1530 is configured to transmit the traditional card data received from the magnetic stripe reader 1520 to the universal card 1540 without storing the traditional card data, and the universal card 1540 is configured to store the traditional card data in the secure element 1541. In one embodiment of the connection between the magnetic stripe reader 1520 and the mobile device 1530, the magnetic stripe reader 1520 has a headphone connector which is configured to connect to a headphone port of the mobile device 1530, and the mobile device 1530 is configured to receive the traditional card data from the magnetic stripe reader 1520 via the headphone port.

As shown in FIG. 15B, a computing device 1550 can store traditional card data in storage 1551. The computing device 1550 can also have a processor 1552 and other computing hardware and/or software. The computing device 1550 can be controlled and secured by a bank, by a traditional card issuer, or by another entity. The computing device 1550 is connected to a mobile device 1570 via a network 1560. The network 1560 can be a wired network, a wireless network, or any combination of wired and wireless networks, including one or more of the internet, a cellular phone network, a wi-fi network, a local area network, a wide area network, and the like. The mobile device 1570 is configured to receive the traditional card data from the computing device 1550 via the network 1560. The computing device may encrypt the traditional card data prior to transmission via the network 1560. The mobile device 1570 can be connected to a universal card 1580 which has a secure element 1581 via a short range communication link. The mobile device 1570 is configured to transmit the traditional card data received from the computing device 1550 to the universal card 1580 without storing the traditional card data, and the universal card 1580 is configured to store the traditional card data in the secure element 1581.

Another way that a secure element of a universal card can be loaded with traditional card data is by the card issuer pre-loading the traditional card data on the secure element before the card is given to the consumer. The card issuer may have information about some or all of the consumer's traditional cards and can pre-load the secure element of a card with the traditional card data. In one example, the card issuer may be a bank and the consumer may have a debit card associated with the bank and a credit card associated with the bank. The bank may pre-load into the secure element of a universal card traditional card data corresponding to each of the debit card and the credit card before sending the universal card to the consumer. When the consumer receives the card, the universal card will already be configurable to emulate the debit card and the credit card. In one embodiment, the bank may also designate one of the debit card and the credit card as the default card for the universal card before sending the universal card to the consumer. In this embodiment, the universal card may be immediately available to the consumer for use as the default card without having to interface the universal card with a mobile device. Setting the default card to a traditional card associated with the bank gives the bank the valued position of having its traditional card be the easiest way for the consumer to use the universal card.

Figure 15C:
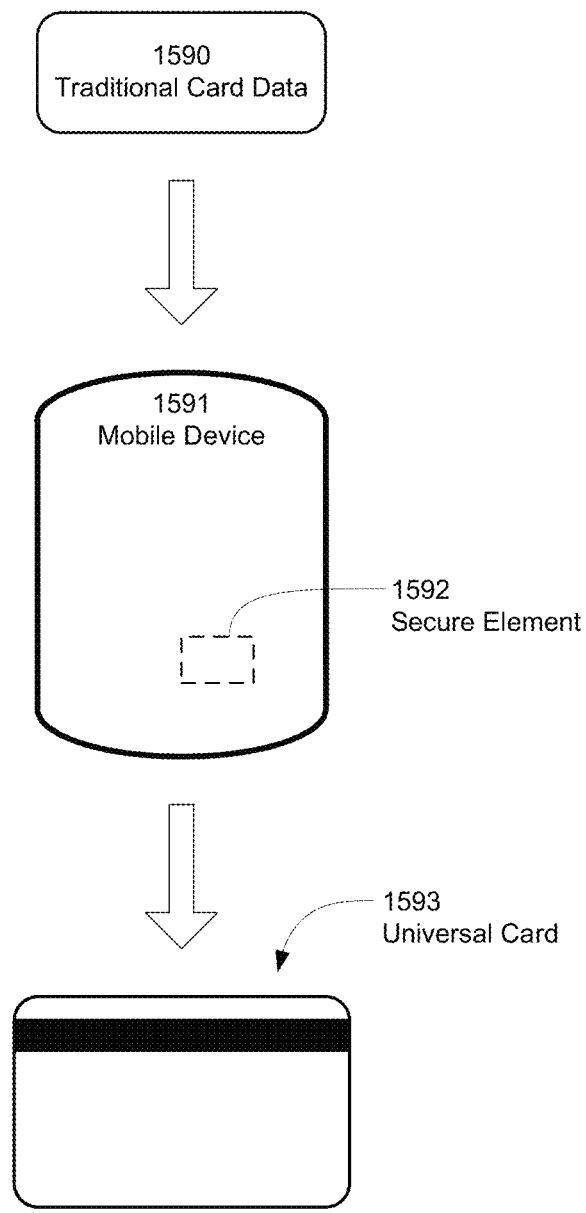
FIG. 15C depicts a way to add traditional card data to a secure element of a mobile device.

Referring now to FIG. 15C, depicted is a way to use a universal card with a mobile device that includes a secure element. Traditional card data 1590 can be communicated to a mobile device 1591. The traditional card data 1590 can be communicated by swiping traditional card through a magnetic stripe reader which communicates the traditional card data to mobile device 1591, similar to the depiction in FIG. 15A, or traditional card data 1590 can be communicated from a computing device to mobile device 1591 via a network, similar to the depiction in FIG. 15B. Mobile device 1591 can include a secure element 1592 which is configured to securely and independently store the traditional card data. The mobile device 1591 can be configured to send instructions to a universal card 1593 to program the universal card 1593 to emulate a traditional card. The instructions sent from the mobile device 1591 to the universal card 1593 can include confidential traditional card data from the secure element 1592 which is necessary for the universal card 1593 to emulate the traditional card. The instructions sent from the mobile device 1591 to the universal card 1593 can include instructions for the universal card to emulate either or both of a magnetic stripe of the traditional card and a contactless payment form of the traditional card.

Referring back to FIG. 1, a mobile device 100 can be configured to communicate with a universal card 110 that has a secure element 119 via a short range communication link 120. As described above, a secure element 119 is an independent part of the universal card 110 which stores data associated with traditional cards and maintains that traditional card data securely. The mobile device 100 can include e-wallet software 105 that provides a user interface which allows a user to program the universal card 110. In one embodiment, the secure element 119 of the universal card 110 stores confidential traditional card data associated with a VISA credit card and a DISCOVER credit card. The confidential traditional card data in the secure element 119 can include any information necessary to emulate the VISA credit card and the DISCOVER credit card, such as an account number, a card number, a card holder's name, an expiration date, a card verification value 2 (CVV2), information stored on the magnetic stripe of the traditional cards, and any other required information. The e-wallet software 105 may not store the confidential traditional card data because banking requirements may not permit the confidential traditional card data to be stored on the mobile device 100. However, the mobile device 100 may store non-confidential data for each of the traditional cards. For example, the mobile device 100 may store a nickname associated with each traditional card, the last 4 digits of the traditional card number, an image associated with the issuer of each traditional card, and so forth. By storing non-confidential traditional card data in mobile device 100, the e-wallet software 105 can permit the user to select which traditional card the universal card 110 shown emulate by displaying some or all of the non-confidential traditional card data. For example, the e-wallet software 105 may display two buttons respectively labeled as "VISA **   1234" and "DISCOVER    9876." The user can select either of the two traditional credit card options. In response, the mobile device 100 sends a signal to universal card 110 indicating that the universal card should emulate the selected traditional credit card. In one embodiment, the universal card 110 configures both the dynamic magnetic stripe 111 to emulate the magnetic stripe of the selected traditional credit card and the short range transceiver 116 to emulate the selected traditional credit with a contactless payment terminal. In this manner, the user needs only to select the desired traditional card using the e-wallet software 105**, without having to make a selection of magnetic stripe or contactless payment, and the user can use the traditional card with either a magnetic swipe terminal or a contactless payment terminal.

When the universal card 110 is in communication with the mobile device 110, the universal card 110 may send notifications back to mobile device 100. For example, if a battery in universal card 110 is low, the universal card 110 can send a low battery signal to the mobile device 100. The mobile device 100 or the e-wallet software 105 can be configured to display a warning message to the user. The mobile device 100 or the e-wallet software 105 can also be configured to communicate to the issuer of the universal card 110 that the universal card 110 needs to be replaced. In another example of a notification, a VISA card may have been selected as a default card for the universal card 110, but the user may have programmed the universal card 110 to emulate a DISCOVER card for a three-hour period and then revert back to the default VISA card. This situation may occur when the user is planning to spend several hours at a shopping mall and wants to use the DISCOVER card while at the mall. At or near the end of the three-hour period, the universal card 110 may send a signal to the mobile device that the universal card 110 is about to revert back to the default VISA card. The mobile device 100 or the e-wallet software 105 can be configured to display a warning message or sound and alarm to the user so that the user is aware of the reversion back to the VISA card.

One issue with using a mobile device 100 to interface with a universal card 110, and any confidential data stored in a secured element of the universal card, is the need for authentication. Several forms of authentication are discussed above. Authentication may also vary based on the configuration of the mobile device 100. For example, a mobile device 100 may be secured such that a user of the mobile device must be authenticated each time the user unlocks the mobile device 100. In this case, the e-wallet software 105 may recognize that the user has already been authenticated when the mobile device 100 was unlocked, and the e-wallet software 105 may not need to require authentication when the user initially interfaces with the e-wallet software 105. In another example, a user may be able to unlock the mobile device 100 without any authentication. In this case, any person may be able to unlock the device and start the e-wallet software 105. Here, the e-wallet software 105 may recognize that the user has not been authenticated when the mobile device 100 was unlocked, and the e-wallet software 105 may require the user to be authenticated when the user initially interfaces with the e-wallet software 105.

The issuer of the universal card 110 may have interest in making the universal card 110 available for interacting with e-wallet software created by other individuals or entities. In order to allow such third-party software to be created, the issuer may create an application programming interface (API) or software developer kit (SDK) which provides a framework of rules and specifications for interacting with the universal card 110. The API or SDK can be provided to third party software developers to enable them to create e-wallet software applications that successfully interact with the universal card 110.

The dynamic magnetic stripe 111 of universal card 110 may be used in a number of ways that are not available to static magnetic stripe cards. As discussed above, magnetic stripe cards have three standard track layouts: Track 1, Track 2, and Track 3. Various implementations of magnetic stripes have standard fields in certain tracks while leaving other portions of tracks available for other uses. Having a dynamic magnetic stripe 111 in a universal card 110 allows the non-standardized portions of the tracks to communicate data to a terminal that cannot be communicated by a static magnetic stripe of a traditional card. In one embodiment, a card holder may want to pay with a credit card and use one or more coupons in the same transaction. In a traditional setting, the card holder would present physical coupons to a cashier, the cashier would enter the coupons, and the card holder's traditional card would be swiped for payment. In contrast, an e-wallet application 105 can manage digital coupons for a user. Using the mobile device 100 and e-wallet application 105, the user can select one or more coupons to be used in a transaction, and a corresponding signal can be communicated to the universal card 110. The signal can also include an indication of a traditional card for the universal card 110 to emulate. When universal card 110 configures the dynamic stripe 111 to emulate a traditional card magnetic stripe, the universal card 110 can also include the coupon information in one of the non-standardized portions of the tracks. The universal card 110 can be swiped in a magnetic stripe reader which is configured to identify the data in the non-standardized portions of the tracks. The magnetic stripe reader may apply the coupon to the transaction prior to charging the transaction to the account associated with the traditional card emulated by the universal card 110.

Another example of using the non-standardized portions of the tracks includes using a dynamic authentication value to authenticate the transaction. To prevent fraudulent transactions, traditional contactless cards can generate dynamic data every time they are read. Dynamic data generation per read provides logical security and inhibits fraudulent replay of contactless card data that may have been previously read. For example, contactless credit, debit and prepaid payment card data includes a dynamic card verification number, sometimes referred to "CVC," "CVV," or "dynamic CVV," or transaction certificate (for EMV cards). The dynamic authentication value is unique for every transaction. One way of the dynamic authentication value to be generated is using a secret key stored in secured memory of the card, a random number, a transaction counter, and a specific algorithm. Other ways of generating the dynamic authentication value are possible. The dynamic authentication value is generated dynamically every time a traditional contactless card is read for a transaction and the dynamic authentication value can be authenticated by a payment terminal contacting the issuer of the card to verify the dynamic authentication value. However, dynamic authentication values cannot be used with traditional static magnetic stripe cards because the static magnetic stripe cannot produce a unique dynamic authentication value each time the magnetic stripe is swiped for a transaction. The use of a dynamic magnetic stripe 111 in universal card 110 allows a dynamic authentication value unique to each transaction to be written to the non-standardized portions of the tracks. In this manner, a universal card 110 can generate a dynamic authentication value in the same manner as traditional contactless cards and write the generated dynamic authentication value to one of the non-standardized portions of the tracks. The universal card 110 can be swiped in a magnetic stripe reader which is configured to identify the dynamic authentication value in the non-standardized portions of the tracks and authenticate the transaction with the card issuer. In another embodiment, the traditional card may have a field on the static magnetic stripe for a CVV value. When the universal card is configured to emulate the traditional card that normally has a static CVV value field, the universal card may generate a dynamic authentication value and write the dynamic authentication value in the field typically used for the static CVV value. The dynamic authentication value could have the same format as the static CVV and be located in the same location that the static CVV field would be located in the static magnetic stripe of the traditional card. In this scenario, there would be no need to reconfigure the terminal with the magnetic stripe reader because it would already be configured to read a value from the static CVV field location. Using dynamic authentication values with traditional magnetic stripe reader terminals allows for the added security of the dynamic authentication value authentication without requiring terminals to add a contactless payment terminal to the magnetic stripe reader.

When the universal card can be configured to emulate multiple traditional cards, some of issuers of the traditional cards will be capable of authenticating a dynamic authentication value while others of the issuers of the traditional cards will only be capable of authenticating a static authentication value. The secure element may store with the traditional card data, an indication as to whether a static authentication value or a dynamic authentication value should be used when emulating each traditional card.

A universal card can also be used to eliminate the need for physical traditional cards altogether. Traditional cards are currently being used as pre-paid cards in place of cash in a number of settings. Many credit issuing companies, such as VISA, MASTERCARD, and AMERICAN EXPRESS, offer pre-paid debit cards which require that the amount of the debit card be pre-paid, or "loaded," before the card can be used in a financial transaction. Some pre-paid debit cards permit users to pay up the available amount on the card, or "reload" the card. These pre-paid debit cards can be used by consumers who have bad credit but still want the ease of using a magnetic swipe card in transactions, by government agencies to provide government benefits such as social security benefits and unemployment benefits, by employers as bonuses or incentives to employees, and by consumers that give them as gifts. Traditional cards are also being used as gift cards which are typically usable only at a single retailer or group of retailers. Gift cards typically must be pre-paid. Consumers that buy gift cards must either go to a retail location to buy the physical gift card or they can purchase gift cards online and have the physical gift card shipped. Some retail locations, such as grocery stores, offer for purchase gift cards to a wide variety of other retail locations. This offers a consumer the convenience of purchasing gift cards for a number of different retailers while only physically visiting a single store to obtain the physical gift cards. Traditional cards are also being used as loyalty cards and membership cards for certain retail locations. Many retailers, such as grocery stores, allow consumers to obtain free loyalty cards which can be presented when the consumer is checking out to obtain sale prices of certain items. Other retailers, such as warehouse stores, offer paid memberships which include a membership card that must be presented each time the consumer is entering the store and/or checking out.

The proliferation of uses for traditional cards has flooded consumers with the number of traditional cards they may need to carry. For example, a consumer may carry several credit cards, a debit card, several gift cards, a membership card, and several loyalty cards. Having to carry so many cards may reduce the likelihood that a consumer would sign up for an additional card. For example, if a consumer is at a store that offers a loyalty card, the consumer may decline the loyalty card because the consumer does not want to carry around an additional card, to remember where that card is stored in a purse or wallet during a subsequent visit to the store, and the like. Additionally, having a large number of cards increases the likelihood that a card will be misplaced, lost, or stolen. A consumer is much less likely to purchase a pre-paid card, such as a pre-paid debit card, a gift card, and the like, if the entire value of the card is lost when the card is lost, misplaced, or stolen.

Attempts have been made to eliminate the need for physical traditional cards. Services have been developed which allow consumers to make online purchases of digital gift certificates. The digital gift certificate is typically sent to the recipient in a printable form. The recipient must print out the gift certificate and take the physical printout to the retail location to use the gift certificate. The printed gift certificate typically includes a bar code or other code which the retail location can verify before accepting the printed gift certificate as payment. While this system eliminates a physical card, it still requires the consumer to carry a printout to the retail location. Additionally, loss or theft of the printout can result is loss of the value of the gift certificate if the lost or stolen printout is used by another person.

Figure 16:
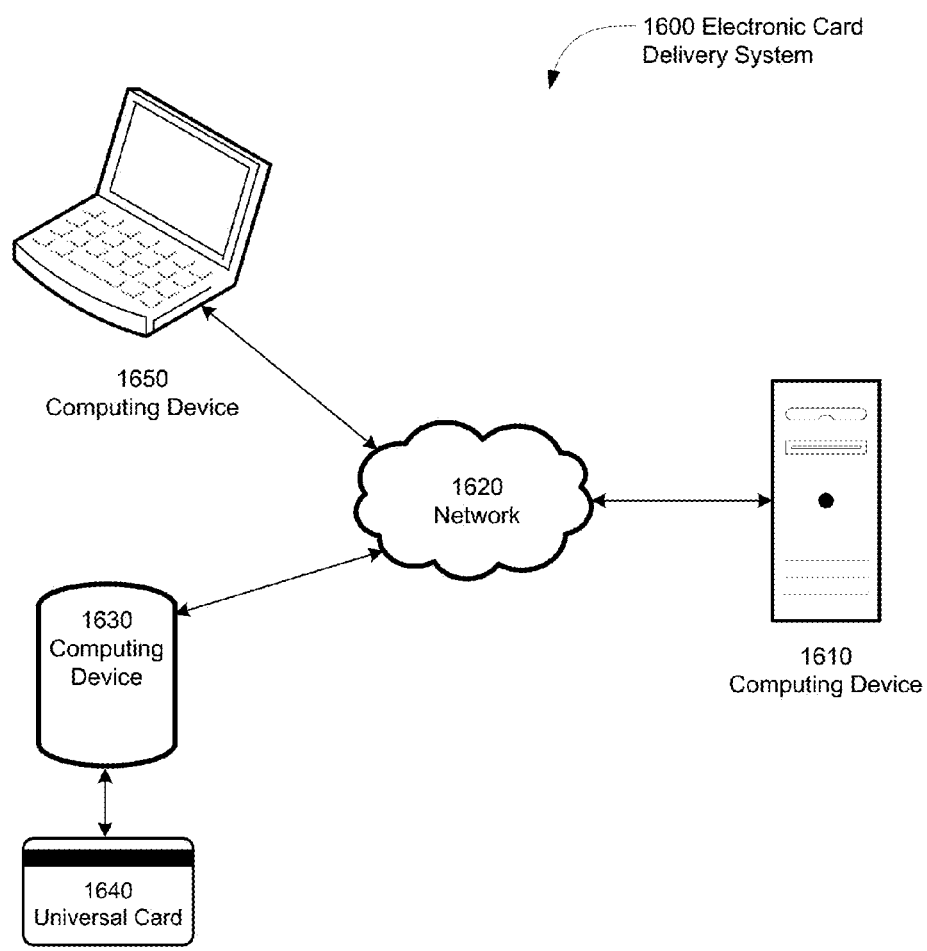
FIG. 16 depicts an exemplary electronic card data delivery system.

Referring now to FIG. 16, depicted is an electronic card data delivery system 1600. Computing device 1610 can be associated with an operator which distributes pre-paid cards, loyalty cards, or any other type of card. The computing device 1610 is connected, via a network 1620, to a computing device 1630. Computing device 1630 is associated with a universal card 1640. A user can contact the operator of computing device 1610 and request that card data be sent to computing device 1630 for use by universal card 1640. For example, the user can request that a $100 gift card be sent to computing device 1630. In response to receiving the request, computing device 1610 can create a gift card account credited with $100 and deliver, via network 1620, card data to computing device 1630. The gift card data can be used to program universal card 1640 to emulate a traditional card associated with the gift card account. In another example, the user can request a loyalty card account and computing device 1610 can deliver, via network 1620, card data to computing device 1630. The loyalty card data can be used to program universal card 1640 to emulate a traditional card associated with the loyalty card account.

Electronic delivery of card data from computing device 1610 to computing device 1630 can take a number of forms. In one example, the user requesting delivery of the card data may identify computing device 1630 and the computing device 1610 may automatically send the card data to computing device 1630. In another example, when requesting delivery of the card data, the requester may give identification information of the recipient. The identification information may include a cell phone number of the recipient, an email address of the recipient, or any other information identifying the recipient. The computing device 1610 can send a message to the recipient by email, by text message, or by any other communication method. The message can include an indication to the recipient that card data is available for download and instructions on how the recipient can download the card data. When the recipient follows the download instructions, computing device 1630 is identified by computing device 1610 and the card data is delivered from computing device 1610 to computing device 1630. In yet another example, the delivery of card data can take place via a social network. The requester may indicate a user name or other identifier of a contact in a social network as the recipient. A message can be sent to the recipient via the social network or post a message on a page associated with the recipient. The message can include an indication to the recipient that card data is available for download and instructions on how the recipient can download the card data. When the recipient follows the download instructions, computing device 1630 is identified by computing device 1610 and the card data is delivered from computing device 1610 to computing device 1630. Any number of other examples of delivering data from computing device 1610 to computing device 1630 are possible.

Either or both of computing device 1630 and universal card 1640 can include a secure element. When computing device 1630 receives card data from the computing device 1610, it can store the card data in either a secure element of the computing device 1630, in a secure element of universal card 1640, or in secure elements of both the computing device 1630 and the universal card 1640. Once the card data is stored in a secure element, the universal card 1640 can be programmed to emulate a physical traditional card associated with the card data. It is also possible for card data to be stored in memory that is not part of a secure element. It may be advantageous to store card data associated with non-financial cards, such as loyalty cards, in memory that is outside of the secure element. Doing so may preserve limited memory capabilities of a secure element, leaving memory available in the secure element to store card data which cannot be stored outside of the secure element, such as bank card data.

The request for card data may be sent from computing device 1630. In this embodiment, a user of computing device 1630 can request card data be sent to the user's own computing device 1630. Computing device 1630 can be a cell phone, a PDA, an iPod, a tablet computer, a laptop computer, a desktop computer, an NFC-specialized device, or any other type of computing device. For example, the user may wish to add a loyalty card to the list of possible cards that the universal card 1640 can emulate. In this case, the user can contact the loyalty card issuer using computing device 1630. Computing device 1630 can include any one of the following features which would allow the user to request card data: an e-wallet application, a card requesting application that is specifically dedicated to allowing users to request various types of card data, a retailer application that allows the user to request card data for that particular retailer, and a web browser that allows the user to access a website which allows the user to request card data. In one embodiment, the user of computing device 1630 may use an e-wallet application to request new card data. In this embodiment, the user could purchase a gift card using the e-wallet application on computing device 1630 and the remote computer 1620 could receive the request, process the purchase, and send card data for the gift card back to computing device 1630. Using the e-wallet application to purchase the gift card allows the user to select any of the cards already stored in the e-wallet application to use for purchasing the gift card. Other methods and applications are available to allow a user to request card data.

The request for card data may be sent from a computing device 1650 that is different from computing device 1630. In this embodiment, the requesting user may use any computing device 1650 which is capable of communicating a request for card data to computing device 1610. Computing device 1650 can be a cell phone, a PDA, an iPod, a tablet computer, a laptop computer, a desktop computer, an NFC-specialized device, or any other type of computing device. For example, the requesting user may wish to send a gift card to the user of computing device 1630 in electronic format so that the recipient can use the universal card 1640 to emulate the gift card. In this case, the requesting user can contact the gift card issuer using computing device 1650. In yet another example, a user can use one computing device 1650, such as a laptop computer or desktop computer, to request that card data be sent to the user's own computing device 1630, such as the user's tablet computer. Computing device 1650 can include any one of the following features which would allow the user to request card data: an e-wallet application, a card requesting application that is specifically dedicated to allowing users to request various types of card data, a retailer application that allows the user to request card data for that particular retailer, and a web browser that allows the user to access a website which allows the user to request card data.

The operator of computing device 1610 can be any number of entities. In one example, the operator of computing device 1610 can be a retailer. The retailer may operate a website through which a user can purchase products and gift cards specific to the retailer. The retailer may allow a user to purchase a gift card with delivery being in electronic form to the computing device 1630. In this case, no physical card would be sent to the requester and/or the recipient; instead, card data would be delivered from computing device 1610 to computing device 1630 and the recipient would be able to program universal card 1640 to emulate a physical gift card. In another example, the operator of computing device 1610 can be a retailer which offers loyalty cards and/or membership cards. The retailer may allow a user to request a loyalty card or purchase a membership card with delivery being in electronic form to the computing device 1630. In this case, no physical loyalty card or membership card would be sent to the recipient because the universal card 1640 would be able to emulate a loyalty card or membership card. In another example, the operator of computing device 1610 can be a card issuer. A card issuer may allow a user to apply for a credit card. Upon approval of the credit card, the computing device 1610 can send card data to the computing device 1630 and the recipient would be able to program universal card 1640 to emulate a physical credit card. In yet another example, the operator of computing device 1610 can be a card issuer which allows users to purchase pre-paid debit cards. The card issuer may allow a user to purchase a pre-paid gift card with delivery being in electronic form to the computing device 1630. In this case, no physical pre-paid debit card would be sent to the recipient; instead, card data would be delivered from computing device 1610 to computing device 1630 and the recipient would be able to program universal card 1640 to emulate a pre-paid debit card.

In the pre-paid debit card example, the ability to request and have pre-paid debit card data delivered to a recipient electronically could obviate the need for money wiring services. In one embodiment, a parent of a college student may wish to send money to the college student. Instead of using a money wiring service, the parent may use a computing device 1650 to contact a pre-paid debit card issuer and request that a pre-paid debit card be electronically delivered to the college student's computing device 1630. Upon approval of the pre-paid debit card, the computing device 1610 can electronically deliver card data associated with the pre-paid debit card to the college student's computing device 1630. Once the card data has been electronically delivered to computing device 1630, the college student can use the pre-paid debit card by programming the universal card 1640 to emulate the pre-paid debit card. In this example, the parent was able to make money available to the college student without having to use a money wiring service and without having to ship a physical card to the college student.

The ability to send card data electronically can also improve customer loyalty reward systems. Some retailers reward customers for making purchases with loyalty cards in the form of gift cards, gift certificates, electronic gift certificates, and the like. Examples include retailers that send a gift card to customers once the customers reach some spending threshold and retailers that send electronic gift certificates to customers each month based on the amount customers have spent during the month. These systems require either that a physical gift card or gift certificate be sent to customers, or that customers print electronic gift certificates and physically bring the printed gift certificate to the retail location. Instead, if a customer has a universal card, the customer may be able to choose to receive all benefits in the form of electronic card data. In the example where a retailer normally provides a gift card once a customer reaches some spending threshold, the retailer could send gift card data to the customer's computing device for use with the customer's universal card. Similarly, in the example where a retailer normally provides an electronic gift certificate to a customer each month based on the amount the customer has spent during the month, the retailer could send gift card data to the customer's computing device for use with the customer's universal card. In another embodiment, the retailer may be aware that the customer already has both loyalty card data for that retailer and gift card data for that retailer available for use with the universal card. In this embodiment, when the retailer is due to send a gift card or a gift certificate to the customer, the retailer may instead credit the gift card account for which the user already has the gift card data and notify the customer that the gift card account has been credited with a certain amount.

The ability to send card data electronically without having a physical card can also reduce card fraud. One way in which fraud occurs is when a thief goes to a retail location where gift cards or other cards on displayed on shelves and records the information from not-yet-activated card, sometimes referred to as "skimming." The information can include a card number, a security or access code, and the like which are sometimes concealed by cardboard or a scratch off film. The thief monitors the card status online using the card information. Once the thief finds that the card has been activated, the thief depletes the value of the card before it is used. For example, with a gift card associated with a retailer, once the gift card has been activated, the thief can go to a website of the retailer and make a purchase using the gift card information. Skimming is eliminated if card data is sent electronically to a recipient and not available for inspection in physical form.

The above description of FIG. 16 refers to computing device 1610 as a single computing device. While computing device 1610 can be a single computer, it is important to note that computing device 1610 can include multiple computing devices, such as a number of servers, multiple data centers, and the like. Computing device 1610 can also be a point of sale terminal or terminals. In this embodiment, a point of sale terminal 1610 can send card data to a computing device 1630. The gift card data can be transmitted from point of sale terminal 1610 to computing device 1630 via a network 1620, such as a wi-fi network provided by the retailer. In one example, a user of computing device 1630 may be returning an item at the point of sale terminal 1610 and, in exchange for the return of the item, the user is entitled to a gift card with a certain amount of value. Instead of a cashier providing the user with a physical gift card, the point of sale terminal 1610 can send gift card data to the computing device 1630 where the gift card data is associated with a gift card account and is usable by the universal card 1640 to emulate the gift card. In another example, a user of computing device 1630 may wish to obtain a loyalty card while checking out at point of sale terminal 1610. Instead of a cashier providing the user with a physical loyalty card, the point of sale terminal 1610 can send loyalty card data to the computing device 1630 where the loyalty card data is usable by the universal card 1640 to emulate the loyalty card.

Figure 17:
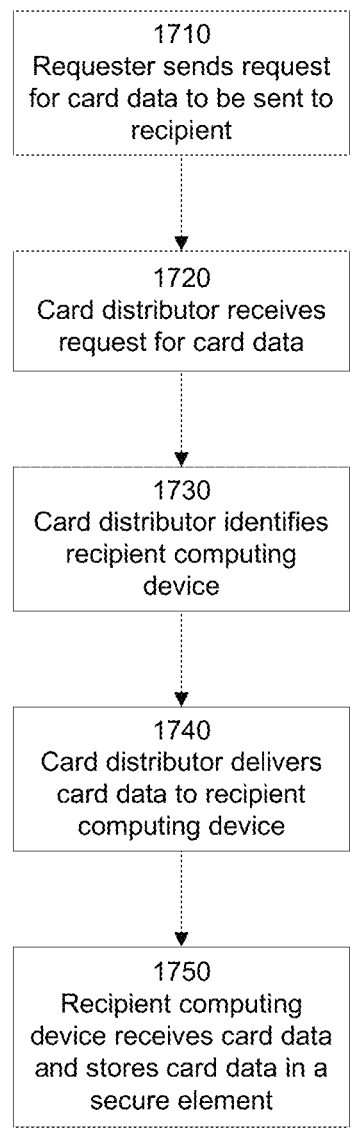
FIG. 17 depicts an exemplary method of providing card data to a universal card.

Referring now to FIG. 17, depicted is a method of providing card data to a universal card. A requester can send a request for card data to be sent to a recipient, as depicted by box 1710. As discussed above, the requester can send the request from a computing device to one or more computing devices associated with the card distributor via a network. In addition, the computing device used by the requester can, but need not be, associated with a universal card. The request can optionally include information identifying the recipient or the recipient's computing device. The card distributor can receive the request for card data, as depicted by box 1720. As discussed above, the request can be received by one or more computing devices associated with the card distributor via a network. The card distributor can identify a computing device associated with the recipient, as depicted by box 1730. As discussed above, identifying the recipient's computing device can include sending an email or text message to the recipient with instructions for downloading the card data. The instructions can include actions by the recipient that will identify the recipient's computing device to the card distributor. Identifying the recipient's computing device can also include information identifying the recipient's computing device in the request sent by the requester. In addition, as described above, the requester can also be the recipient. After the card distributor identifies the computing device of the recipient, the card distributor can deliver the card data to the recipient's computing device, as depicted by box 1740. As described above, the delivery can be from one or more computing devices of the card distributor to the recipient's computing device via a network. The recipient's computing device can receive the card data and store the card data in a secure element. As describe above, the secure element can be located in one or both of the recipient's computing device or a universal card associated with the recipient's computing device. The recipient can program the universal card to emulate a card using the card data delivered to the computing device associated with the recipient.

Figure 18:
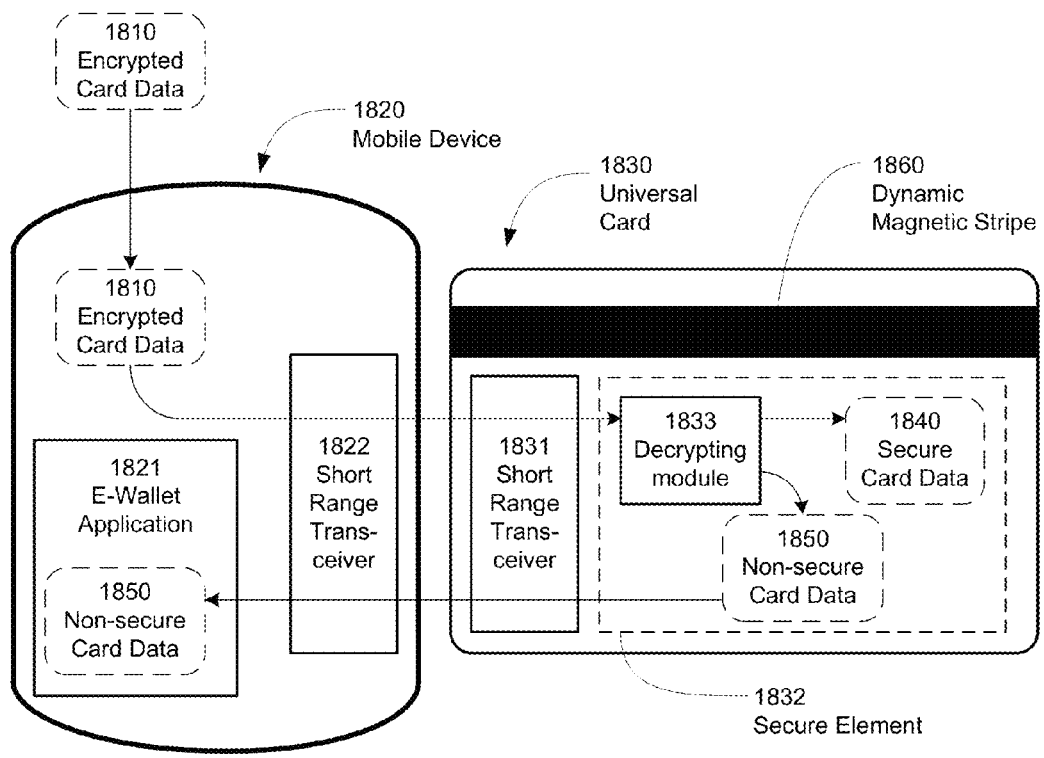
FIG. 18 depicts embodiments of a system and method of securely loading card data onto a universal card that has a secure element

Referring now to FIG. 18, depicted are embodiments of a system and method of securely loading card data onto a universal card that has a secure element. In addition to those advantages discussed above, there are advantages to having the secure element on the universal card instead of the mobile device. A wireless carrier may assert control over access, management, and ownership of a secure element on a mobile device. Such control over the secure element may also include control over use of a short range transceiver for payments. Mobile device manufacturers and application developers can attempt to secure applications using other forms of security, such as secure elements located on SIM cards or SD cards. However, any application or data stored in a mobile device, a SIM card, or an SD card leaves the application or data susceptible to extraction, access, or inspection by thieves and/or hackers. The data on mobile devices can be read by third parties if the mobile device is lost or stolen. Users may protect their mobile device with a PIN or password; however, users frequently use only four-digit PIN numbers (a total of 10,000 possible PINs) or weak passwords that are easily overcome. If any secure card data is located on the phone, recovery of such data would allow the third party to complete transactions using the recovered phone data. Mobile devices also suffer from hacking attacks, such as phishing, Trojan, and Bot attacks. In a phishing attack, a mobile device's browser may be directed to phishing site which is configured to extract secure data from the phone or from the phone's user. In a Trojan or Bot attack, a mobile device may become infected with code which establishes a connection to a hacker's computing device and transfers secure data from the mobile device. Many other attacks on mobile devices are possible. Other attacks on mobile devices include intercepting data that is transmitted to other devices, sometimes referred to as "man-in-the-middle" attacks. When a device establishes a wireless connection, such as an NFC connection, a Bluetooth connection, or Wi-Fi connection, a third party may intercept signals sent via the wireless connection and read, modify, or reroute the data.

The system depicted in FIG. 18 prevents unencrypted secure card data from being stored on a mobile device and from being transmitted between devices. As depicted, encrypted card data 1810 can be sent to mobile device 1820. In one embodiment, the card data can be encrypted using a derived unique key per transaction (DUKPT) key management encryption scheme. In such a scheme, a one-time unique encryption key can be derived for each transaction, and the key can be generated from a master base derivation key (BDK) shared by both the encrypting entity and the decrypting entity. In one embodiment, a unique BDK can be assigned to each customer. After receiving the encrypted card data 1810, the mobile device 1820 can store the encrypted card data 1810. The encrypted data 1810 can be stored either temporarily or indefinitely without concern for the mobile device 1820 being hacked, stolen, or otherwise compromised, as the encrypted card data 1810 can be encrypted in such a way that it is difficult or nearly impossible for the card data to be decrypted by a third party that does not have the proper key(s), such as the DUKPT and the BDK. Mobile device 1820 can include an e-wallet application 1821 and a short range transceiver 1822. The encrypted card data 1810 is unusable to the e-wallet application 1821 since the e-wallet application 1821 is unable to decrypt the encrypted card data 1810.

The mobile device 1820 can transmit the encrypted card data 1810 via the short range transceiver 1822 to universal card 1830 which also has a short range transceiver 1831. While the transmission of the encrypted card data 1810 may be made wirelessly, such as via an NFC connection, a Bluetooth connection, or other short range communication connection, such a transmission will not expose the card data to risk of being read by a man-in-the-middle attack because the card data is being transmitted as encrypted card data 1810. Even if the encrypted card data 1810 was read by a third party, it is difficult or nearly impossible for the card data to be decrypted by the intercepting party without the proper key(s). Once received via the short range transmitter 1831, the encrypted card data 1810 can be passed to secure element 1832 on the universal card 1830. The secure element 1833 can include a decrypting module 1833 which has sufficient information, such as the DUKPT and/or the BDK, to decrypt the card data. The decrypted card data can include both secure card data 1840 and non-secure card data 1850. The secure card data can include information that is typically used to ensure security of financial transactions. For example, many traditional credit and debit cards include a card certification value (CVV1) that is encoded on Track 2 of the magnetic stripe of a traditional card. During a transaction, the CVV1 value is passed to the terminal with the other card data and the terminal can verify the transaction using the CVV1 value. In the system depicted in FIG. 18, the decrypted secure card data 1840 could include the CVV1 value for a particular card. The secure card data 1840 is stored in the secure element 1832 of the universal card 1830. The universal card 1830 can be configured so that it uses the secure card 1840 to configure dynamic magnetic stripe 1860 to emulate a static magnetic stripe of a traditional card, and the universal card 1830 can be configured so that the secure card data 1840 is stored only in secure element 1832 and not transmitted after the secure card data 1840 is decrypted. Non-secure card data 1850 can include information related to a card that would be considered acceptable if lost or stolen. Such non-secure data could include any or all of the following: the name of the issuer of the card (e.g., VISA, AMERICAN EXPRESS, etc), the name of the card holder, the last four digits of the card number, and the expiration date of the card.

The universal card 1830 can transmit the decrypted non-secure card data 1850 to the mobile device 1820 via short range transceiver 1831. The decrypted non-secure card data 1850 can be sent to the mobile device 1820 in a batch file that can include non-secure card data for one or more cards. The mobile device 1820 can receive the non-secure card data 1850 via short range transceiver 1822 and store the non-secure card data 1850. Once stored in the mobile device 1820 stores the non-secure card data 1850, it can be used by e-wallet application 1821. E-wallet application 1821 can provide a user interface which allows a user to view the non-secure card data 1850, to manage card data and card accounts, to select a card for the universal card 1830 to emulate, to assign a nickname to a card, to assign an identifier of the type of card (e.g., VISA word account, MASTERCARD home account, etc), choose a type of card (e.g., loyalty card, debit card, credit card), among other operations.

The system and method depicted in FIG. 18 provide a trusted environment for the secure card data 1840 and the decryption keys required for decrypting encrypted card data 1810. Using the secure element 1832 on a universal card 1830 to both decrypt encrypted card data 1810 and to store decrypted secure card data 1840 greatly reduces the possibility of fraud or theft of card data. The secure card data 1840 does not need to be transmitted off of universal card 1830 and will not be available in a decrypted form off of universal card 1830. Furthermore, mobile device 1820 will not contain any secure card data 1840 in a decrypted format. Thus, there will be no risk to the loss or theft of secure card data 1840 if mobile device 1820 is lost, stolen, or hacked.

Figure 19C:
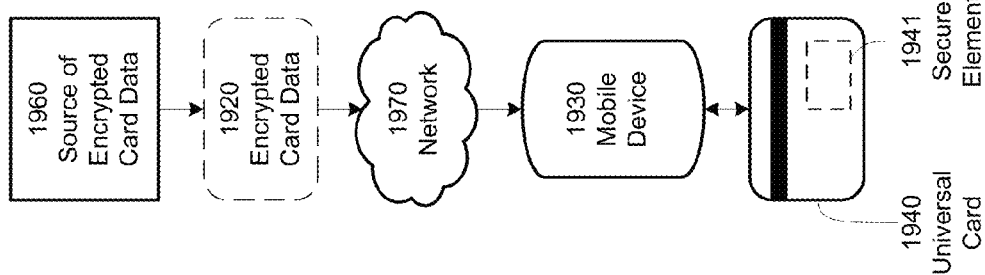
FIGS. 19A, 19B, and 19C depict several embodiments of systems and methods for providing card encrypted to a mobile device for transmission to a universal card with a secure element.
Figure 19B:
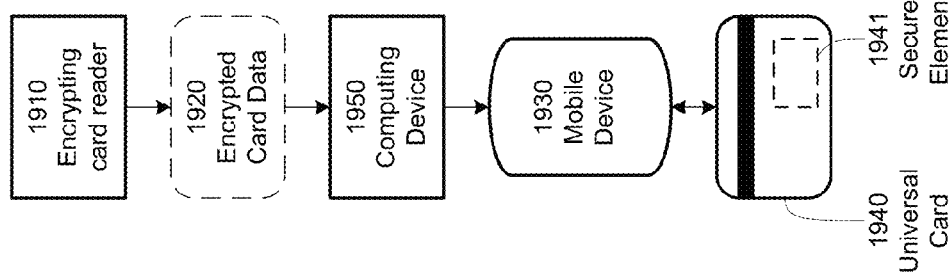
Figure 19A:
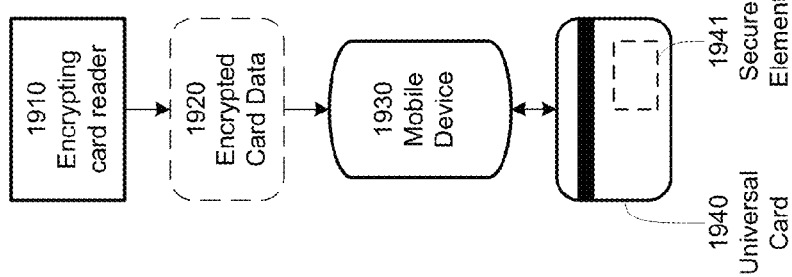

Referring now to FIGS. 19A-19C, depicted are several embodiments of systems and methods for providing card encrypted to a mobile device for transmission to a universal card with a secure element. Depicted in FIG. 19A is an encrypting card reader 1910. A user can swipe a traditional card into encrypting card reader 1910 which will read the data from the traditional card's magnetic stripe and encrypt that data as the card data is read from the traditional card's magnetic stripe to create encrypted card data 1920. In one embodiment, the encrypting card reader 1910 can use a triple data encryption standard (3 DES) and DUKPT to encrypt the card data as it the data is read from the traditional card's magnetic stripe. In the embodiment depicted in FIG. 19A, the encrypting card reader 1910 can be connected directly to mobile device 1930. The connection between encrypting card reader 1910 and mobile device 1930 can be a wired connection, such as a cable connecting encrypting card reader 1910 to an audio jack of mobile device 1930, or a wireless connection, such as via a Wi-Fi network. The encrypted card data 1920 can be communicated from the encrypting card reader 1910 to the mobile device 1930 which transmits the encrypted card data 1920 to universal card 1940. Universal card 1940 can include a secure element 1941 which has a decryption module that can decrypt encrypted card data 1920 and store decrypted secure card data. Universal card 1940 can also transmit decrypted non-secure card data back to mobile device 1930.

Depicted in FIG. 19B is an embodiment where encrypting card reader 1910 is connected to a computing device 1950. Computing device 1950 can be any computing device, such as a personal computer, a laptop computer, a tablet, and the like. A user can swipe a traditional card into encrypting card reader 1910 which will read the data from the traditional card's magnetic stripe and encrypt that data as the card data is read from the traditional card's magnetic stripe to create encrypted card data 1920. The encrypting card reader 1910 can be connected to computing device 1950 via a wired connection, such as a universal serial bus (USB) connection, or a wireless connection, such as via a Wi-Fi network. The encrypted card data 1920 can be communicated from the encrypting card reader 1910 to the computing device 1950 which transmits the encrypted card data 1920 to mobile device 1930. Mobile device 1930 can transmit the encrypted card data 1920 to universal card 1940. Universal card 1940 can include a secure element 1941 which has a decryption module that can decrypt encrypted card data 1920 and store decrypted secure card data. Universal card 1940 can also transmit decrypted non-secure card data back to mobile device 1930.

Depicted in FIG. 19C is an embodiment where a source of encrypted card data 1960 provides encrypted card data 1920 to mobile device 1930. The source of encrypted card data 1960 can be a financial institution, such as a bank, a card issuer, such as a credit card company, a point of sale terminal, such as a terminal in a store that issues loyalty cards and gift cards, or any other source of encrypted card data. The source of encrypted card data 1960 can encrypt the card data to create the encrypted card data 1920 and transmit the encrypted card data 1920 to mobile device 1930 via a network 1970. The network 1970 can be a wired network, a wireless network, or any combination of wired and wireless networks, including one or more of the internet, a cellular phone network, a Wi-Fi network, a local area network, a wide area network, and the like. The network 1970 can also include one or more computing devices. For example, a bank may send encrypted card data 1920 to a user's personal computer via the internet, and the user's personal computer can send the encrypted card data 1920 to mobile device 1930 via a wireless connection, such as a Bluetooth connection or a Wi-Fi connection. In this example, the network 1970 would include the internet, the user's personal computer, and the wireless connection between the user's personal computer and the mobile device 1930. Mobile device 1930 can transmit the encrypted card data 1920 to universal card 1940. Universal card 1940 can include a secure element 1941 which has a decryption module that can decrypt encrypted card data 1920 and store decrypted secure card data. Universal card 1940 can also transmit decrypted non-secure card data back to mobile device 1930.

The encryption of card data can be used with any type of traditional card data. For example, credit card data, debit card data, loyalty card data, identification card data, building access card data, and card data of any other type of card can be encrypted before it is sent to a universal card via a mobile device. The ability to send encrypted card data to a universal card via a mobile device does not preclude the possibility that card data could be sent to a universal card via a mobile device in an unencrypted form. In certain instances, it may be difficult to securely share decryption keys with a universal card. In such instances, it may be more advantageous to send card data in a decrypted form. For example, it may not be required that electronic gift card data is encrypted for transmission to the universal card, and it may be difficult to securely pass decryption keys to the universal card from every possible retailer, electronic gift card issuer, social media site, etc., that issues electronic gift cards. Thus, it may be advantageous to transmit electronic gift card data to a universal card via a mobile device in an unencrypted format even if all other types of card data, such as credit card data, is transmitted to the universal card via the mobile device in an encrypted format.

Figure 20:
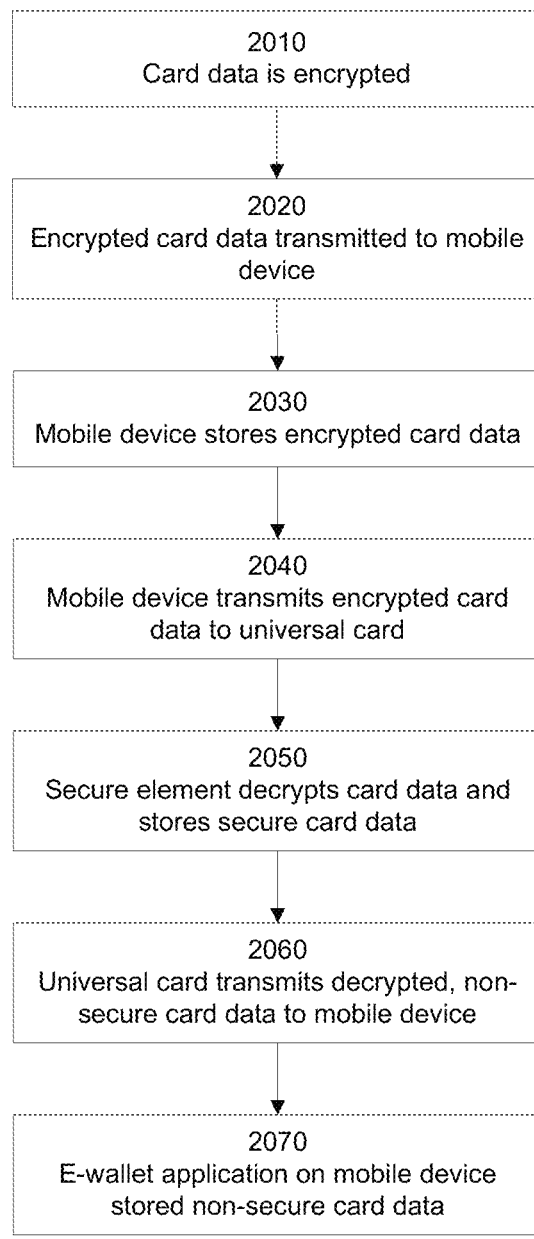
FIG. 20 depicts an embodiment of a method of securely transferring secure card data to a universal card and non-secure card data to a mobile device.

Referring now to FIG. 20, depicted is an embodiment of a method of securely transferring secure card data to a universal card and non-secure card data to a mobile device. At block 2010, the card data is encrypted. In some embodiments, the encryption can be performed by a card issuer, a financial institution, an encrypting card reader, and the like. At block 2020, the encrypted card data is transmitted to a mobile device. The transmission can be performed via one or both of a wired connection and a wireless connection. At block 2030, the mobile device stores the encrypted card data. At block 2040, the mobile device transmits the encrypted card data to a universal card. In one embodiment, the transmission to the universal card is done via a short range communication link, such as an NFC communication link or a Bluetooth communication link. At block 2050, a secure element of the universal card decrypts the encrypted card data. The decrypted card data can include both secure card data and non-secure card data. As shown at block 2050, the secure element can also store the decrypted secure card data. At block 2060, the universal card transmits the decrypted, non-secure card data to the mobile device. In one embodiment, the transmission to the mobile device is done via a short range communication link, such as an NFC communication link or a Bluetooth communication link. At block 2070, an e-wallet application on the mobile device stores the decrypted non-secure card data. While the blocks depicted in FIG. 20 show an order to the steps, one of ordinary skill in the art would recognize that at least some of the steps could be performed in a different order and the methods described herein are not limited to only the order depicted in FIG. 20.

Figure 21A:
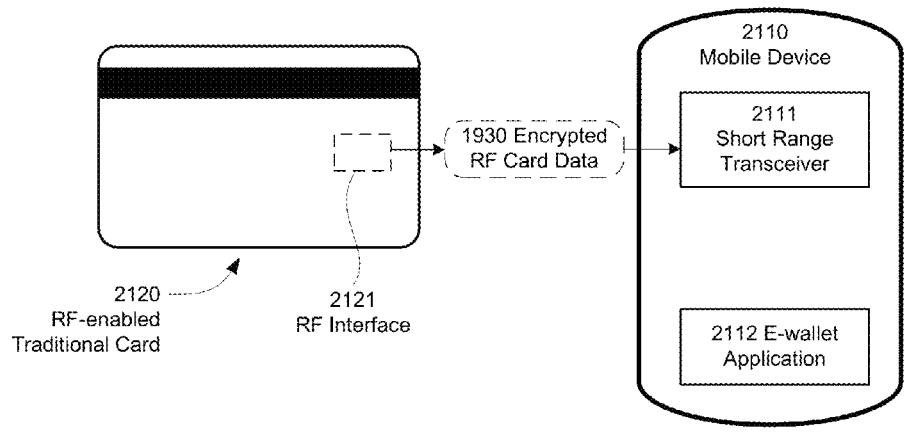
FIGS. 21A and 21B depict embodiments of a mobile device obtaining and using RF card data in conjunction with a universal card.
Figure 21B:
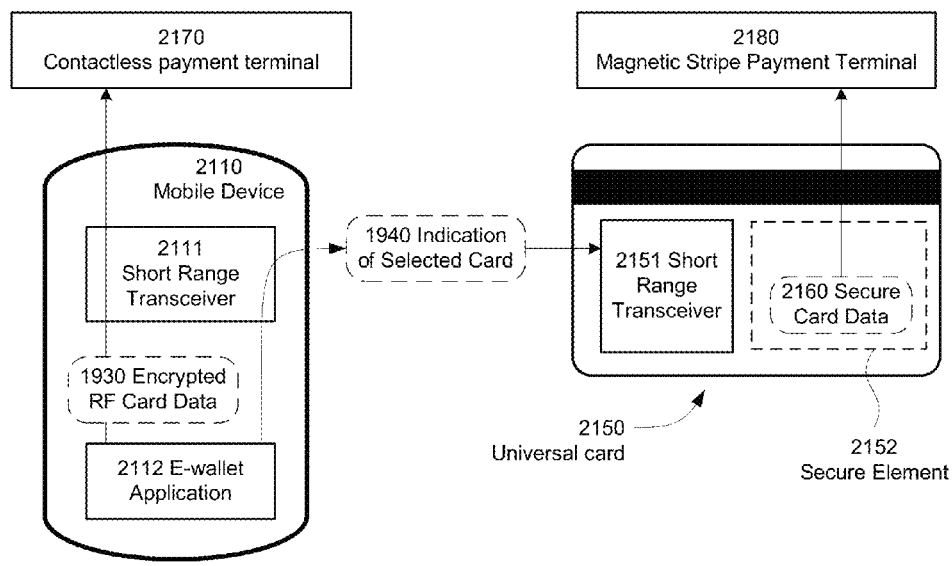

Referring now to FIGS. 21A and 21B, depicted are embodiments of a mobile device obtaining and using RF card data in conjunction with a universal card. FIG. 21A depicts a mobile device 2110 which has a short range transceiver 2111 and an e-wallet application 2112. FIG. 21A also depicts a contactless traditional card 2120 which has an RF interface 2121. The RF interface 2121 transmits encrypted RF card data 1930. Some point-of-sale terminals have contactless payment terminals where an RF receiver can receive the encrypted RF card data 1930 as part of a contactless payment transaction. In such a transaction, a card holder merely brings the contactless traditional card 2120 in close proximity to the contactless payment terminal at which time the encrypted RF card data 1930 is passed from the RF interface 2121 to the contactless payment terminal. In the embodiment depicted in FIG. 21A, the contactless traditional card 2120 can be brought in close proximity to or tapped to the mobile device 2110 when the mobile device is acting as a contactless payment terminal so that the encrypted RF card data 1930 is transmitted from the RF interface 2121 and received by the short range transceiver 2111 of the mobile device 2110. The mobile device 2110 can store the encrypted RF card data 1930 for later use. Since the encrypted RF card data 1930 is already fully encrypted, no further encryption is needed to protect the encrypted RF card data 1930.

The mobile device 2110 may also store non-secure card data associated with the RF-enabled traditional card 2120. In one embodiment, such non-secure card data can be received from a universal card which decrypts encrypted card data. More specifically, in accordance with the description above, the contactless traditional card 2120 may also have a static magnetic stripe which can be read by an encrypting card reader which transmits encrypted card data to the mobile device 2110. The mobile device 2110 can transmit the encrypted card data to a universal card which has a secure element with a decrypting module that decrypts the encrypted card data to obtain decrypted secure card data and decrypted non-secure data. The universal card can transmit the decrypted non-secure card data to the mobile device 2110 which can receive and store the decrypted non-secure data. The mobile device 2110 includes an e-wallet application 2112 which can be used to manage all of the various types of card data on the mobile device 2110. In one embodiment, the e-wallet application can be used to associate the encrypted RF card data 1930 and the non-secure card data stored on the mobile device 2110 with a single card account. For example, a user could associate encrypted RF card data 1930 and the non-secure card data stored with a card account having a nickname of "Work VISA."

Referring now to FIG. 21B, depicted is a an embodiment of the actions taken by the mobile device 2110 when a particular card is selected. Using the e-wallet application 2112 on mobile device, a user can associate both encrypted RF card data 1930 and non-secure card data with a single card account. When the user wants to make a payment, the user can select the card account in the e-wallet application 2112. Upon receiving the user selection of a card account, the e-wallet application 2112 can send encrypted RF card data 1930 and an indication of the selected card 1940 to the short range transceiver 2111. The short range transceiver 2111 can use the encrypted RF card data 1930 such that the mobile device can be presented at a contactless payment terminal 2170. In this case, the mobile device 2110 acts as a contactless payment card. If universal card 2150 is in proximity to the mobile device 2110 to establish a short range communication link, the indication of the selected card 1940 is sent to a short range transceiver 2151 of universal card 2150. The universal card 2150 includes a secure element 2152 which can store secure card data 2160 which is usable to configure a dynamic data communication mechanism, such as a dynamic magnetic stripe, of the universal card 2150. Upon receiving the indication of the selected card 1940, the universal card can configure the dynamic data communication mechanism to emulate a static data communication mechanism of a traditional card. For example, if the dynamic data communication mechanism is a dynamic magnetic stripe, the universal card 2150 can be presented to a magnetic stripe payment terminal 2180 after the dynamic magnetic stripe is configured to emulate a static magnetic stripe of a traditional card. In the embodiment depicted in FIG. 21B, the user's selection of a single card account, such as the "Work VISA" nicknamed account from the example in the preceding paragraph, in the e-wallet application will enable the user to make a payment from the "Work VISA" account either using the mobile device itself with a contactless payment transaction terminal or using the dynamic data communication mechanism of the universal card if the universal card is in close enough proximity to receive the indication of the selected "Work VISA" card. Such a system can lower the complexity of making a payment for the user as the user can make a payment using either the mobile device or the universal card after making a single selection of the card account.

A universal card can also be used as a proxy card. In a proxy payment transaction—sometimes also referred to as a cloud-based payment transaction—a proxy card or information is presented to a point-of-sale (POS) terminal. The proxy card or information is not specifically tied to any one account. Instead, a proxy card server securely stores and synchronizes all of a user's card account information. When the proxy card or information is presented to the POS terminal, the POS terminal communicates, directly or indirectly, with the proxy card server to complete the transaction using the user's card account information. Some current systems exist, but suffer from certain obstacles. For example, one system allows a user to enter a PIN number and a mobile phone number at a POS terminal. The POS terminal communicates the phone number and PIN to a proxy card server to complete the payment transaction. However, this system suffers in that it is not difficult for a person to oversee a user entering a PIN and phone number and use those same credentials in fraudulent transactions. In another example, a payment system allows a user's mobile phone to communicate proxy information to a POS terminal via an NFC connection (contactless payment). However, wide adoption of this system is difficult as most POS terminals have not been upgraded to enable a mobile phone to communicate with a contactless POS terminal via NFC. Another disadvantage is that storage of sensitive proxy card information on the mobile device may require access to a secure element on mobile device. As described above, access to a secure element on the mobile device may require contracts with device manufacturers, wireless carriers, and the like. Using a universal card as a proxy card can overcome a number of deficiencies with current systems, as is described in greater detail below.

Referring now to FIG. 22, depicted is a system and method of using a universal card as a proxy card. The system includes a proxy card server 2210, a mobile device 2220, a universal card 2230, a POS terminal 2240, and a card processing center 2250. The proxy card server 2210 can be located remotely from the mobile device 2220 and the card processing center 2250, and communication between the proxy card server 2210 and each of the mobile device 2220 and the card processing center 2250 can be done by one or more communication networks, such as the internet, cellular telephone networks, Wi-Fi networks, wired communication networks, and the like. Similarly, the POS terminal 2240 and the card processing center 2250 can be located remotely from each other and communicate via one or more communication networks.

Mobile device 2220 can store indications of a proxy card and any number of the user's card accounts that are stored by proxy card server 2210. The indications stored by the mobile device 2220 can be non-secure data so that use of a secure element on the mobile device 2220 is not required. For example, proxy card server 2210 may store information about several of the user's credit cards and the mobile device may store a nickname, the last four digits, and the expiration date of each of the credit cards. Such non-secure data can enable a user to make a selection of one of the card accounts that are stored by proxy card server 2210 without having to store secure card data on the mobile device.

A user can make a selection on the mobile device 2220 to complete a transaction using the universal card 2230 as a proxy card and a selection of the card account that will be used in the transaction. The mobile device 2220 can send 2261 proxy card data, including an indication of the proxy card and an indication of the selected card account, to the proxy card server 2210. The proxy card server 2210 can return 2262 an acknowledgement that the proxy card data was received. The mobile device 2220 can also transmit 2263 proxy card data, including an indication of the proxy card and an indication of the selected card account, to the universal card 2230. The mobile device 2220 and the universal card 2230 can be connected by way of a short range communication link, such as an NFC link or a Bluetooth link. The mobile device 2220 and/or the universal card 2230 can include a secure element that stores the data necessary to configure a dynamic data communication mechanism, such as a dynamic magnetic stripe, to pass the proxy card data to POS terminal 2240. Configuring the dynamic data communication mechanism can include writing the proxy card data to required fields of the dynamic data communication mechanism and writing an indication of the selected card account to a discretionary data field of the dynamic data communication mechanism. During a transaction, the proxy card data and the indication of the selected card can be passed 2264 from the universal card 2230 to the POS terminal 2240, such as when the universal card 2230 is swiped through POS terminal 2240 during a magnetic stripe transaction or when the universal card 2230 is tapped to the POS terminal 2240 during a contactless transaction or when the universal card 2230 is input to the POS terminal 2240 during a EMV transaction.

After receiving the proxy card data and the indication of the selected card, the POS terminal 2240 can send 2265 the proxy card data, the indication of the selected card, and transaction data to the card processing center 2250. The transaction data can include the total amount of the transaction to be processed. The card processing center 2250 can send a request 2266 for the proxy card server 2210 to authenticate the proxy card data and the indication of the selected card. After the proxy card server 2210 authenticates the proxy card data and the indication of the selected card, the proxy card server 2210 can send 2267 a response to the card processing center 2250. The card processing center 2250 can then charge the user's selected account for the total amount and send 2268 a confirmation message to the POS terminal 2240 that the amount was charged. Optionally, the proxy card server 2210 can track the purchases made by the user, including the amounts charged to each of the user's card accounts.

Figure 23:
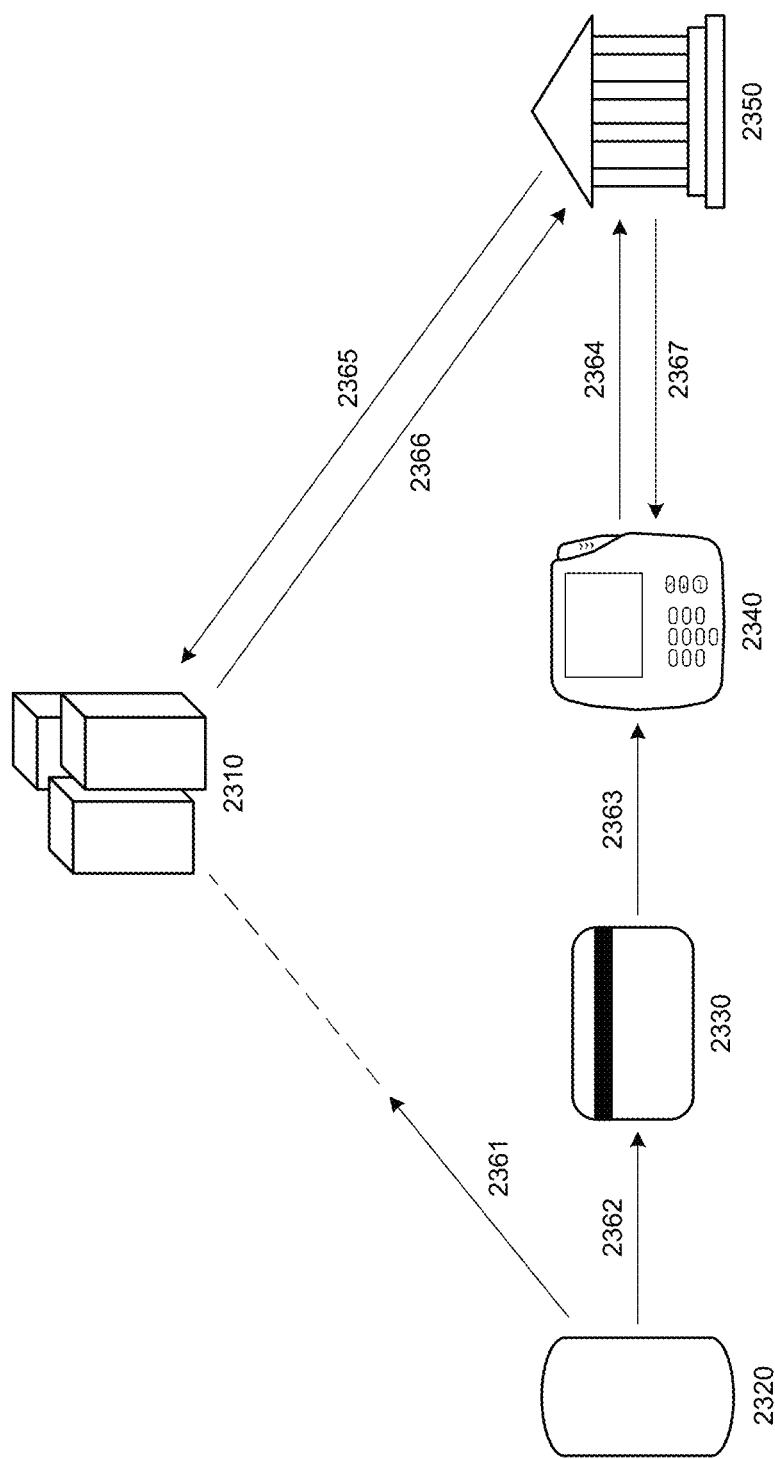
FIG. 23 depicts an embodiment of a system and method of using a universal card as a proxy card when a mobile device is unable to communicate with a proxy card server.

Referring now to FIG. 23, depicted is another embodiment of a system and method of using a universal card as a proxy card. The system includes a proxy card server 2310, a mobile device 2320, a universal card 2330, a POS terminal 2340, and a card processing center 2350. A user can make a selection on the mobile device 2320 to complete a transaction using the universal card 2330 as a proxy card and a selection of the card account that will be used in the transaction. The mobile device 2220 can send 2361 proxy card data, including an indication of the proxy card and an indication of the selected card account, to the proxy card server 2210. However, in the embodiment depicted in FIG. 23, the mobile device 2320 may not be able to connect to proxy card server 2310 or proxy card server 2310 may be unable to respond.

When mobile device 2320 does not receive a response from proxy card server 2310, it can prompt the user to enter a security code, such as a PIN or a password. The mobile device 2320 can transmit 2362 the security code and the proxy card data, including an indication of the proxy card and an indication of the selected card account, to the universal card 2330. The mobile device 2320 and the universal card 2330 can be connected by way of a short range communication link, such as an NFC link or a Bluetooth link. The mobile device 2320 and/or the universal card 2330 can include a secure element that stores the data necessary to configure a dynamic data communication mechanism, such as a dynamic magnetic stripe, to pass the proxy card data to POS terminal 2340. Configuring the dynamic data communication mechanism can include writing the proxy card data to required fields of the dynamic data communication mechanism and writing an indication of the selected card account and the security code to discretionary data fields of the dynamic data communication mechanism. During a transaction, the proxy card data, the indication of the selected card, and the security code can be passed 2363 from the universal card 2330 to the POS terminal 2340, such as when the universal card 2330 is swiped through POS terminal 2340 during a magnetic stripe transaction or when the universal card 2330 is tapped to the POS terminal 2340 during a contactless transaction or when the universal card 2230 is input to the POS terminal 2240 during a EMV transaction.

After receiving the proxy card data, the indication of the selected card, and the security code, the POS terminal 2340 can send 2364 the proxy card data, the indication of the selected card, the security code, and transaction data to the card processing center 2350. The transaction data can include the total amount of the transaction to be processed. The card processing center 2350 can send a request 2365 for the proxy card server 2310 to authenticate the proxy card data, the indication of the selected card, and the security code. After the proxy card server 2310 authenticates the proxy card data, the indication of the selected card, and the security code, the proxy card server 2310 can send 2366 a response to the card processing center 2350. The card processing center 2350 can then charge the user's selected account for the total amount and send 2367 a confirmation message to the POS terminal 2340 that the amount was charged. Optionally, the proxy card server 2310 can track the purchases made by the user, including the amounts charged to each of the user's card accounts.

Figure 24:
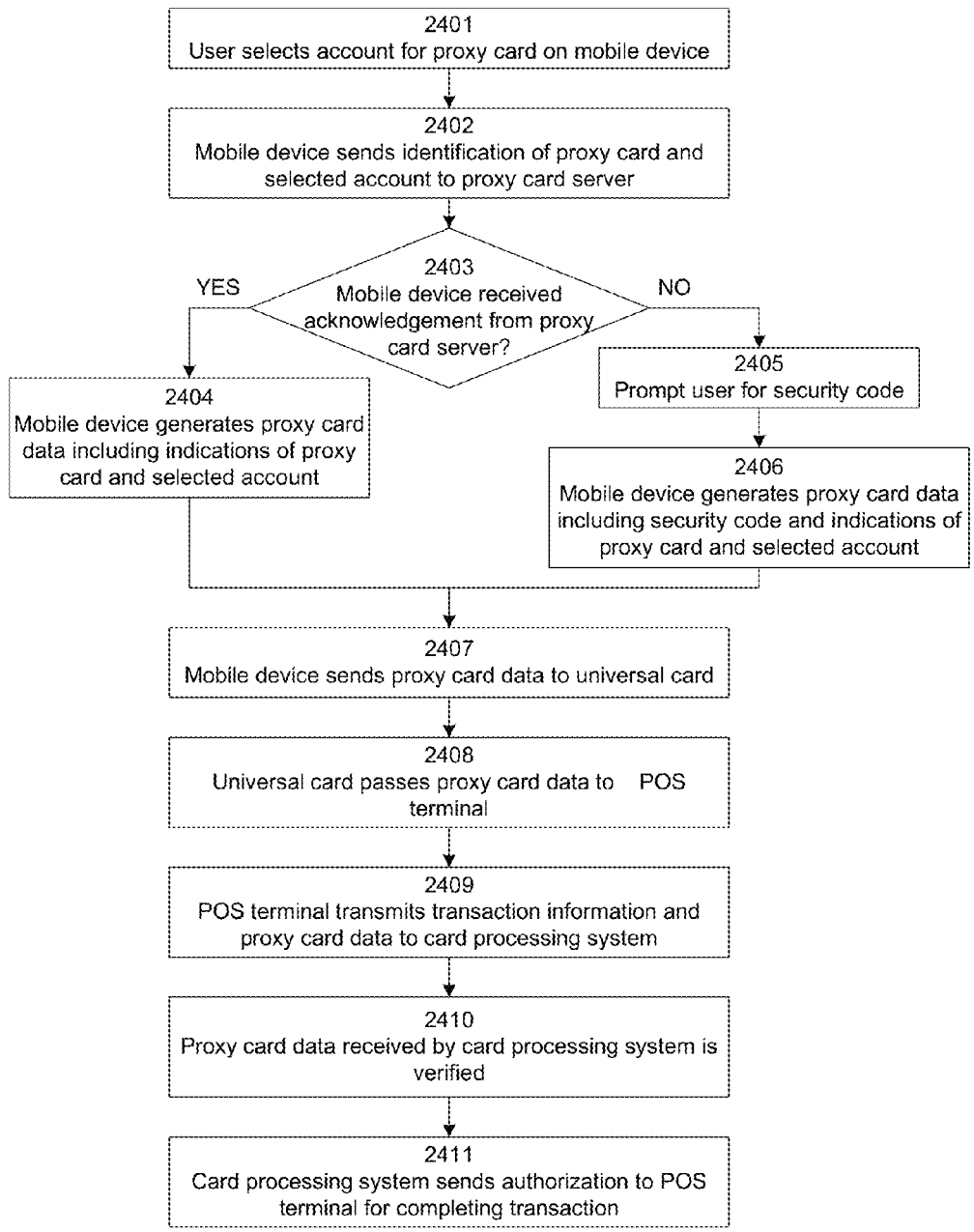
FIG. 24 depicts an embodiment of a method of using a universal card in a proxy card transaction.

Referring now to FIG. 24, depicted is an embodiment of a method of using a universal card in a proxy card transaction. As block 2401, a user can use a mobile device to select a proxy card transaction using a universal card and to select an account for the proxy card transaction. In one embodiment, the user uses an e-wallet application on the mobile device to make the appropriate selection(s). At block 2402, the mobile device sends an indication of the proxy card and the selected account to a proxy card server. At block 2403, the mobile device determines whether an acknowledgement was received from the proxy card server. If an acknowledgement was received from the proxy card server then, at block 2404, the mobile device generates proxy card data, including indications of the proxy card and the selected account. If an acknowledgement was not received from the proxy card server then, at block 2405, the mobile device prompts the user for a security code and, at block 2406, the mobile device generates proxy card data, including the security code and indications of the proxy card and the selected account.

Regardless of whether an acknowledgement was received from the proxy card server, at block 2407, the mobile device can send the proxy card data to the universal card. At block 2408, the universal card can pass the proxy card data to the POS terminal. In one embodiment, passing the proxy card data to the POS terminal includes the universal card writing data associated with the proxy card to required fields of a dynamic magnetic stripe, writing an indication of the selected account to a discretionary data field of the dynamic magnetic stripe, and, optionally, writing the security code to a discretionary data field of the dynamic magnetic stripe. In another embodiment, passing the proxy card data to the POS terminal includes the universal card passing the proxy card data to the POS terminal via an NFC communication link. In another embodiment, passing the proxy card data to the POS terminal includes the universal card passing the proxy card data to the POS terminal via an EMV chip on the surface of the universal card. At block 2409, the POS terminal transmits transaction information and the proxy card data to a card processing system. At block 2410, the proxy card data received by the card processing system is verified. In one embodiment, the card processing system sends the proxy card data to the proxy card server and the proxy card server compares the proxy card data received from the card processing system to the proxy card data received from the mobile device. In another embodiment, the card processing system sends the proxy card data to the proxy card server and the proxy card server verifies a security code in the proxy card data. At block 2411, the card processing system sends an authorization to the POS terminal to complete the transaction.

The use of a universal card as a proxy card has a number of benefits. A universal card that has a dynamic magnetic stripe can be accepted at a much greater number of POS terminals than those systems which rely solely on NFC-enabled contactless POS terminals. If a user's universal card is ever stolen or becomes lost, the user can store any card data, such as magnetic stripe card data, NFC/RFID card data, and EMV card data, required for the universal card to emulate a traditional card or a proxy card. In addition, the use of a universal card as a proxy card is more secure than a traditional proxy card. In one embodiment, if the universal card is ever lost or stolen, the universal card could be disabled. A universal card could be disabled by the proxy card server by the proxy card server recognizing any of the discretionary data provided by the universal card in a proxy card transaction and not authorizing those transactions. The disabling of the universal card could be initiated by the user contacting a proxy card server using a mobile device. Even if the universal card is disabled, the user could continue to make proxy card transactions using the mobile device at NFC-enabled contactless POS terminals.

The universal card can be configured such that the proxy card and a default selected account are a default card unless programmed otherwise. In the default mode, the information of the default card is stored in the secure element of the universal card and the universal card is always configured to emulate the proxy card with the default selected account, unless the user sends new instructions to the universal card to temporarily emulate another card or to change to a new default card.

Proxy cards and their associated selectable accounts can be provisioned in a number of ways. In one embodiment, data associated with a proxy card and any selectable accounts can be added to a secure element of the universal card before the universal card is first provided to the user. In this way, no proxy card data or selectable account data needs be transmitted to the universal card. In another embodiment, the user may swipe any card the user wishes to add into an encrypting card reader. As described in greater detail above, the encrypted card data can be stored in the mobile device, transmitted to the universal card, and decrypted in the universal card's secure element. After decryption, non-secure card data can be transmitted back to the mobile device. In another embodiment, as discussed in more detail above, a service provider can transmit encrypted card data to the mobile device, and the encrypted card data can be stored in the mobile device, transmitted to the universal card, and decrypted in the universal card's secure element. After decryption, non-secure card data can be transmitted back to the mobile device. In another embodiment, a proxy card server can transmit encrypted card data to the mobile device, and the encrypted card data can be stored in the mobile device, transmitted to the universal card, and decrypted in the universal card's secure element. After decryption, non-secure card data can be transmitted back to the mobile device. In yet another embodiment, the user can manually enter card data into the mobile device. The manually entered card data can be transmitted to the universal card and stored in the secure element of the universal card.

Figure 25A:
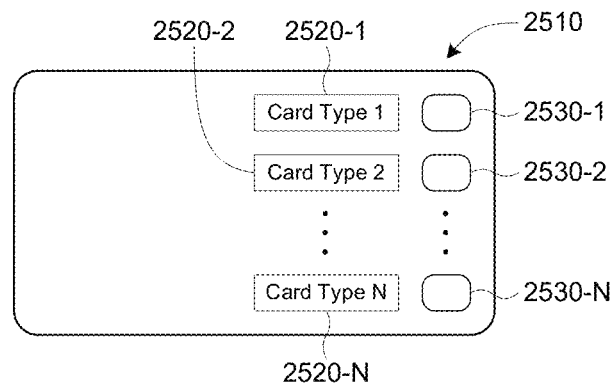
FIGS. 25A and 25B depict embodiments of universal cards for use with multiple proxy card types that each have an associated default card.
Figure 25B:
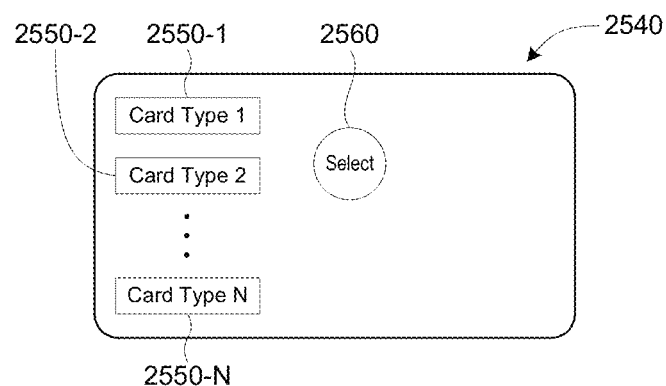

Referring now to FIGS. 25A and 25B, depicted are embodiments of universal cards for use with multiple proxy card types that each have an associated default card. FIG. 25A depicts an embodiment of a universal card 2510 that has labels 2520-1, 2520-2, . . . , 2520-N and a corresponding button 2530-1, 2530-2, . . . , 2530-N for each of the labels 2520. Labels 2520 can include an indication of a type of proxy card. Types of proxy cards can include card issuers, such as VISA, MASTERCARD, DISCOVER, AMERICAN EXPRESS, and the like, card categories, such as credit card, debit card, pre-paid card, loyalty card, gift card, and the like, a miscellaneous (or "other") category, and any other type of proxy card. When any one of buttons 2530 is selected, the corresponding proxy card type can be activated. An active proxy card type can be shown by illumination of the corresponding label 2520, by illumination of the corresponding button 2530, by illumination of a light, such as an LED light, (not shown) corresponding to the proxy card type, or by any other indication. The universal card 2510 may be configured to keep a proxy card type active for a predetermined amount of time following selection of any one of buttons 2530.

When a proxy card type of universal card 2510 is active, one or more dynamic data communication mechanisms of the universal card 2510 can be configured to pass proxy card data for the active card type to a terminal. For example, when a proxy card type of universal card 2510 is activated, one or more of a dynamic magnetic stripe (not shown) of universal card 2510 can be configured to pass proxy card data for the active card type to a terminal with a magnetic stripe reader, a dynamic EMV chip (not shown) of universal card 2510 can be configured to pass proxy card data for the active card type to an EMV-enabled terminal, and a short range communication mechanism (not shown) of universal card 2510 can be configured to pass proxy card data for the active card type to a short range communication mechanism of a terminal in a contactless transaction. The data needed to configure the one or more data communication mechanisms can be stored in a secure element (not shown) of universal card 2510 and retrieved from the secure element for configuring the one or more data communication mechanisms upon activation of a proxy card type.

Figure 26:
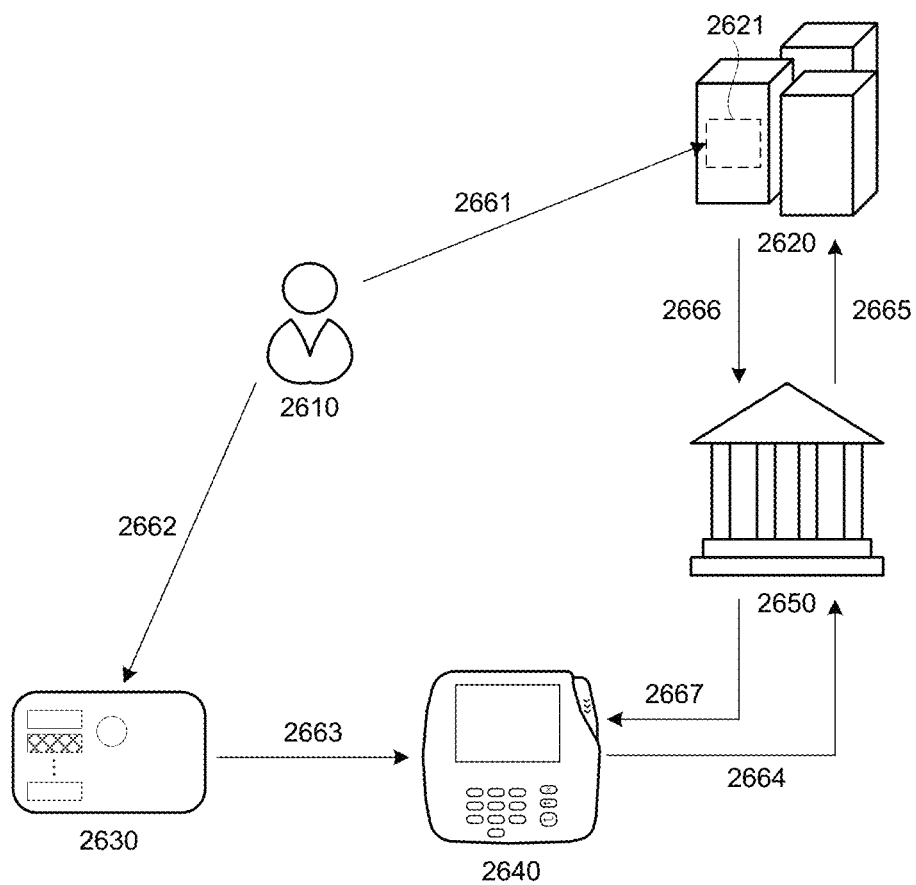
FIG. 26 depicts an embodiment of a system and method of using a universal card with multiple proxy card types where each of the proxy card types has an associated default card.

FIG. 25B depicts an embodiment of a universal card 2540 that has labels 2550-1, 2550-2, . . . , 2550-N and a selection button 2560. Labels 2550 can include an indication of a type of proxy card, similar to the labels 2520 discussed above with respect to universal card 2510 depicted in FIG. 25A. The selection button 2560 can be used to activate any one of the proxy card types indicated by labels 2550. For example, when the selection button 2560 is first pressed, the proxy card type associated with label 2550-1 can be activated. The activation of the proxy card type associated with label 2550-1 can be shown by illumination of the label 2550-1, by illumination of a light (not shown) of a light next to label 2550-1, or any other kind of indication. If the selection button is pressed again, the proxy card type associated with label 2550-2 can be activated. At that point, the activation of the proxy card type associated with label 2550-2 can be shown by illumination of the label 2550-2, by illumination of a light (not shown) of a light next to label 2550-2, or any other kind of indication. Subsequent pressing of selection button 2560 can cycle through each of the proxy card types associated with labels 2550 until reaching the proxy card type associated with label 2550-N. Activation of any proxy card types on universal card 2540 can cause one or more dynamic data communication mechanisms of universal card 2540 to be configured to pass proxy card data associated with the activated proxy card type to a terminal Referring now to FIG. 26, depicted is an embodiment of a system and method of using a universal card with multiple proxy card types where each of the proxy card types has an associated default card. The system in FIG. 26 includes a user 2610, a proxy card server 2620 that stores card type and account information 2621 for user 2610, a universal card 2620, a terminal 2640, and a card processing center 2650. User 2610 can interact 2661 with the card type and account information 2621 stored in proxy card server 2620. The card type and account information can include one or more card accounts for each proxy card type that can be activated on universal card 2630. For example, the universal card 2630 could include labels for each of VISA, MASTERCARD, DISCOVER, AMERICAN EXPRESS, and other. The user's accounts can include a personal VISA credit card, a corporate VISA credit card, a personal MASTERCARD debit card, a personal DISCOVER credit card, a personal AMERICAN EXPRESS credit card, a corporate AMERICAN EXPRESS credit card, a BEST BUY gift card, and a RADIO SHACK gift card. Data for each of the user's accounts can be stored in the card type and account information 2621 in proxy card server 2620. When interacting 2661 with type and account information 2621, the user 2610 can designate a default card for each card type. In the above example, the user can designate the corporate VISA credit card as the default for the VISA card type, the personal MASTERCARD debit card as the default for the MASTERCARD card type, the personal DISCOVER credit card as the default for the DISCOVER card type, the corporate AMERICAN EXPRESS credit card as the default for the AMERICAN EXPRESS card type, and the BEST BUY gift card as the default for the other card type.

Once user 2610 has set default cards for each proxy card type, user 2610 can use universal card 2630 in a transaction. User 2610 can activate 2662 a proxy card type on universal card 2630. When the proxy card type of universal card 2630 is activated, one or more dynamic data communication mechanisms are configured to pass proxy card data for the active proxy card type to terminal 2640. During a transaction, proxy card type data corresponding to the active proxy card type can be passed 2663 from the universal card 2630 to the POS terminal 2640. Using the example from the preceding paragraph, the user 2610 may have activated 2662 the VISA proxy card type on universal card 2630. During the transaction, the universal card 2630 passes 2663 proxy card type data for the VISA proxy card type to terminal 2640.

After receiving the proxy card type data for the active card type, the terminal 2640 can send 2664 the proxy card type data and transaction data to the card processing center 2650. The transaction data can include a total amount of a transaction to be processed. The card processing center 2650 can send 2665 a request that includes the proxy card type data to the proxy card server 2620. The proxy card server 2620 can determine the active proxy card type on universal card 2630 based on the proxy card type data received from the card processing center 2650. The proxy card server 2620 can also determine the default card for the active proxy card type. Using the example from the preceding paragraphs, the proxy card server 2620 can determine that the active card type on universal card 2630 is the VISA card type based on the VISA proxy card data being sent from the card processing center 2650 to the proxy card server 2620. The proxy card server 2620 can determine that the corporate VISA credit card is the default card for the VISA card type at that particular time.

After determining the default card for the active card type, proxy card server 2620 can send 2666 a response to the card processing center 2650 that includes an indication of the default card for the active card type. Using the example above, the response can include an indication of the corporate VISA card. The card processing center 2650 can then charge an account associated with the default card for the amount of the transaction. The card processing center 2650 can send 2667 a confirmation message to the terminal 2640 that the transaction was approved.

One of the benefits of the system depicted in FIG. 26 is that the user 2610 will have quick and easy access to multiple types of card accounts using universal card 2630. Once the user 2610 has selected the default cards for the available card types on the universal card 2630, the user 2610 will be able to take the universal card 2630 to any terminal 2640, activate a desired card type on the universal card 2630, and complete a transaction with terminal 2640 using the default card associated with the activated card type.

The proxy card server 2620 can provide a number of features for user 2610 to manage default cards in the card type and account information 2621. In one embodiment, the user 2610 can select to automatically adjust default cards for each of the proxy card types associated with universal card based on time. Using the example above, the user 2610 can designate the corporate VISA credit card as the default for the VISA card type and the corporate AMERICAN EXPRESS credit card as the default for the AMERICAN EXPRESS card type during the hours of 8:00 a.m. until 6:00 p.m. on weekdays. The user 2610 can also designate the personal VISA credit card as the default for the VISA card type and the personal AMERICAN EXPRESS credit card as the default for the AMERICAN EXPRESS card type at all other times. Setting default cards based on time in this manner may make it more likely that user 2610 uses a corporate cards during business hours and personal cards outside of business hours. In another embodiment, the user 2610 can select any type of card to be a default card for an "other" card type. For example, the default card type can be a loyalty card for a particular store, a gift card for any retailer, a keycard, or any other type of card. Allowing the user 2610 to select any type of card for an "other" card type gives the user 2610 flexibility to utilize the proxy card type function of the universal card 2630 in any way that best suits the needs of user 2610.

Figure 27:
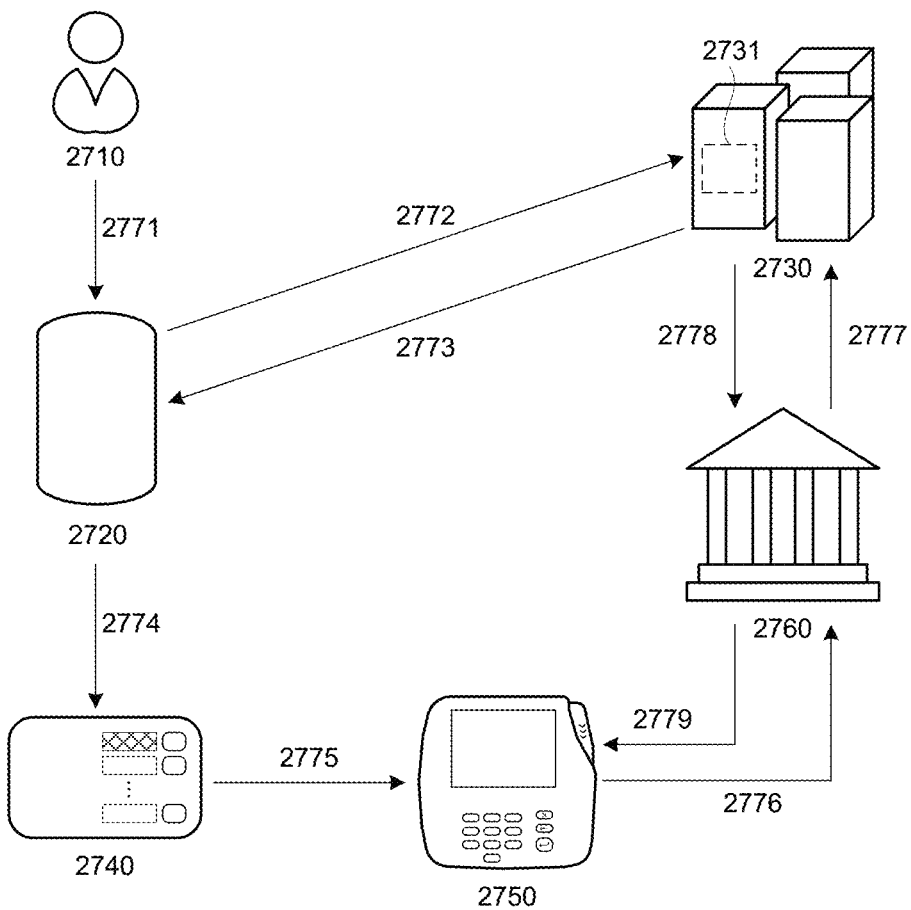
FIG. 27 depicts another embodiment of a system and method of using a universal card with multiple proxy card types where each of the proxy card types has an associated default card.

Referring now to FIG. 27, depicted is another embodiment of a system and method of using a universal card with multiple proxy card types where each of the proxy card types has an associated default card. The system in FIG. 27 includes a user 2710, a computing device 2720, a proxy card server 2730 that stores card type and account information 2731 for user 2710, a universal card 2740, a terminal 2750, and a card processing center 2760. User 2710 can interact 2771 with computing device 2720 to manage card type and account information 2731 in proxy card server 2730. When user 2710 enters a change to the default card for a given proxy card type on computing device 2720, the computing device 2720 can send 2772 a request for the change to be made in the card type and account information 2731 stored in proxy card server 2730. The proxy card server 2730 can make the change and send 2773 a confirmation that the change was made. Once computing device 2720 receives the confirmation, the computing device 2720 can acknowledge to the user 2710 that the change was made successfully.

Once user 2710 has set default cards for each proxy card type, user 2710 can activate a proxy card type on universal card 2740. In the embodiment depicted in FIG. 27, user 2710 can use computing device 2720 to select a proxy card type, and computing device 2720 can send 2774 instructions to universal card 2740 to activate the selected proxy card type. Once universal card 2740 receives the instructions and activates the selected proxy card type, the universal card 2740 can provide an indication of the activated proxy card type, such as by illuminating a label associated with the activated card type. In another embodiment, the user 2710 can use a button or buttons on the universal card to activate one of the proxy card types.

When the proxy card type of universal card 2740 is activated, one or more dynamic data communication mechanisms can be configured to pass proxy card data for the active proxy card type to terminal 2750. During a transaction, proxy card type data corresponding to the active proxy card type can be passed 2775 from the universal card 2740 to the terminal 2750. After receiving the proxy card type data for the active card type, the terminal 2750 can send 2776 the proxy card type data and transaction data to the card processing center 2760. The transaction data can include a total amount of a transaction to be processed. The card processing center 2760 can send 2777 a request that includes the proxy card type data to the proxy card server 2730. The proxy card server 2730 can determine the active proxy card type on universal card 2740 based on the proxy card type data received from the card processing center 2760. The proxy card server 2730 can also determine the default for the active card type. After determining the default card for the active card type, proxy card server 2730 can send 2778 a response to the card processing center 2760 that includes an indication of the default card for the active card type. The card processing center 2760 can then charge an account associated with the default card for the amount of the transaction. The card processing center 2760 can send 2779 a confirmation message to the terminal 2750 that the transaction was approved.

Figure 28A:
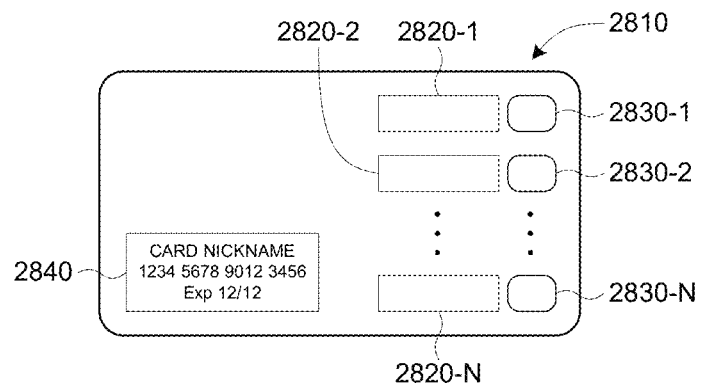
FIGS. 28A and 28B depict embodiments of universal cards for use with multiple proxy card types that each have an associated default card.
Figure 28B:
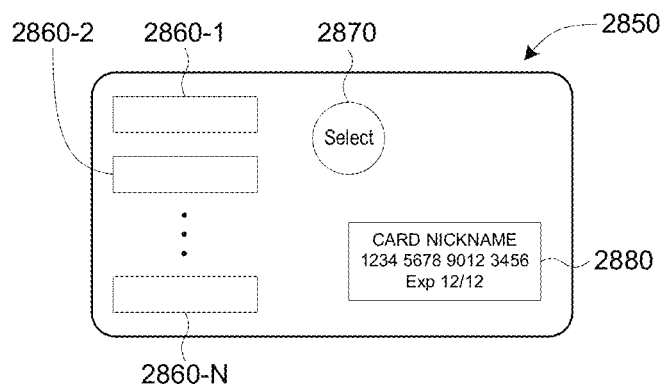

Referring now to FIGS. 28A and 28B, depicted are embodiments of universal cards for use with multiple proxy card types that each have an associated default card. FIG. 28A depicts an embodiment of a universal card 2810 that has labels 2820-1, 2820-2, . . . , 2820-N and a corresponding button 2830-1, 2830-2, . . . , 2830-N for each of the labels 2820. Labels 2820 can include an indication of a type of proxy card. Universal card 2810 can also include a display 2840. When any one of buttons 2830 is selected, the corresponding proxy card type can be activated. Information about the selected proxy card type—such as any or all of an indication of the selected proxy card type (e.g., "VISA"), an indication of a card number associated with the selected proxy card type, an indication of the expiration of the card number associated with the selected proxy card type, and a CVV2 value associated with the selected proxy card type— can be displayed in display 2840. Similarly, information about the default card associated with the selected proxy card type—such as any or all of an indication of the default card (e.g., "Personal VISA," "Corporate VISA," etc), an indication of a card number of the default card, an indication of the expiration of the default card, and a CVV2 value of the default card—can be displayed in display 2840. The information about the selected proxy card type and/or information about the default card associated with the selected proxy card type can be stored in a secure element (not shown) of the universal card 2810. Having a display 2840 on universal card 2810 may eliminate the need for illumination of any of labels 2820, buttons 2830, or other light to indicate which proxy card type has been selected.

In order for the display 2840 of universal card 2810 to be able to display information about the default card, information about changes to the default card can be communicated to the universal card 2810. For example, referring back to the system depicted in FIG. 27, user 2710 can enter a change to the default card for a given proxy card type into computing device 2720. Computing device 2720 can send 2772 a request for the change to be made in the card type and account information 2731 stored in proxy card server 2730. The proxy card server 2730 can make the change and send 2773 a confirmation that the change was made. Once computing device 2720 receives the confirmation, the computing device 2720 can send an indication to universal card 2740 of the change to the default card. In another example using the system depicted in FIG. 27, when universal card 2740 connects to computing device 2720, universal card can send a request to computing device 2720 to obtain a current listing of default cards associated with the proxy card types supported by universal card 2740. If computing device 2720 has a current listing of default cards, computing device 2720 can communicate the current listing to universal card 2740. If computing device 2720 does not have a current listing of default cards, computing device 2720 can send a request to proxy card server 2730 for the current listing, receive the current listing from proxy card server 2730, and communicate the current listing to universal card 2740.

A computing device can also be used as a display, similar to the way in which display 2840 of universal card 2810. For example, referring back to the system depicted in FIG. 27, a proxy card type can be activated on universal card 2740. The proxy card can be activated by selecting a button on universal card 2740 or by making a selection on computing device 2720 and communicating the selection from computing device 2720 to universal card 2740. When the selected proxy card type is activated, the universal card 2740 can send a signal to computing device 2720 to display information about the selected proxy card type and/or the default card associated with the selected proxy card type. If the information to be displayed on computing device 2720 is stored in a secure element of universal card 2740, the signal sent from universal card 2740 to computing device 2720 can include that information. Such a request to display information about the selected proxy card type and/or the default card associated with the selected proxy card type can be sent from universal card 2740 to computing device 2720 regardless of whether universal card 2740 includes a display.

FIG. 28B depicts an embodiment of a universal card 2850 that has labels 2860-1, 2860-2, . . . , 2860-N and a selection button 2870. Labels 2860 can include an indication of a type of proxy card. The selection button 2870 can be used to activate any one of the proxy card types indicated by labels 2860 by cycling through each of the proxy card types. When the select button 2870 is pressed to active one of the proxy card types, display 2880 can display any or all of a nickname, a card number, an expiration date, a CVV2 value, or any other information about either the selected proxy card type or the default card associated with the selected proxy card type. Universal card 2850 can also interact with a computing device to obtain default card changes, to display information about a selected proxy card type and/or default card, or to perform any of the other functions described above.

Figure 29:
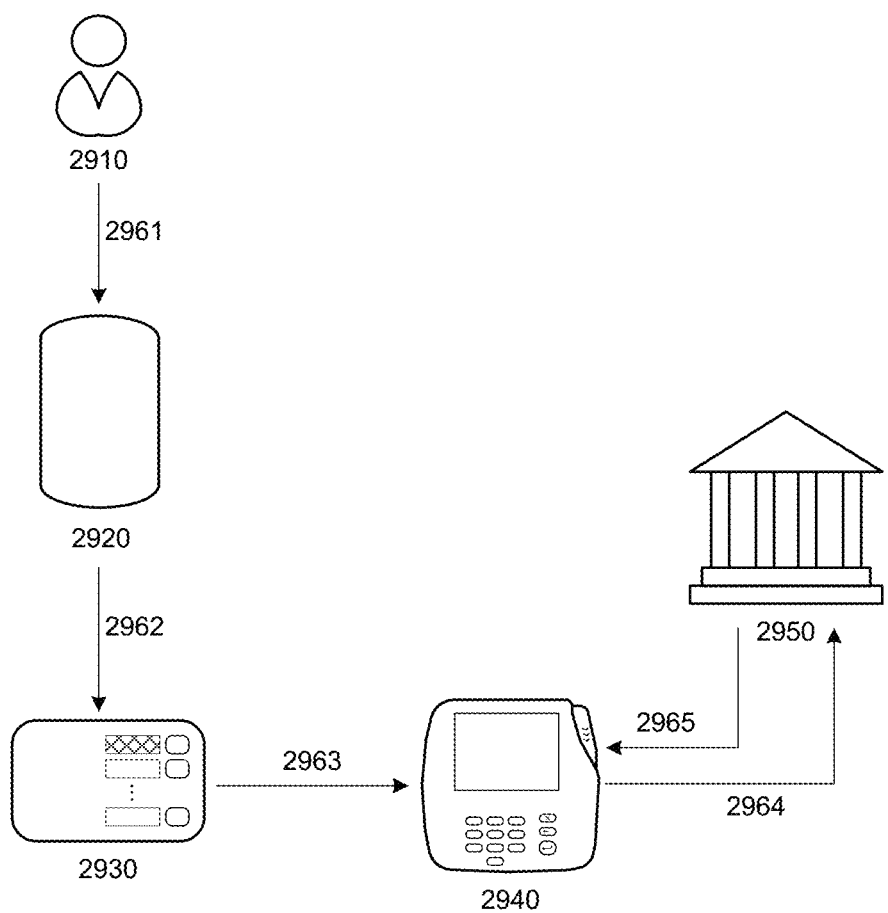
FIG. 29 depicts an embodiment of a system and method of using a universal card with default cards stored locally on the universal card.

Referring now to FIG. 29, depicted is another embodiment of a system and method of using a universal card with default cards stored locally on the universal card. The system in FIG. 29 includes a user 2910, a computing device 2920, a universal card 2930, a terminal 2940, and a card processing center 2950. Universal card 2930 can be configured with several selectable card types, such as VISA, AMERICAN EXPRESS, "other," and so on. Universal card 2930 can store card data for one or more cards associated with each of the card types (e.g., a personal VISA and corporate VISA associated with the VISA card type; a gift card, a loyalty card, and a key card associated with the "other" card type; etc.). Universal card 2930 can also store a default card for each of the selectable card types. For example, universal card 2930 may have a selectable VISA card type and a personal VISA card may be associated with the VISA card type when a user 2910. When user 2910 selects the VISA card type on the universal card 2930, the universal card can configure one or more dynamic data mechanism to pass card data associated with the default card to the terminal 2940. User 2910 can interact 2961 with computing device 2920 to manage card type information and default card selections that are stored locally on universal card 2930. When user 2910 enters a change on computing device 2920 to the default card selection for a card type, the computing device 2920 can send 2962 a request for the change to be made in the default card selection stored in universal card 2930. The universal card 2930 can make the change and, optionally send a confirmation back to the computing device 2920.

When the user 2910 wants to make a transaction, the user 2910 can activate a card type on universal card 2930. A card type can be activate by pressing a button on universal card 2930 or by interacting with computing device 2920 which can send a signal to universal card 2930 to activate the selected card type. When a card type is activated, the universal card 2930 determine the default card for the selected card type. Universal card 2930 can configure one or more dynamic data communication mechanisms to pass card data for the default card to terminal 2940. Card data for one or more of the default cards can be stored in a secure element in universal card 2930. During a transaction, card data corresponding to the default card can be passed 2963 from the universal card 2930 to the terminal 2940 via the one or more dynamic data communication mechanisms. After receiving the card data for the default card, the terminal 2940 can send 2964 the default card data and transaction data to the card processing center 2950. The transaction data can include a total amount of a transaction to be processed. The card processing center 2950 can then charge an account associated with the default card for the amount of the transaction. The card processing center 2950 can send 2965 a confirmation message to the terminal 2940 that the transaction was approved.

As described above, a universal card can be configured to emulate a key card. In one example, a dynamic magnetic stripe of the universal card can be configured to emulate a static magnetic stripe of a traditional key card and the universal card can be swiped through a magnetic stripe reader of a terminal. The terminal can read the data from the dynamic magnetic stripe. In another example, a dynamic radio-frequency identification (RFID) transmitter of the universal card can be configured to emulate a static RFID transmitter of a traditional key card and the universal card can be exposed to an RFID reader of a terminal. The terminal can receive data transmitted by the dynamic RFID transmitter. In another example, a dynamic short range communication mechanism of the universal card can be configured to emulate a static short range communication mechanism of a traditional key card and the universal card can transmit data to the terminal via a short range communication link. The terminal can receive data transmitted via the short range communication link.

Figure 30B:
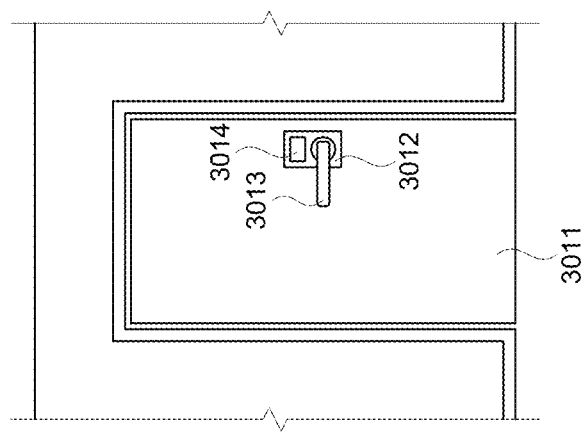
FIGS. 30A and 30B, depict embodiments of key card building access points.
Figure 30A:
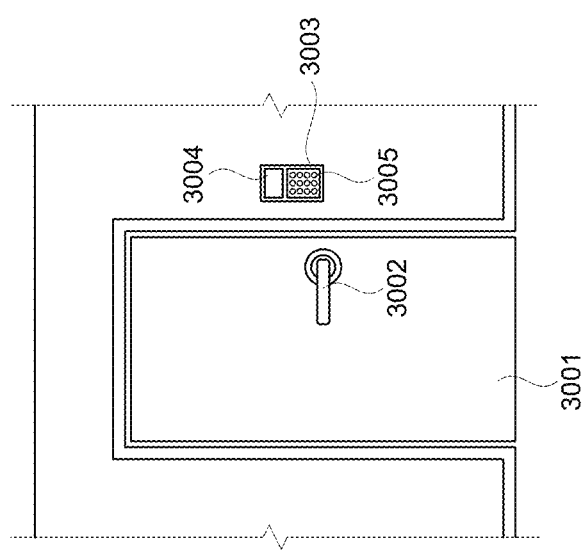

Referring now to FIGS. 30A and 30B, depicted are embodiments of key card building access points. FIG. 30A depicts a door 3001 with a handle 3002. Handle 3002 can be any kind of handle, such as a lever handle (as depicted in FIG. 30A), a knob, a push bar, a pull handle, and the like. A key card terminal 3003 is located near door 3001. Key card terminal 3003 can include a key card reader 3004. The key card reader 3004 can include a magnetic stripe reader, an RFID receiver, a short range communication receiver, and the like. A key card can be presented to and pass data to key card reader 3004. For example, a magnetic stripe of a key card can be swiped through a magnetic stripe reader of key card reader 3004 and the magnetic stripe reader can read data from the magnetic stripe of the key card. In such a case, the data can be written to any portion of the dynamic magnetic stripe, including Track 3 of the dynamic magnetic stripe. In another example, an RFID transmitter of a key card can be presented to and transmit data to an RFID receiver of key card reader 3004. In yet another example, a near field communication (NFC) transmitter of a key card can be presented to and transmit data to an NFC receiver of key card reader 3004. As discussed in greater detail below, a user of a universal card can configure the universal card to emulate a key card using the appropriate data passing mechanism—such as a dynamic magnetic stripe, a dynamic RFID transmitter, a dynamic short range communication mechanism—so that the universal card can interact with the key card reader 3004.

After key card reader 3004 receives data from a key card, the key card terminal 3003 can determine whether to unlock the door 3001 based on the received data. In addition to determining whether to unlock the door 3001 based on the received data, the determination can be further based on one or more of the time of day, the day of the week, a security level, or any other factor. In one embodiment, the key card terminal 3003 can also include a user input mechanism 3005. The user input mechanism 3005 depicted in FIG. 30A has the form of a keypad. As a secondary level of security, the key card terminal 3003 can require a user to input a certain code, such as a PIN number, into the user input mechanism 3005 in addition to the key card reader 3004 receiving appropriate data from the key card. The user input mechanism 3005 can also take forms other than or in addition to the depicted keypad, such as a biometric sensors that can identify one or more of a user's fingerprint, a user's voice, and the like. The determination by key card terminal 3003 whether to unlock the door can include the key card terminal 3003 communicating information to a remote computing device, such as a server, and receiving an indication from the remote computing device whether the door should be unlocked.

The key card terminal 3003 can log all attempts to unlock the door 3001 using a key card. The key card terminal 3003 can log both successful and unsuccessful attempts to unlock the door 3001. The log can be stored locally on the key card terminal 3003, remotely on a remote computing device, or any other location.

The door 3001 depicted in FIG. 30A can be a door in any environment. For example, the door 3001 can be a door in a corporate environment, such as an entrance to a building, a door to an individual office, a door to a secure area, such as a server room, and the like. Different users can have different access to different doors at different times, such as the exemplary case where one worker is able to unlock an entrance door during business hours only and not unlock any other doors and where a second worker is able to unlock any door at any time. In another example, the door 3001 can be door to a secure area in a military environment. In another example, the door 3001 can be door to a secure area in a hospital or other medical provider office, such as a prescription locker or other supply area. In another example, the door 3001 can be door to a home. In another example, the door 3001 can be door to a vehicle.

While the key card terminal 3003 is depicted in FIG. 30A as controlling the door 3001, a key card can also be associated in other access-restricted situations. For example, some cars include an RFID receiver that can determine when a key having an authorized RFID transmitter is inside the car. These cars can also include a button, or some other key-less mechanism, that can start and stop the engine when a key having an authorized RFID transmitter is inside the car. In other words, the engine cannot be started unless the key with the authorized RFID transmitter is inside the car. In this example, a universal card can be configured to emulate the key with the authorized RFID transmitter by configuring a dynamic RFID transmitter to transmit the same data that the traditional key would transmit. When the dynamic RFID transmitter of the universal card is properly configured and inside the card, the card would allow the engine to be started. In other examples of access-restricted situations, a key card terminal 3003 can control access to a gate, a turnstile, a computing system, and the like.

FIG. 30B depicts another embodiment with a door 3011 having a handle panel 3012 with a handle 3013. The handle panel 3012 can also include a key card reader 3014. The key card reader 3014 can include a magnetic stripe reader, an RFID receiver, a short range communication receiver, or any other type of key card reader. A key card can be presented to and pass data to key card reader 3014. The key card reader 3014 can determine whether to unlock the door 3011 in way similar to those described above with respect to key card terminal 3003.

Figure 31:
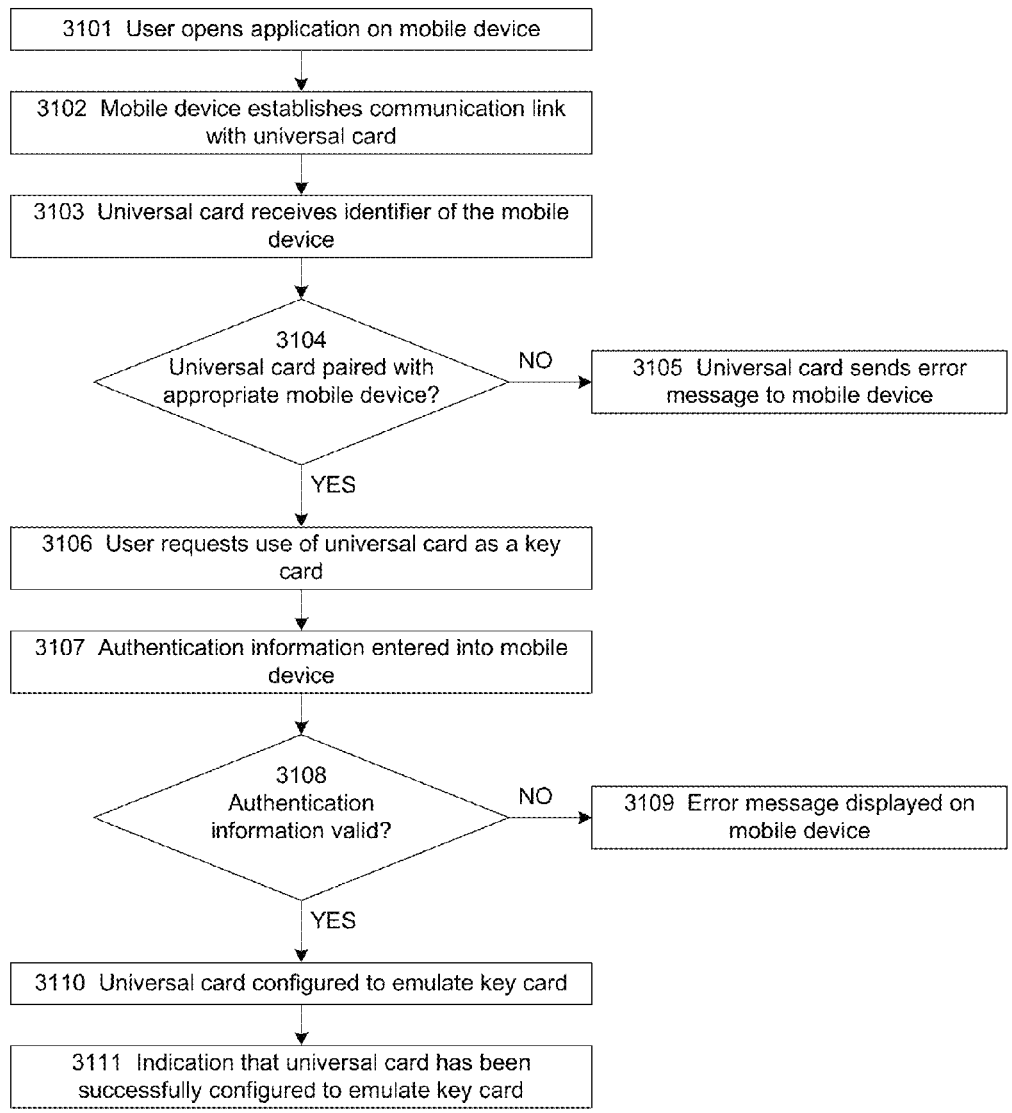
FIG. 31 depicts an embodiment of a method of configuring a universal card to emulate a key card.

Referring now to FIG. 31, depicted is an embodiment of a method of configuring a universal card to emulate a key card. At block 3101, the user can open an application on a mobile computing device. The application can be any type of application, such as an e-wallet application, an application developed by a maker of the universal card, an application associated with the location to which the user desires to gain entry, an application developed by a maker or distributer of the key card terminal, and the like. At block 3102, the mobile device can establish communication with the universal card. Such a connection can be made by way of a short range communication link, such as a near field communication link, a Bluetooth communication link, and the like. The application can be configured to initiate the establishing of the communication between the mobile device and the universal card upon startup of the application.

At block 3103, the universal card can receive an identifier of the mobile device. The identifier can be send from the mobile device to the universal card. At block 3104, a determination can be made whether the universal card is paired with the appropriate mobile device. For example, an authorized user may initially pair universal card with a first mobile device for use as a key card. An unauthorized user may attempt to configure the universal card to emulate a key card by communicating with the universal card using a second mobile device. In such a case, the second mobile device will not send the identifier of the first mobile device and, at block 3104, the universal card can determine that it is not paired with an appropriate mobile device. If, at block 3104, it is determined that the universal card is not paired with an appropriate mobile device, then, at block 3105, the universal card can send an error message to the mobile device. The mobile device can play a sound or display a message to the user indicating that there was an error in trying to connect to the universal card. However, if, at block 3014, it is determined that the universal card is paired with an appropriate mobile device, then the method can continue to block 3106.

At block 3106, the user can request that the user of the universal card as a key card. The user can make such a request in the application running on the mobile device. The request can include an indication of a type of key card that the universal card is to emulate. Alternatively, the request may be silent as to the type of key card and the universal card may emulate a default key card upon receiving such a request. At block 3107, the user can be prompted to enter authentication information into the mobile device. For example, the user may be prompted to enter a PIN or a password into the mobile device. In another example, the user may be prompted to provide a fingerprint or speak one or more words for biometric authentication. At block 3108, a determination can be made whether the authentication information provided by the user is valid. If the authentication information provided is determined not to be valid, then, at block 3109, an error message can be displayed on the mobile device. The error message can indicate that the authentication attempt failed. However, if, at block 3108, the authentication information provided is determined to be valid, then, at block 3110, the universal card can be configured to emulate the key card. An indication of the particular dynamic data passing mechanism to be used to emulate the key card, such as an indication of a dynamic magnetic stripe reader, an dynamic RFID receiver, or a dynamic short range communication receiver, can be stored in a secure element of the universal card. In addition, the data to be passed from the dynamic data passing mechanism to a key card reader can be stored in the secure element of the universal card. At block 3111, an indication can be made that the universal card has been successfully configured to emulate a key card. The indication can be a light on the universal card, a sound made by the universal card or the mobile device, a message on a display of the mobile device, and the like.

The two levels of security depicted in FIG. 31—including the determinations made at blocks 3104 and 3108—can limit attempts by unauthorized users from using the universal card as a key card. In the method depicted in FIG. 31, the user must have the appropriate mobile device paired with the universal card and the user must provide some additional information, such as a PIN. For example, it may be possible for an unauthorized user to obtain the universal card and even the authorized user's mobile device, but it is less likely that the unauthorized user could obtain the authorized user's PIN in addition to the universal card and the authorized user's mobile device. In addition to using the mobile device to enter a PIN, the mobile device can be used to enter a fingerprint, the sound of a voice, or any other code or biometric reading. The universal card may not be programmed until after authenticating the user with one or more of the authentication techniques described above. The number and type of authentication techniques utilized on the mobile device and/or with the card can be based on the level of security desired. For example, a hotel may require only entry of a PIN into an application on the mobile computing device. In another example, a high security area may require entry of a combination of authentication types, such as fingerprint, voice, and keyword, to provide a multi-factor authentication.

Figure 32A:
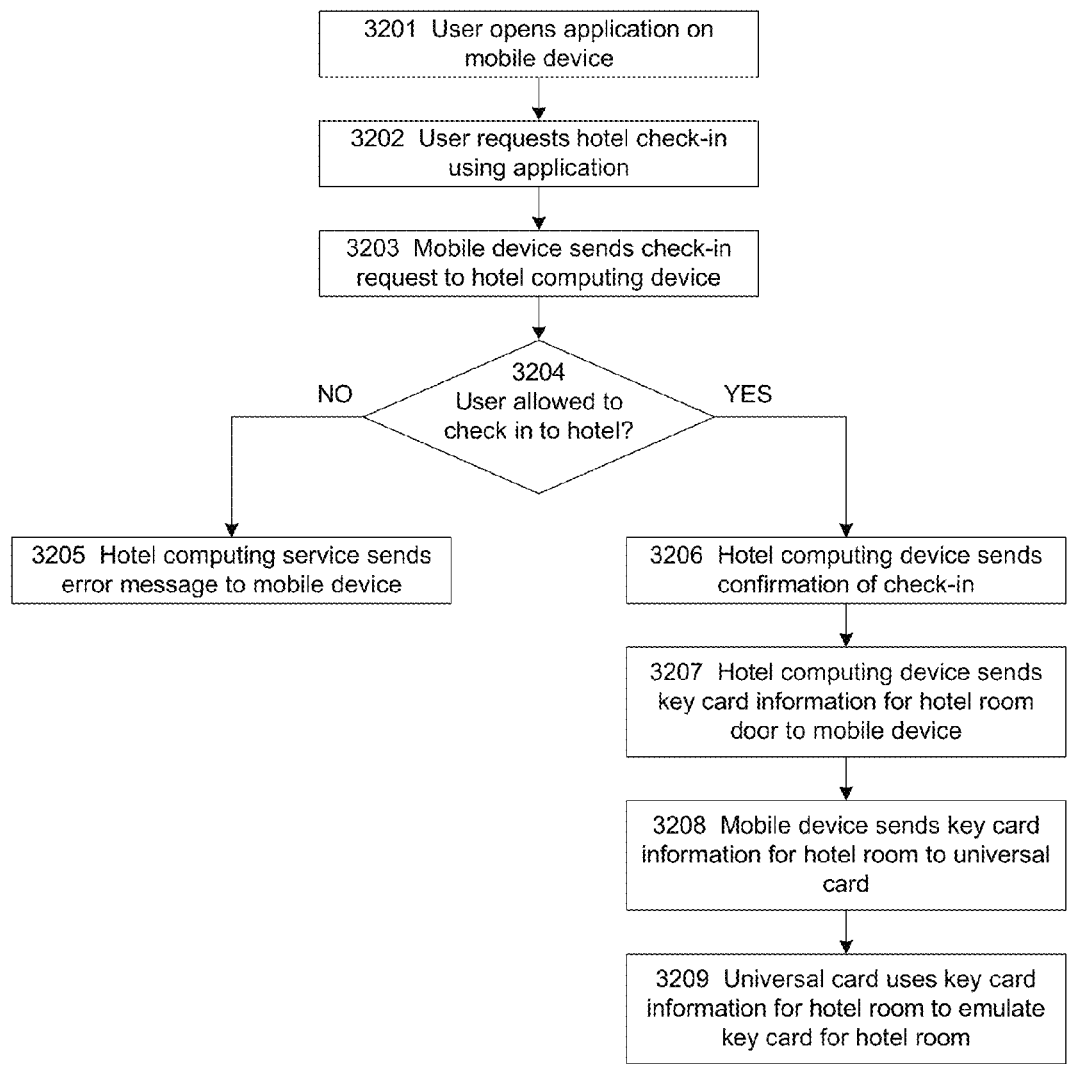
FIG. 32A depicts an embodiment of a method of using a mobile device to check in to a hotel and of using a universal card as a key card for a hotel room.

Referring now to FIG. 32A, depicted is a method of using a mobile device to check in to a hotel and of using a universal card as a key card for a hotel room. At block 3201, a user of a mobile device can open an application on the mobile device. The application can be an application associated with a hotel, an application associated with a travel service, or any other type of application. At block 3202, the user can request hotel check-in using the application. The user can make such a request by selecting a reservation displayed in the application, by making a selection of a hotel room, by entering in a reservation number, or any other information required to check into a hotel. At block 3203, the mobile device can send a check-in request to a hotel computing device. The check-in request can include information entered by the user, an indication of a location of the mobile device, or any other information.

At block 3204, the hotel computing device can determine whether the user is allowed to check in to the hotel. The determination can be based on one or more of information received in the check-in request, an indication of the location of the mobile device, any information previously-known to the hotel computing device, or any combination thereof. If, at block 3204, the hotel computing device determines that the user is not allowed to check in to the hotel, then, at block 3205, the hotel computing device can send an error message to the mobile device. The error message can include an indication why the user is not allowed to check in to the hotel, such as an indication that the user is not in the vicinity of the hotel, the user has an unpaid balance for the hotel room, and the like. However, if, at block 3204, the hotel computing device determines that the user is allowed to check in to the hotel, then the method can proceed to block 3206.

At block 3206, the hotel computing device can send confirmation of check-in to the mobile device. The mobile device can display a corresponding confirmation to the user. At block 3207, the hotel computing device can send key card information for the hotel room door to the mobile device. The key card information can be sent in an encrypted form, and the mobile device may not be able to decrypt the key card information. At block 3208, the key card information can be sent from the mobile device to the universal card. The key card information may still be in the encrypted format when sent from to the universal card, and the universal card may be able to decrypt the key card information and store the decrypted data in a secure element of the universal card. At block 3209, the universal card can use the key card information for the hotel room to emulate a traditional key card. To emulate a traditional key card, the universal card can configure a dynamic data passing mechanism to emulate a static data passing mechanism that would be included in a traditional key card. The dynamic data passing mechanism can include dynamic magnetic stripe, an dynamic RFID transmitter, or a dynamic short range communication transmitter. The universal card may not be configured emulate a traditional key card until after a user of the mobile device requests that the universal card be configured as a key card for the hotel room. In the method depicted in FIG. 32A, the user does not have to interact with a hotel employee or check-in kiosk to be able to check in and have access to the hotel room.

Figure 32B:
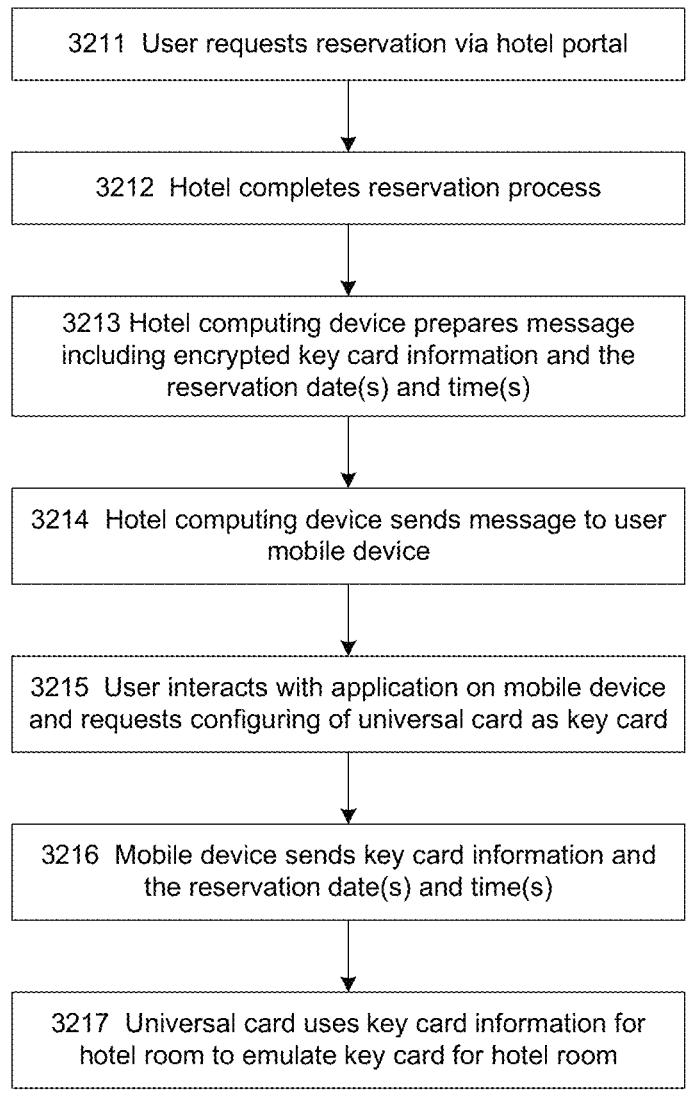
FIG. 32B depicts an embodiment of a method of reserving a hotel room and using a universal card as a key card for a hotel room

Referring now to FIG. 32B, depicted is a method of reserving a hotel room and using a universal card as a key card for a hotel room. At block 3211, a user can request reservation of a hotel room via a hotel portal. The hotel portal can be accessed via an application on the user's mobile device, via a website of the hotel, via a hotel kiosk, or via any other avenue. The request for the reservation can include any or all of a check-in date, and check-out date, a type of requested room, payment information, or any other type of information. At block 3212, the hotel can complete the reservation. Completing the reservation can include ensuring that a hotel room will be available for the dates requested, completing a payment transaction for the hotel room, and any other action by the hotel.

At block 3213, a hotel computing device can prepare a message. The message can include key card information that will allow a universal card to be configured as a key card. The key card information can be encrypted to ensure that the key card information will not be used in an unauthorized manner. The message can also include information about dates and times during which the key card information will be valid, such as from a check-in time on the check-in date and a check-out time on the check-out date. The message can be in the form of a message that can be sent to a user's mobile device, such as an email, a text message, and the like. At block 3214, the hotel computing device can send the message to the mobile device. The message can be sent over one or more networks, such as the internet, a Wi-Fi network in the hotel, a cellular phone network, and any other type of network.

At block 3215, the user can interact with an application on the mobile device to request that the universal card be configured as a key card for the hotel room. The application can use the information received in the message from the hotel computing device to configure the universal card. The application can be an e-wallet application, an application associated with the hotel, or any other type of application. At block 3216, the mobile device can send, to the universal card, the key card information and the date(s) and time(s) that the key card will be valid. If the key card information is received by the mobile device in an encrypted form, the mobile device may be configured to decrypt the key card information and send the key card information to the mobile device in an unencrypted form. If the key card information is received by the mobile device in an encrypted form, the mobile device may also send the key card information to the universal card in the encrypted form. In such a case, the universal card may be configured to decrypt the key card information. At block 3217, the universal card can use the key card information received from the universal card to emulate a key card for the hotel room. If the key card information is received with date(s) and time(s) that the key card will be valid, the universal card may be configured to emulate the key card for the hotel room only at those times that the key card information will be valid.

One of the advantages of the method depicted in FIG. 32B is that any or all of the steps can be formed at any time between the time that the request for the reservation is made and the time that the key card is valid. For example, the portions of the method depicted in blocks 3213 to 3216 can be performed shortly following the hotel's completion of the reservation process at block 3212. In another example, the portions of the method depicted in blocks 3213 to 3216 can be performed shortly before the time that the key card information will be valid. Another advantage of the method depicted in FIG. 32B is that each reservation can be provided with unique key card information. If, after the key card information has been sent to the mobile device, the reservation is no longer valid, such as if the user cancels the reservation, payment for the reservation is not received, and the like, then the key card readers in the hotel can be configured to not accept the unique key card information for that reservation. This may prevent any attempt to use the universal card as a key card despite the reservation having been canceled.

While the embodiment of the method depicted in FIGS. 32A and 32B are described with respect to a hotel room, a similar method could be used in a number of other situations. For example, a similar method could be used with a rental car where the user is able to start a car rental without interacting with a rental car employee. A similar method could be used for users to be able to access a secure parking garage where a user uses an application on a mobile device to pay for parking for a time and the user's universal card is provided with RFID card data for opening a garage door of the parking garage. A number of other situation and embodiments are possible using the same or a similar method.

A universal card can be used as a key card with time restrictions. In one embodiment, the universal card could be used by military personnel to access secure areas in a military facility but only allow the user of the universal card to have access to certain areas of the military facility at certain times. For example, the universal card may allow the user of the universal card to access areas of the military facility when the user is scheduled to be on active duty or in the military facility. In another example, the universal card may allow the user of the universal card to access high security areas of the military facility only at certain times that the user would be expected to need access to those high security areas. In another embodiment, the universal card could be used by airport personnel to access secure areas of an airport at certain times. For example, the universal card may allow a member of a flight crew to access jet way doors to board a plane in preparation for a flight. In another example, the universal card may allow a baggage handler to access the tarmac area of the airport. Such access may be further restricted based on a security level at the airport.

Figure 33:
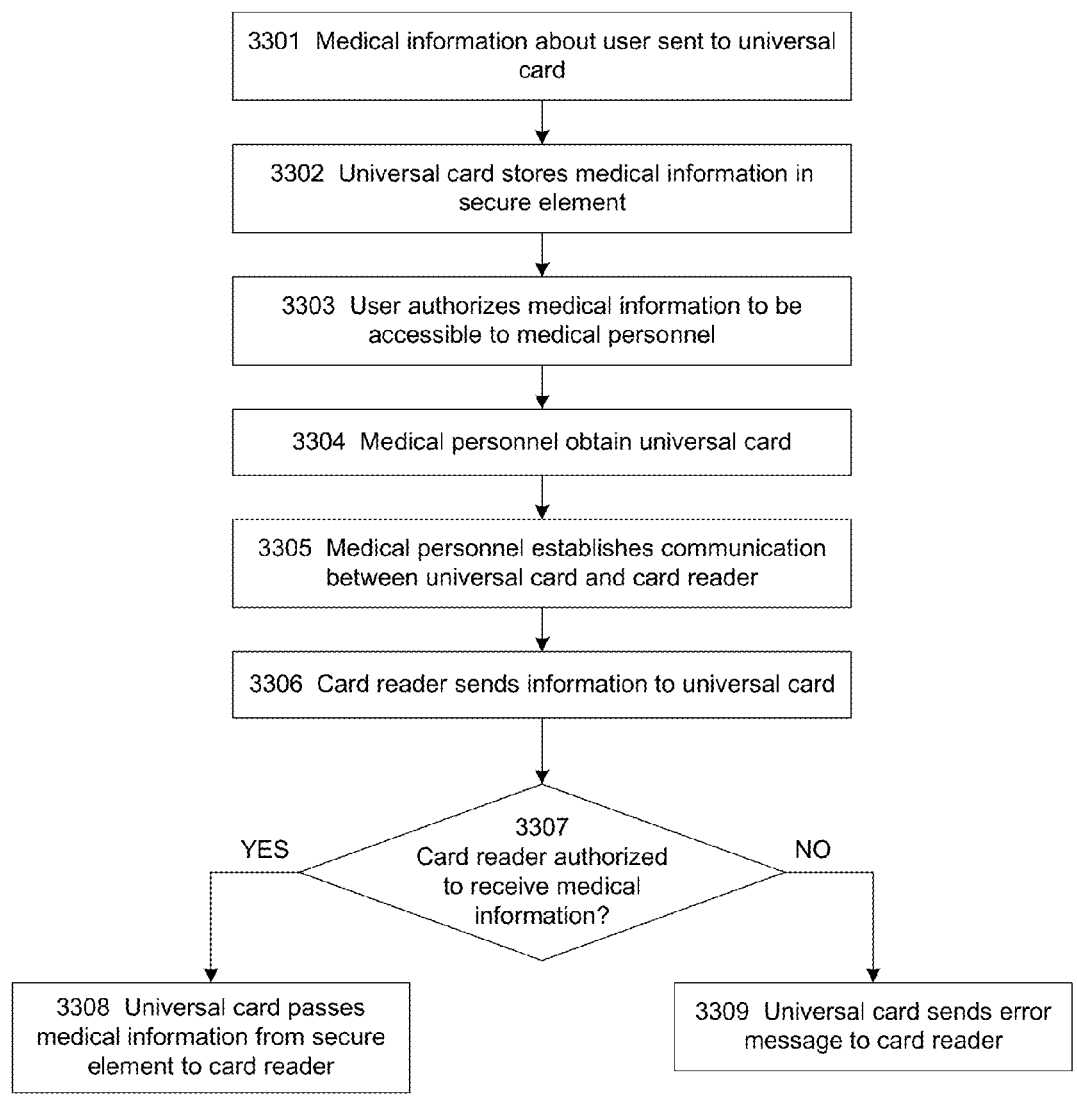
FIG. 33 depicts an embodiment of a method of storing medical information in a universal card and accessing that medical information by medical personnel.

In another example of non-financial uses of a universal card, a universal card can be configured to store medical information, such as a medical history, of a user of the universal card. The universal card can store the medical information in a secure element so that the medical information is not accessible without proper authority to access the medical information. Medical information, or any other type of information, can be by value or by reference. Storage by value stores the actual data itself. Storage by reference may include any reference to a location where the actual data is stored, such as a pointer, a universal resource locator (URL), universal resource indicator (URI), and the like. The reference can identify the actual storage location of the information on a network, such as the internet. As used herein, storing information should be understood to include storage of information by value, storage of information by reference, or any combination thereof Referring now to FIG. 33, depicted is a method of storing medical information in a universal card and accessing that medical information by medical personnel. At block 3301, medical information about the user can be sent to the universal card. The medical information can be information entered into a mobile device by the user, information downloaded to the mobile device and transferred to the universal card, information loaded onto universal card directly from a medical provider, or information sent to the universal card in any other way. At block 3302, the universal card can store the medical information in a secure element of the universal card. Storing the medical information in a secure element will decrease the chance that the medical information can be retrieved by an unauthorized user. At block 3303, the user can authorize medical information to be accessible to medical personnel. The authorization can be authorization for a particular medical provider, such as a certain doctor's officer, authorization for a particular group of medical providers, such as medical providers in a particular insurance network, authorization for particular type of medical personnel, such as emergency medical personnel and other first responders, and other types of authorization. The authorization can also include a limitation on the type of medical information that each of the medical providers can access.

At block 3304, medical personnel can obtain the universal card. The medical personnel can obtain the universal card at some time, such as days, weeks, months, or even years, after the user makes the authorization. The medical personnel can obtain the universal card by the user giving the universal card to the medical personnel. The medical personnel can also obtain the universal card from the user at a time when the user is unconscious, such as in the case of medical first responders arriving on the scene of an accident involving the user. At block 3305, the medical personnel can establish communication between the universal card and a card reader. The card reader can communicate with the universal card using via a magnetic stripe, via a near field communication link, or via an RFID communication link. At block 3306, the card reader can send information to the universal card. The information can include an identifier of the card reader, an identifier of the medical personnel, an identifier of a medical provider, a code associated with the medical personnel, and any other type of information. At block 3307, the universal card can determine whether the card reader is authorized to receive medical information from the universal card. The determination can be based on the information received from the card reader. If, at block 3307, the universal card determines that the card reader is authorized to receive the medical information, then, at block 3308, the universal card can pass the medical information from the secure element of the universal card to the card reader. The card reader can then display the information to the medical personnel. However, if at block 3309, the universal card determines that the card reader is not authorized to receive the medical information, then, at block 3309, the universal card can send an error message to the card reader. The card reader can then display an error message to the medical personnel.

In the embodiment depicted in FIG. 33, the user can of the mobile device can make medical information available to medical personnel in a secure fashion without having to remember the medical information and without having to be able to tell medical personal. For example, if the user is unconscious when medical personnel begin assisting the user, the medical personnel can obtain information from the universal card about allergies of the user, previous injuries that the user has had, and any other information that may affect the medical personnel's care of the user. In another example, the universal card can be used to pass information from one doctor to another. The user may be at one doctor's office, such as a general practice doctor, and be referred to another doctor's office, such as a specialist. The first doctor's office can load, onto the universal card, any or all of the information that needs to be passed to the second doctor's office. For example, the first doctor's office can load medical histories, charts, images (such as X-rays or MRI results), and the like onto the universal card. The user can take the universal card to the second doctor's office, the user can authorize the second doctor's office to have access to the records, and the second doctor's office can download the information loaded onto the universal card by the first doctor's office. Using the universal card to store and transport medical records can be beneficial in any number of other situations.

In another embodiment not depicted in FIG. 33, medical information can be stored in the secure element of a universal card in an encrypted format. If the medical information is entered into a mobile computing device, the mobile computing device can transmit the medical information to the universal card. The medical information can be encrypted either by the mobile device or by the universal card. It may be beneficial to encrypt the medical information on the mobile device before transmitting the medical information to the universal card so that the medical information is encrypted for all transmissions. If the medical information is generated by a medical provider computing device, the medical information could be encrypted by the medical provider computing device. The medical provider computing device can transmit the encrypted medical information directly to the universal card, or the medical provider computing device can transmit the encrypted medical information to the mobile computing device which can transmit the encrypted medical information to the universal card.

The universal card may be configured to provide the encrypted medical information to any card reader requesting the medical information. The card reader may be able to decrypt the encrypted medical information using a particular key. Preferably, the particular key would be available only to authorized card readers, such as card readers associated with first responders or authorized medical personnel. In this embodiment, any card reader may be able to get access to the encrypted medical information while only authorized personnel would be able to decrypt the encrypted medical information. In addition, the universal card or the mobile computing device may be able to decrypt the encrypted medical information only after authentication of the user. Authentication of the user can occur using any one or more of the authentication methods described above. By allowing the encrypted medical information to be decrypted after user authentication, the decrypted medical information can be available to the user without the user needing to have a card reader with the particular key.

The above includes descriptions of a mobile device and a universal card. A mobile device can be any computing device, such as a mobile phone, a Personal Digital Assistants (PDA), an iPod, an MP3 player, a tablet computer, a laptop computer, a personal computer and similar mobile devices. Any of these mobile devices can have short range communication mechanisms, such as a NFC transceiver or a Bluetooth transceiver, which permits the mobile device to communicate with a universal card.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium. When the program code is loaded into and executed by a machine, such as a computer, the machine becomes an apparatus for practicing the disclosed embodiments. In the case of program code execution on programmable computers, the computer will generally include a processor, a storage medium readable by the processor (including volatile and non-volatile memory and/or storage elements), at least one input device and at least one output device. One or more programs are preferably implemented in a high level procedural or object oriented programming language to communicate with a computer system. However, the program(s) can be implemented in assembly or machine language, if desired. In any case, the language may be a compiled or interpreted language, and combined with hardware implementations.

The foregoing description has set forth various embodiments of the apparatus and methods via the use of diagrams and examples. While the present disclosure has been described in connection with the preferred embodiments of the various figures, it is to be understood that other similar embodiments may be used or modifications and additions may be made to the described embodiment for performing the same function of the present disclosure without deviating there from. Therefore, the present disclosure should not be limited to any single embodiment, but rather construed in breadth and scope in accordance with the appended claims. Additional features of this disclosure are set forth in the following claims.

What is claimed:

1. A portable system, comprising:
a mobile computing device comprising a first memory for storing encrypted card data; a first short range transceiver operatively coupled to the first memory and configured to receive the encrypted card data; and a second memory; and
a universal card comprising a secure element; a second short range transceiver; a decrypting module; a first card memory operatively coupled to the decrypting module; a second card memory operatively coupled to the decrypting module and the second short range transceiver; and a dynamic magnetic stripe;
wherein the system is configured to transmit the encrypted card data from the first memory of the mobile computing device to the decrypting module of the universal card via the first and second short range transceivers;
wherein the system is further configured to employ the decrypting module to decrypt the encrypted card data, to store secure card data in the first card memory, and to store non-secure card data in the second card memory;
wherein the system is further configured to transmit the non-secure card data from the second card memory to the second memory of the mobile computing device via the first and second short range transceivers; and
wherein the system is further configured to communicate secure card data from the secure element to a magnetic strip terminal via the dynamic magnetic stripe.

2. The portable system of claim 1, wherein the first short range transceiver comprises a first near field communications (NFC) transceiver, and wherein the second short range transceiver comprises a second NFC transceiver.

3. The portable system of claim 1, wherein the first short range transceiver comprises a first Bluetooth communications transceiver, and wherein the second short range transceiver comprises a second Bluetooth communications transceiver.

4. The portable system of claim 1, wherein the mobile computing device further comprises an application configured to display the non-secure card data.

5. The portable system of claim 1, wherein the universal card further comprises an integrated circuit (IC) chip, wherein the IC chip is configured to receive a personal identification number (PIN) submitted by a user and to verify the correctness of the PIN.

6. The portable system of claim 1, wherein the dynamic magnetic stripe comprises a first track including a first field in which an account number is stored; and a second track in which the account number and one of an expiration date or separator is stored.

7. The portable system of claim 1, wherein the universal card is configurable as a key card.

8. The portable system of claim 1, wherein the universal card is configured as a payment card.

9. The portable system of claim 1, wherein the universal card is configured as a medical card.

10. The portable system of claim 1, wherein the universal card is configured as a gift card.

11. The portable system of claim 1, wherein the system is configured to enable a user to configure the universal card, via the mobile computing device, to emulate a selected card.

12. The portable system of claim 11, wherein the system is configured to carry out the following steps when configuring the universal card:
receiving, via the mobile computing device, a request to configure the universal card as the selected card;
employing the first and second short range transceivers to establish a short range communication link between the mobile computing device and the universal card;
communicating an identifier of the mobile computing device to the universal card;
determining, via the universal card and based on the identifier, whether the mobile computing device is authorized to request configuration of the universal card;
prompting, via the mobile computing device, the user for authentication information;
receiving the authentication information from the user via the mobile computing device;
determining whether the authentication information is valid;
in response to determining that the authentication information is valid, sending the request to configure the universal card as the selected card from the mobile computing device to the universal card; and
employing the dynamic magnetic stripe of the universal card to communicate selected card information from the universal card to a card reader.

13. The portable system of claim 12, wherein the authentication information comprises at least one of a code entered into the mobile computing device, a password entered into the mobile computing device, a personal identification number (PIN) entered into the mobile computing device, and biometric information from the user.

* * * * *